US012760315B2

(12) United States Patent
Koo et al.

(10) Patent No.: US 12,760,315 B2
(45) Date of Patent: Oct. 13, 2026

(54) GENETIC MEANS TO INCREASE NEUTRAL OIL IN VEGETATIVE TISSUES OF PLANTS BY CONDITIONAL INDUCTION OF MEMBRANE LIPID HYDROLYSIS

(71) Applicant: THE CURATORS OF THE UNIVERSITY OF MISSOURI, Columbia, MO (US)

(72) Inventors: Jeong-Kyu Abraham Koo, Columbia, MO (US); Athen N. Kimberlin, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 225 days.

(21) Appl. No.: 17/820,696

(22) Filed: Aug. 18, 2022

(65) Prior Publication Data

US 2023/0227837 A1 Jul. 20, 2023

Related U.S. Application Data

(60) Provisional application No. 63/260,421, filed on Aug. 19, 2021.

(51) Int. Cl.
*C12N 9/18* (2006.01)
*C12N 15/82* (2006.01)

(52) U.S. Cl.
CPC ........... *C12N 15/8247* (2013.01); *C12N 9/18* (2013.01); *C12Y 301/01032* (2013.01)

(58) Field of Classification Search
None
See application file for complete search history.

(56) References Cited

U.S. PATENT DOCUMENTS

2020/0040351 A1* 2/2020 Benning et al. ... C12N 15/8247

OTHER PUBLICATIONS

Ishiguro et al., The Defective in Anther Dehiscence1 Gene Encodes a Novel Phospholipase A1 Catalyzing the Initial Step of Jasmonic Acid Biosynthesis, Which Synchronizes Pollen Maturation, Anther Dehiscence, and Flower Opening in *Arabidopsis*, 2001, The Plant Cell, vol. 13(10), pp. 2191-2210 (Year: 2001).*
Holtsclaw et al., 2017, 56th Annual Meeting of the Phytochemistry Society of North America, Poster Abstract P44, Department of Biochemistry, and Interdisciplinary Plant Group, University of Missouri (Year: 2017).*
Richmond et al., Phospholipases A1, 2011, International Journal of Molecular Sciences, vol. 12, pp. 588-612 (Year: 2011).*
Ishiguro et al., "The Defective in Anther Dehiscence1 Gene Encodes a Novel Phospholipase A1 Catalyzing the Initial Step of Jasmonic Acid Biosynthesis, Which Synchronizes Pollen Maturation, Anther Dehiscence, and Flower Opening in *Arabidopsis*," The Plant Cell, Oct. 2001, vol. 13, pp. 2191-2209.
"Probing the activation mechanism of JA biosynthesis," Abstract of Student Poster, Department of Biochemistry, and Interdisciplinary Plant Group, University of Missouri, Mar. 2015, 1 page.
Wagner et al., "Biochemical Study on Initial Steps of Jasmonate Biosynthesis," Student Internal Poster, Department of Biochemistry, and Interdisciplinary Plant Group, University of Missouri, Jul. 2015, 1 page.

* cited by examiner

*Primary Examiner* — Amjad Abraham
*Assistant Examiner* — Christina L Meadows
(74) *Attorney, Agent, or Firm* — McKee, Voorhees & Sease, PLC

(57) ABSTRACT

The disclosure relates to compositions and methods for increasing oil content of the vegetative tissues of plants. The compositions comprise polynucleotides encoding phospholipase A1 (PLA1) polypeptides and plants, plant parts, plant cells, and seeds comprising such polynucleotides. The methods for increasing oil content of the vegetative tissues of plants comprise introducing a polynucleotide encoding PLA1 polypeptides into the plant. Expression of these PLA1 polynucleotides result in a large accumulation of triacyl glycerides or neutral lipids in vegetative tissues such as leaves that normally contain very little amount of such oil.

19 Claims, 29 Drawing Sheets

Specification includes a Sequence Listing.

GENETIC MEANS TO INCREASE NEUTRAL OIL IN VEGETATIVE TISSUES OF PLANTS BY CONDITIONAL INDUCTION OF MEMBRANE LIPID HYDROLYSIS

CROSS REFERENCE TO RELATED APPLICATIONS

This application claims priority to provisional application U.S. Ser. No. 63/260,421, filed Aug. 19, 2021, which is incorporated herein by reference in its entirety.

GOVERNMENT SUPPORT

This invention was made with government support under Grant No. IOS-2101975 awarded by the National Science Foundation. The Government has certain rights in the invention.

SEQUENCE LISTING XML

The instant application contains a sequence listing, which has been submitted in XML file format by electronic submission and is hereby incorporated by reference in its entirety. Said XML file, created on Aug. 18, 2022, is named P13628US01.xml and is 68,323 bytes in size.

TECHNICAL FIELD

The present disclosure relates to the field of biotechnology. More specifically, the present disclosure relates to compositions and methods for producing oil in plants, particularly in the vegetative tissues of plants.

BACKGROUND

Plant oils such as triacylglycerols (TAGs) are useful for food, industrial feedstock, and biofuel production. TAGs are generally harvested from the seeds of oil crop species, such as soybean and canola. However, seeds represent a very small percentage of total plant biomass. With the demand for improved agricultural productivity and alternative energies, it is recognized that current oil production from a number of devoted seed crops is insufficient. Thus, there is need in the art for increasing the content of oil in other plant tissues and species.

SUMMARY

The present disclosure provides compositions and methods for producing oil in the vegetative tissues of plants.

Plants that produce increased oil content in a vegetative tissue comprising a polynucleotide encoding a phospholipase A1 (PLA1) polypeptide operatively linked to a heterologous inducible promoter functional in a plant cell are provided. In certain embodiments, the PLA1 polypeptide has at least 80%, at least 90%, at least 95%, at least 98%, or at least 99% sequence identity to SEQ ID NO: 1.

Progeny, plant parts, and plant cells of the plants of the disclosure are also provided.

Methods for increasing oil content of a vegetative tissue of a plant are provided. The methods comprise spatially, temporally, or otherwise conditionally increasing activity of a PLA1 polypeptide in a plant so that oil content in vegetative tissue in increased. In certain embodiments, the methods include inducibly increasing expression or activity of a PLA1 polypeptide in the plant. In certain embodiments, the methods comprise introducing in the plant a polynucleotide encoding the PLA1 polypeptide operatively linked to a heterologous inducible promoter functional in a plant cell.

Methods of producing oil from a vegetative tissue of a plant are also provided. The methods comprise contacting the plants or plant parts of the disclosure with an inducer of the promoter, and optionally extracting oil from the plant or the plant part.

Polynucleotides capable of increasing the oil content of the vegetative tissues of a plant are provided. The polynucleotides encode a PLA1 polypeptide having at least 80%, at least 90%, at least 95%, or at least 99% sequence identity to SEQ ID NO: 1. In certain embodiments, the polynucleotide is operably linked to a heterologous inducible promoter that is functional in a plant cell.

Expression constructs, vectors, biological samples, plants, plant parts, and plant cells comprising the polynucleotides of the disclosure are also provided.

Commodity plant products prepared from the plants, plant parts, and plant cells of the disclosure are provided. Methods for producing a commodity plant product comprising processing the plants or plant parts of the disclosure to obtain the product are also provided.

While multiple embodiments are disclosed, still other embodiments of the present disclosure will become apparent based on the detailed description, which shows and describes illustrative embodiments of the disclosure. Accordingly, the figures and detailed description are to be regarded as illustrative in nature and not restrictive.

BRIEF DESCRIPTION OF THE FIGURES

The following drawings form part of the specification and are included to further demonstrate certain embodiments. In some instances, embodiments can be best understood by referring to the accompanying figures in combination with the detailed description presented herein. The description and accompanying figures may highlight a certain specific example, or a certain embodiment. However, one skilled in the art will understand that portions of the example or embodiment may be used in combination with other examples or embodiments.

FIG. 1A-D shows time course of jasmonic acid (FIG. 1A, FIG. 1C) and JA-Ile (FIG. 1B, FIG. 1D) accumulation in the local (FIG. 1A, FIG. 1B) and systemic (FIG. 1C, FIG. 1D) leaves. FIG. 1E-F shows qRT-PCR analysis of JA biosynthetic (OPR3, OPCL1 and JAR1) and JA responsive (JAZ7) gene transcripts in the local (FIG. 1E) and systemic (FIG. 1F) leaves. Data represent mean±SD of three to four biological replicates. Letters above bar graphs indicate statistical significance ($P<0.05$) as determined by pairwise t-tests.

FIG. 2A shows time course qRT-PCR analysis of OPR3 and JAZ8. FIG. 2B shows jasmonic acid levels in leaves treated with COR, wounding (Wnd) or COR plus wounding (COR+Wnd) along with controls (0 h, unwounded (UW)). The inset displays same data in a magnified view. For COR+Wnd, leaves were pre-treated with COR for 1 h before wounding for 0.5 h. Data represent mean±SD of three biological replicates. n.s., not significant. Letters above bar graphs indicate statistical significance (P<0.05) as determined by pairwise t-tests.

FIG. 3A-B shows qRT-PCR analysis of JAZ7 and OPR3 (FIG. 3A), and jasmonic acid and JA-Ile levels (FIG. 3B) in unwounded and wounded plants after treating with mock or cordycepin (Cordy). *Arabidopsis* seedlings (14-d) were incubated with mock (0.01% w/v ethanol in water) or 1 mM Cordy in liquid media for 1 h before wounding for 1 h (FIG. 3A) or 0.5 h (FIG. 3B). FIG. 3C shows protein immunoblot of DAD1-Myc protein expression in Pdex:DAD1-Myc plants (20-d-old). DAD1-Myc expression was induced by including 30 mM dexamethasone (dex) in the liquid media with or without CHX for 6 h and was probed with an antibody against Myc epitope tag. FIG. 3D shows JA accumulation in unwounded or wounded WT plants after treatment w/o cycloheximide (CHX). 14-d-old seedlings were incubated in liquid media containing 0.2 mM CHX for 0, 15, 30 min, and then wounded by hemostats. The tissue was collected after 1 h for LC-MS quantification of jasmonic acid and JA-Ile. Bar graphs represent mean±SD of three biological replicates. Letters in graphs indicate statistical significance (P<0.05) as determined by pairwise t-tests.

FIG. 4A-B shows concentration and time dependent increase of jasmonic acid in *Arabidopsis* seedlings (12-d-old) incubated in liquid MS media containing varying amounts of α-LA for 30 min (FIG. 4A) or 100 μM of α-LA for varying times (FIG. 4B). FIG. 4C shows OPDA synthesis over time by isolated pea chloroplasts incubated w/o 100 μM α-LA. Data represent mean±SD of three biological replicates.

FIG. 5A shows time course of DAD1-like PLA1 expression by wounding. Total RNA from wounded leaves of 24-d-old *Arabidopsis* was subjected to qRT-PCR analyses. FIG. 5B shows qRT-PCR of DAD1 and JAR1 in response to wounding or exogenous jasmonic acid (50 μM) treatment. JAZ7 and OPR3 are controls showing effectiveness of jasmonic acid treatment. Relative expression values are fold-difference compared to the untreated (0 h). ACT8 was used as an internal reference gene and data in bar graphs represent mean±SE of three biological replicates. Letters above bar graphs indicate statistical significance (P<0.05) as determined by pairwise t-tests.

FIG. 6A shows photos of 4-week-old WT, OPR3pro:DAD1 (three independent lines) and OPR3pro:DAD1 in aos background grown under normal *Arabidopsis* growth conditions. FIG. 6B shows an image of 12-d-old seedlings of WT and OPR3pro:DAD1 grown on solid MS media plates. FIG. 6C shows RT-PCR analysis of DAD1 expression in leaves of WT, OPR3pro:DAD1 or OPR3pro:DAD1/aos treated with mock (0.01% ethanol in water) or 50 μM jasmonic acid. ACT8 was an internal reference. FIG. 6D shows anthocyanin levels in 30-d-old WT, OPR3pro:DAD1 and OPR3pro:DAD1/aos w/o jasmonic acid treatment. Either mock or 20 μM jasmonic acid was sprayed once at 15-d-old stage. FIG. 6E shows jasmonic acid and JA-Ile in 21-d-old WT, OPR3pro:DAD1 and OPR3pro:DAD1/aos. Data represent mean SD of three biological replicates with statistical significance (pairwise t-tests, P<0.05) denoted by letters above the bars.

FIG. 7A shows RT-qPCR of DAD1 transcripts in T1 generation lines that survived the antibiotic selection. FIG. 7B shows LC-MS analysis of jasmonic acid in the same plants. Fully expanded rosette leaves of 25-d-old wild-type (WT) and transgenic plants were treated by topical applications of 30 μM dexamethasone (dex) in small droplets on the leaf surfaces for 6 h. Primers do not distinguish endogenous DAD1 from the recombinant DAD1-Myc. Data represent mean of three replicates ±SD for (FIG. 7A) and one replicate for (FIG. 7B). Arrows mark those with correlated increases of both transcripts and hormone. Asterisks mark statistical significance (P<0.05; t-test) compared to WT 2.

FIG. 8A-C shows qRT-PCR (FIG. 8A), protein immunoblot (FIG. 8B), and hormone (FIG. 8C) analyses showing increases of DAD1-Myc transcripts, proteins, and jasmonic acid, respectively, over time by dex (30 μM) treatment in Pdex:DAD1-Myc plants. PCR primers target both native DAD1 and recombinant DAD1-Myc (FIG. 8A). Two specific bands detected on the immunoblot using anti-Myc antibody are the precursor (P) and the mature (M) forms of DAD1-Myc before and after cleavage of the chloroplast transit peptide. Some batches of commercial Myc-antibodies detect a non-specific protein band (asterisk) across all samples (FIG. 8B). FIG. 8D-F shows DAD1-Myc transcripts (FIG. 8D), DAD1-Myc proteins (FIG. 8E), and jasmonic acid (FIG. 8F) induction in different aged Pdex:DAD1-Myc plants after 8 h of mock or dex treatment. Data in bar graphs represent mean±SD of three biological replicates. Letters above bars denote statistical significance (pairwise t-tests, P<0.05).

FIG. 9A shows qRT-PCR analysis of DAD1-Myc (plus endogenous DAD1) transcripts in WT or Pdex:DAD1-Myc plants treated either with wounding (W) or dex, or both (dex+W). Inset displays a magnified view. Relative expression values are based on comparisons to the dex-treated WT. Data represent mean SE of three biological replicates. FIG. 9B-C shows jasmonic acid levels in 30-d (FIG. 9B) or 15-d (FIG. 9C)-old WT or Pdex:DAD1-Myc plants treated with dex, wounding (W), or both (dex+W). Data represent mean±SD of three biological replicates. Ten L of 30 μM dex was added as small droplets on the adaxial surface of the leaf and incubated for 8 h. Wounding was administered by crushing leaves twice across the mid-rib using a hemostat at 6 h post dex treatment, and tissue was harvested after 2 h of wounding. Letters above indicate statistical significance (pairwise t-tests, P<0.05).

FIG. 10A shows immunoblot showing induction of DAD1-Myc in the local (loc) (leaf 3, 4) and systemic (sys) (6, 7) leaves after 6 h of 30 μM dex treatment (circle in the cartoon) on the systemic leaves of Pdex:DAD1-Myc. WT leaves were treated with dex as control. 'P' and 'M' denote the precursor and the mature (transit peptide cleaved) DAD1-Myc, respectively, and the asterisk (*) indicates nonspecific detection. FIG. 10B shows wound-induced systemic JA accumulation w/o preinduction by dex. Systemic leaves (leaf 6, 7) were pre-treated with mock or dex for 6 h before wounding the local leaves (leaf 3, 4). JA content in the systemic leaves was determined after 15 min of local wounding by crushing the leaves with hemostats twice perpendicular to the midvein. 24-d-old plants were used for all experiments. Data in bar graphs represent mean±SD of four biological replicates. Letters above bars indicate statistical significance (Student's t-test, P<0.05). Inset displays a magnified view.

FIG. 11A shows immunoblot of protein extracts from Pdex:DAD1-Myc probed with antibodies against Myc, LOX, AOC, and JAR1. 14-d old seedlings that were pretreated with dex (12 h) was submerged in MS media containing 0.2 mM CHX for shown duration of time. FIG. 11B shows DAD1-Myc proteins in dex-induced (12 h) Pdex:DAD1-Myc seedlings after incubation with CHX and 0, 10, and 100 μM of α-LA. FIG. 11C shows DAD1-Myc proteins in dex-induced (12 h) Pdex:DAD1-Myc seedlings after incubation with CHX, CHX+wounding (Wnd), or mock (0.01% w/v ethanol in water). Wounding was administered at the beginning of CHX treatment with a hemostat.

FIG. 12A-C shows qRT-PCR (FIG. 12A), protein immunoblot (FIG. 12B), and oil (FIG. 12C) analyses showing increases of DAD1-Myc mRNA transcripts, proteins, and TAG, respectively, over time by dex (30 μM) treatment in Pdex:DAD1-Myc plants. Two specific bands detected on the immunoblot using anti-Myc antibody are the precursor (P) and the mature (M) forms of DAD1-Myc before and after cleavage of the chloroplast transit peptide. Some batches of commercial Myc-antibodies detect a nonspecific protein band (asterisk) across all samples. Numbers Asterisks above bar graphs indicate statistical significance (Students' t test, *P<0.05, P<0.01) compared to WT. Data are mean±SD of three biological replicates. FIG. 12D shows laser scanning confocal microscopy image of BODIPY-stained leaves showing accumulation of oil bodies (green punctate organelles) in leaves of dex-treated Pdex:DAD1-Myc but not wildtype (WT). Red oval shaped organelles are chloroplasts. Scale bar=20 μm. FIG. 12**E shows thin layer chromatography showing comparison of TAG levels among dex-induced Pdex:DAD1-Myc (induction times are as displayed) compared to WT and other lines reported to have increased leaf TAGs. Lines A: LDAP1 OE; B: FIT2 OE; C: tungDGAT2/FADX OE; D: tungDGAT2 OE, E: WRI1 OE/AGPase RNAi, F: WRI1 OE, G: SEIPIN1 OE.

FIG. 13A shows phylogeny of *N. benthamiana* PLAs closely related to *N. attenuata* (Na) GLA1 and *Arabidopsis* AtDAD1 and AtDGL. Maximum-likelihood with 100 bootstraps was applied to construct the tree using Muscle, Mega7 and iTOL tools. NbGLA1 and NbGLA2 cluster with NaGLA1. FIG. 13B-C shows RT-PCR of NbGLA1 and NbGLA2 (FIG. 13B) and a time course of JA (FIG. 13C) in unwounded and wounded *N. benthamina* leaves infiltrated with *Agrobacterium* carrying either empty (Mock) or VIGS constructs targeting both NbGLA1 and NbGLA2. 'a' and 'b' are two independent infiltrations. NbEF1a is an internal reference. FIG. 13D-E shows transient expression of NbGLA1 and NbGLA1-GFP in tobacco leaves increases JA (dex) but co-treatment with wounding (dex+wound) dramatically enhances the JA level ca.10 fold.

DETAILED DESCRIPTION

Figure 1A:
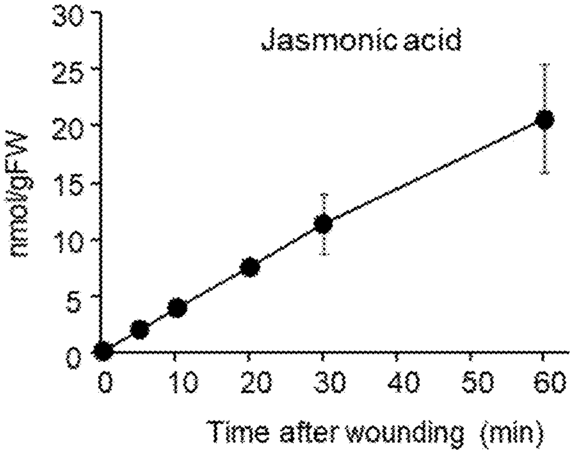
FIG. 1A-F shows wound-induced JA biosynthesis spikes earlier than JA biosynthetic and JA responsive gene transcripts. Local leaves (leaf 3,4) were wounded using a pair of hemostats and both local damaged and remote undamaged (systemic) leaves (leaf 6,7) were analyzed.

The present disclosure relates to plants that have been modified to produce more oil in their vegetative tissues, as well as methods of generating and using such plants to produce oil. The plants described herein have been modified to express a phospholipase A1 (PLA1) gene, such as DEFECTIVE IN ANTHER DEHISCIENCE 1 (DAD1), under control of an inducible promoter. Expression of these PLA1 genes result in large accumulation of triacyl glycerides or neutral lipids in vegetative tissues such as leaves that normally contain very little amount of such oil. Plants with increased oil content are useful as fodder for animals, as sources oil for human consumption, and as a source of oil for biofuels.

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

It is to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Similarly, the word "or" is intended to include "and" unless the context clearly indicate otherwise. The word "or" means any one member of a particular list and also includes any combination of members of that list. Further, all units, prefixes, and symbols may be denoted in its SI accepted form.

Numeric ranges recited within the specification are inclusive of the numbers defining the range and include each integer within the defined range. Throughout this disclosure, various embodiments of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, flakes, syrup, oil, starch, and cereals manufactured in whole or in part to contain crop plant by-products. In certain embodiments, the biological sample is "non-regenerable" (i.e., incapable of being regenerated into a plant or plant part).

As used herein, the terms "include," "includes," and "including" are to be construed as at least having the features to which they refer while not excluding any additional unspecified features.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, "modified", in the context of plants, seeds, plant components, plant cells, and plant genomes, refers to a state containing changes or variations from their natural or native state. For instance, a "native transcript" of a gene refers to an RNA transcript that is generated from an unmodified gene. Typically, a native transcript is a sense transcript. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of *Agrobacterium* transformation or microprojectile bombardment), or a combination thereof. In one embodiment, a modified plant provided herein comprises no non-plant genetic material or sequences. In yet another embodiment, a modified plant provided herein comprises no interspecies genetic material or sequences.

As used herein, the terms "nucleic acid," "nucleic acid molecule," "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present disclosure further provides a nucleic acid that is the complement (which can be either a full complement or a partial complement) of a nucleic acid, nucleotide sequence, or polynucleotide.

By "operably linked" or "operably associated," it is meant that the indicated elements are functionally related to each other, and are also generally physically related. Thus, the term "operably linked" or "operably associated" as used herein, refers to nucleotide sequences on a single nucleic acid molecule that are functionally associated. Therefore, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

As used herein, "plant" refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., F1, F2, F3, F4, F5, F6, F7, etc. A plant cell is a biological cell of a plant, taken from a plant or derived through culture from a cell taken from a plant.

The term "primer" as used herein encompasses any nucleic acid that is capable of priming the synthesis of a nascent nucleic acid in a template-dependent process, such as PCR. Typically, primers are oligonucleotides from 10 to 30 nucleotides in length, but longer sequences may be used. Primers may be provided in single or double-stranded form. Probes may be used as primers, but are designed to bind to the target DNA or RNA and need not be used in an amplification process.

"Regulatory elements" refer to nucleotide sequences located upstream (5' non-coding sequences), within, or downstream (3' non-coding sequences) of a coding sequence, and which influence the transcription, RNA processing or stability, or translation of the associated coding sequence. Regulatory elements may include, but are not limited to, promoters, translation leader sequences, introns, and polyadenylation recognition sequences. Regulatory elements present on a recombinant DNA construct that is introduced into a cell can be endogenous to the cell, or they can be heterologous with respect to the cell. The terms "regulatory element" and "regulatory sequence" are used interchangeably herein.

Phospholipases

Phospholipases are enzymes that hydrolyze the ester bonds of phospholipids. Corresponding to their importance in the metabolism of phospholipids, these enzymes are widespread among prokaryotes and eukaryotes. The phospholipases affect the metabolism, construction and reorganization of biological membranes and are involved in signal cascades. Several types of phospholipases are known which differ in their specificity according to the position of the bond attacked in the phospholipid molecule.

Phospholipase A1 (PLA1) enzymes remove the 1-position fatty acid to produce free fatty acid and 1-lyso-2-acylphospholipid. Phospholipase A2 (PLA2) enzymes remove the 2-position fatty acid to produce free fatty acid and 1-acyl-2-lysophospholipid. PLA1 and PLA2 enzymes can be intra- or extra-cellular, membrane-bound or soluble. Phospholipase C (PLC) enzymes remove the phosphate moiety to produce 1,2 diacylglycerol and a phosphate ester. Phospholipase D (PLD) enzymes produce 1,2-diacylglycerophosphate and base group.

PLA1 sequences are provided that increase the oil content of vegetative tissues of a plant. Such sequences include the amino acid sequence set forth in SEQ ID NO: 1, and variants and derivatives thereof. Also provided are polynucleotide sequences encoding such amino acid sequences, including SEQ ID NO: 2.

Several embodiments also relate to the use of PLA1 or variants thereof that increase the oil content of vegetative tissues of a plant. "Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode PLA1 polypeptides described above. Naturally occurring allelic variants can be identified with the use of well-known molecular biology techniques, as, for example, with polymerase chain reaction (PCR) and hybridization techniques as outlined herein. Variant polynucleotides also include synthetically derived polynucleotides, such as those generated, for example, by using site-directed mutagenesis but which still encode a PLA1 polypeptide that increases the oil content of vegetative tissues of a plant. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide.

In certain embodiments, variants of a polynucleotide include at least one nucleotide substitution, insertion, or deletion so that they do not recite a naturally occurring nucleic acid sequence. In certain embodiments, the polynucleotide include at least one nucleotide substitution, insertion, or deletion relative to SEQ ID NO: 2.

Variants of a particular polynucleotide encoding a PLA1 that increases the oil content of vegetative tissues of a plant are encompassed and can be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and algorithms described below. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

Methods of alignment of sequences for comparison are well known in the art and can be accomplished using mathematical algorithms such as the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; and the algorithm of Karlin and Altschul (1990) *Proc. Natl. Acad. Sci. USA* 872264, modified as in Karlin and Altschul (1993) Proc. Natl. Acad. Sci. USA 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

Homologs (e.g., orthologs, paralogs) of SEQ ID NO: 1 (*Arabidopsis thaliana* DAD1) encompassed by the present disclosure include, but are not limited to, polypeptides comprising the amino acid sequences set forth in SEQ ID NOs: 1, 3, 5, 7, 9, 11, 13, 15, 17, 19, 21, 23, 25, 27, 29, 31, 33, 35, and 37. Table 1 also provides examples of plant homologs of SEQ ID NO: 1.

"Orthologs" and "paralogs" encompass evolutionary concepts used to describe the ancestral relationships of genes. Paralogs are genes within the same species that have originated through duplication of an ancestral gene; orthologs are genes from different organisms that have originated through speciation, and are also derived from a common ancestral gene.

TABLE 1

| Name | Species | Protein Sequence | Coding Sequence |
|---|---|---|---|
| AtDAD1 | *Arabidopsis thaliana* | SEQ ID NO: 1 | SEQ ID NO: 2 |
| BoDAD1 | *Brassica oleracea* | SEQ ID NO: 3 | SEQ ID NO: 4 |
| BrDAD1 | *Brassica rapa* | SEQ ID NO: 5 | SEQ ID NO: 6 |
| BnDAD1 | *Brassica napus* | SEQ ID NO: 7 | SEQ ID NO: 8 |
| CsDAD1 | *Camelina sativa* | SEQ ID NO: 9 | SEQ ID NO: 10 |
| GmDAD1 | *Glycine max* | SEQ ID NO: 11 | SEQ ID NO: 12 |
| HaDAD1 | *Helianthus annuus* | SEQ ID NO: 13 | SEQ ID NO: 14 |
| PvDAD1 | *Phaseolus vulgaris* | SEQ ID NO: 15 | SEQ ID NO: 16 |
| SlDAD1 | *Solanum lycopersicum* | SEQ ID NO: 17 | SEQ ID NO: 18 |
| StDAD1 | *Solanum tuberosum* | SEQ ID NO: 19 | SEQ ID NO: 20 |
| OsDAD1 | *Oryza sativa* | SEQ ID NO: 21 | SEQ ID NO: 22 |
| SbDAD1 | *Sorghum bicolor* | SEQ ID NO: 23 | SEQ ID NO: 24 |
| ZmDAD1 | *Zea mays* | SEQ ID NO: 25 | SEQ ID NO: 26 |
| AtDALL1 | *Arabidopsis thaliana* | SEQ ID NO: 27 | SEQ ID NO: 28 |
| AtDALL2 | *Arabidopsis thaliana* | SEQ ID NO: 29 | SEQ ID NO: 30 |
| AtDALL3 | *Arabidopsis thaliana* | SEQ ID NO: 31 | SEQ ID NO: 32 |
| AtDALL4 | *Arabidopsis thaliana* | SEQ ID NO: 33 | SEQ ID NO: 34 |
| AtDALL5 | *Arabidopsis thaliana* | SEQ ID NO: 35 | SEQ ID NO: 36 |
| NbGLA1 | *Nicotiana benthamiana* | SEQ ID NO: 37 | SEQ ID NO: 38 |

Additional polynucleotide sequences encoding a PLA1 polypeptide may be identified using methods well known in the art based on their ability to increase the oil content of the vegetative tissues of a plant. For example, candidate PLA1 genes are expressed in tobacco, *Arabidopsis*, or other easily transformed plant and the resultant transformant plants assessed for oil content.

Those skilled in the art may also find further candidate PLA1 genes based on genome synteny and sequence similarity. In one embodiment, additional gene candidates can be obtained by hybridization or PCR using sequences based on the PLA1 nucleotide sequences noted above.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art. See, for example, Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

By "hybridizing to" or "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the disclosure as described herein.

With regard to a defined polypeptide, it will be appreciated that percent identity figures higher than those provided above will encompass preferred embodiments. Thus, where applicable, in light of the minimum percent identity figures, it is preferred that the PLA1 polypeptide comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 1.

By "variant" polypeptide is intended a polypeptide derived from the protein of SEQ ID NO: 1, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. Thus, functional variants and fragments of the PLA1 polypeptides, and nucleic acid molecules encoding them, also are within the scope of the present disclosure, and unless specifically described otherwise, irrespective of the origin of said polypeptide and irrespective of whether it occurs naturally.

In addition, one of ordinary skill in the art will further appreciate that changes can be introduced by mutation into the nucleotide sequences thereby leading to changes in the amino acid sequence of the encoded proteins without altering the biological activity of the proteins. Thus, for example, an isolated polynucleotide molecule encoding a PLA1 polypeptide having an amino acid sequence that differs from that of SEQ ID NO: 1 can be created by introducing one or more nucleotide substitutions, additions, or deletions into the corresponding nucleotide sequence, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present disclosure.

A deletion refers to removal of one or more amino acids from a protein. An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag·100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or R-sheet structures). Amino acid substitutions are typically of single residues but may be clustered depending upon functional constraints placed upon the polypeptide and may range from 1 to 10 amino acids; insertions will usually be of the order of about 1 to 10 amino acid residues. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif. Conservative substitution tables are well known in the art (see for example Creighton (1984) Proteins. W. H. Freeman and Company (Eds).

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

In certain embodiments, the polypeptides include at least one amino acid substitution, insertion, or deletion so that they do not recite a naturally occurring amino acid sequence. In certain embodiments, the polypeptides include at least one amino acid substitution, insertion, or deletion relative to SEQ ID NO: 1.

Expression Constructs

PLA1 polynucleotides as described herein can be provided in an expression construct. Expression constructs generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence.

A "promoter" is a region of DNA involved in recognition and binding of RNA polymerase and other proteins to initiate transcription. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels.

A plant promoter includes a promoter capable of initiating transcription in a plant cell. For a review of plant promoters, see, Potenza et al., 2004, In Vitro Cell Dev Biol 40:1-22; Porto et al., 2014, Molecular Biotechnology (2014), 56(1), 38-49.

Constitutive promoters include, for example, the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; ALS promoter (U.S. Pat. No. 5,659,026) and the like.

Tissue-preferred promoters can be utilized to target enhanced expression within a particular plant tissue. Tissue-preferred promoters include, for example, WO2013/103367 published on 11 Jul. 2013, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994)

*Results Probl Cell Differ* 20:181-96; and Guevara-Garcia et al., (1993) *Plant J*4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teen et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459, 252; 5,401,836; 5,110,732 and 5,023,179.

Useful promoters for expression in mature leaves are those that are switched on at the onset of senescence, such as the SAG promoter from *Arabidopsis* (Gan et al. (1995) *Science* 270:1986-1988).

The term “inducible promoter” refers to a promoter that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners. In certain embodiments, an inducible promoter is used. In certain embodiments, a chemical inducible promoter is used.

Chemical inducible (regulated) promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-11-27, WO93/01294), activated by hydrophobic electrophilic compounds used as pre-emergent herbicides, and the tobacco PR-1 a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991)*Mol Gen Genet* 227:229-37; U.S. Pat. Nos. 5,814,618 and 5,789,156).

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int’l Patent Application Publication Nos. WO 97/06269 and WO 97/06268) systems and glutathione 5-transferase promoters. Likewise, one can use any of the inducible promoters described in Gatz (1996) *Current Opinion Biotechnol.* 7:168-172 and Gatz (1997) *Annu.* Rev. *Plant Physiol. Plant Mol. Biol.* 48:89-108. Other chemically inducible promoters useful for directing the expression of the nucleotide sequences in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395.

Pathogen inducible promoters induced following infection by a pathogen include, but are not limited to those regulating expression of PR proteins, SAR proteins, beta-1, 3-glucanase, chitinase, etc.

A stress-inducible promoter includes the RD29A promoter (Kasuga et al. (1999) Nature Biotechnol. 17:287-91). One of ordinary skill in the art is familiar with protocols for simulating stress conditions such as drought, osmotic stress, salt stress and temperature stress and for evaluating stress tolerance of plants that have been subjected to simulated or naturally-occurring stress conditions.

Another example of an inducible promoter useful in plant cells is the heat inducible and/or chemical inducible promoter ZmCAS1 promoter, described in US patent application, US 2013-0312137A1, published on Nov. 21, 2013, incorporated by reference herein. Other heat inducible promoters or promoters comprising or fused to heat shock elements are known in the art, such as but not limiting to, the plant heat shock promoter or elements described in U.S. Pat. No. 544,858 and U.S. Pat. No. 561,399.

New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, N.Y.: Academic Press), pp. 1-82.

An expression construct can comprise a promoter sequence operably linked to a polynucleotide sequence encoding a PLA1 polypeptide as described herein. Promoters can be incorporated into a polynucleotide using standard techniques known in the art. Multiple copies of promoters or multiple promoters can be used in an expression construct as described herein. In some embodiments, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

The choice of promoter will vary depending on the temporal and spatial requirements for expression, and also depending on the host cell to be transformed. Thus, for example, expression of the nucleotide sequences can be in any plant and/or plant part, (e.g., in leaves, in stems, in inflorescences, in roots, seeds and/or seedlings, and the like). In many cases, however, expression in multiple tissues is desirable. Although many promoters from dicotyledons have been shown to be operational in monocotyledons and vice versa, a dicotyledonous promoter may be selected for expression in dicotyledons, and a monocotyledonous promoter for expression in monocotyledons. However, there is no restriction to the provenance of selected promoters; it is sufficient that they are operational in driving the expression of the nucleotide sequences in the desired cell.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' noncoding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989)*Molecular Biology of RNA* 237-256); and MCMV leader (Lommel et al. (1991) *Virology* 81:382-385). See also, Della-Cioppa et al. (1987) *Plant Physiol.* 84:965-968.

Expression constructs may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides described herein. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

An expression construct can include a nucleotide sequence for a selectable marker, which can be used to select a transformed plant, plant part, or plant cell. As used herein, "selectable marker" means a nucleotide sequence that when expressed imparts a distinct phenotype to the plant, plant part, or plant cell expressing the marker and thus allows such transformed plants, plant parts, or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening. Of course, many examples of suitable selectable markers are known in the art and can be used in the expression constructs described herein.

Examples of selectable markers include, but are not limited to, a nucleotide sequence encoding neo or nptII, which confers resistance to kanamycin, G418, and the like (Potrykus et al. (1985)*Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella* ozaenae that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression construct.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) J. *Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem.*

*Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression construct.

Optionally the gene encoding the PLA1 polypeptide is codon optimized to remove features inimical to expression and codon usage is optimized for expression in the particular crop (see, for example, U.S. Pat. No. 6,051,760; EP 0359472; EP 80385962; EP 0431829; and Perlak et al. (1991) *PNAS USA* 88:3324-3328; all of which are herein incorporated by reference).

Genome Editing

Targeted modification of plant genomes through the use of genome editing methods can be used to introduce a PLA1 gene or to inducibly increase expression of a PLA1 gene through modification of plant genomic DNA. Genome editing methods can enable targeted insertion of one or more nucleic acids of interest into a plant genome. Genome editing uses engineered nucleases such as RNA guided DNA endonucleases or nucleases composed of sequence specific DNA binding domains fused to a non-specific DNA cleavage module. These engineered nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption. Engineered nucleases useful in the methods of the present disclosure include zinc finger nucleases (ZFNs), transcription activator-like (TAL) effector nucleases (TALEN) and CRISPR/Cas9 type nucleases.

A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the Cis2His2 type of zinc finger that is very generally represented, for example, by the zinc finger transcription factors TFIIIA or Sp1. In a preferred embodiment, the zinc finger domain comprises three Cis2His2 type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques (see, for example, Bibikova et al., 2002).

The ZFN DNA-cleavage domain is derived from a class of non-specific DNA cleavage domains, for example the DNA-cleavage domain of a Type II restriction enzyme such as Fold (Kim et al., 1996). Other useful endonucleases may include, for example, HhaI, HindIII, Nod, BbvCI, EcoRI, BglI, and AlwI.

A transcription activator-like (TAL) effector nuclease (TALEN) comprises a TAL effector DNA binding domain and an endonuclease domain. TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AhvI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Distinct from the site-specific nucleases described above, the clustered regulatory interspaced short palindromic repeats (CRISPR)/Cas system provides an alternative to ZFNs and TALENs for inducing targeted genetic alterations, via RNA-guided DNA cleavage.

CRISPR systems rely on CRISPR RNA (crRNA) and transactivating chimeric RNA (tracrRNA) for sequence-specific cleavage of DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

In certain embodiments, isolated nucleic acids which serve as a promoter (e.g., an inducible promoter) may be introduced in an appropriate position (typically upstream) of a non-heterologous form of a polynucleotide so as to alter expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a PLA1 gene so as to control the expression of the gene.

Transformation Methods

Suitable methods for transformation of host plant cells include virtually any method by which DNA or RNA can be introduced into a cell (for example, where a recombinant DNA construct is stably integrated into a plant chromosome or where a recombinant DNA construct or an RNA is transiently provided to a plant cell) and are well known in the art. Two effective methods for cell transformation are *Agrobacterium*-mediated transformation and microprojectile bombardment-mediated transformation. Microprojectile bombardment methods are illustrated, for example, in U.S. Pat. Nos. 5,550,318; 5,538,880; 6,160,208; and 6,399,861. *Agrobacterium*-mediated transformation methods are described, for example in U.S. Pat. No. 5,591,616, which is incorporated herein by reference in its entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores and pollen. Callus can be initiated from tissue sources including, but not limited to, immature or mature embryos, hypocotyls, seedling apical meristems, microspores and the like. Cells containing a transgenic nucleus are grown into transgenic plants.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Transformation of a cell may be stable or transient. Thus, in some embodiments, a plant cell is stably transformed with a nucleic acid molecule. In other embodiments, a plant is transiently transformed with a nucleic acid molecule. "Transient transformation" in the context of a polynucleotide means that a polynucleotide is introduced into the cell and does not integrate into the genome of the cell. By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

A nucleic acid (e.g., SEQ ID NO: 2, or a nucleotide sequence encoding the amino acid sequence of SEQ ID NO: 1) can be introduced into a cell by any method known to those of skill in the art.

In some embodiments, transformation of a cell comprises nuclear transformation. In other embodiments, transformation of a cell comprises plastid transformation (e.g., chloroplast transformation).

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Bio-*

*technology*, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and/or plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods provided herein.

Likewise, the genetic properties engineered into the transgenic seeds and plants, plant parts, and/or plant cells described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleotide sequence therefore can be introduced into the plant, plant part and/or plant cell in any number of ways that are well known in the art. The methods do not depend on a particular method for introducing one or more nucleotide sequences into a plant, only that they gain access to the interior of at least one cell of the plant. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, in separate transformation events, or, for example, in plants, as part of a breeding protocol.

Plants with Increased Oil Content in Vegetative Tissues

Several embodiments relate to plant cells, plant tissues, plants, and seeds that comprise a polynucleotide encoding a PLA1 polypeptide, wherein expression of the polynucleotide increases the oil content of vegetative tissues of the plant.

Plants that are useful in the methods of the present disclosure include all plants which belong to the superfamily Viridiplantae, in particular monocotyledonous and dicotyledonous plants including fodder or forage legumes, ornamental plants, food crops, trees or shrubs selected from *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus*, Annona spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., Benincasa *hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis* oleifera), *Eleusine coracana, Eragrostis tef Erianthus* sp., Eriobotrya *japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. In certain embodiments, the plant is a crop plant. Examples of crop plants include inter *alia* soybean, sunflower, canola, alfalfa, rapeseed, cotton, tomato, potato, or tobacco.

Certain embodiments encompass a progeny or a descendant of a plant of the disclosure as well as seeds derived from the plants and cells derived from the plants as described herein.

In some embodiments, the present disclosure provides a progeny or descendant plant derived from a plant comprising in at least some of its cells a polynucleotide operably linked to an inducible promoter functional in a plant cell, the promoter capable of expressing a PLA1 polypeptide encoded by the polynucleotide, wherein the progeny or descendant plant comprises in at least some of its cells the polynucleotide operably linked to the inducible promoter, the expression of the PLA1 polypeptide conferring to the progeny or descendant plant increased oil content in vegetative tissues.

In one embodiment, seeds of the present disclosure preferably comprise the vegetative oil characteristics of the plant. In other embodiments, a seed is capable of germination into a plant comprising in at least some of its cells a polynucleotide operably linked to an inducible promoter functional in a plant cell, the promoter capable of expressing a PLA1 polypeptide encoded by the polynucleotide, the expression of the PLA1 polypeptide conferring to the progeny or descendant plant increased oil content in vegetative tissues.

In some embodiments, plant cells of the present disclosure are capable of regenerating a plant or plant part. In other embodiments, plant cells are not capable of regenerating a plant or plant part. Examples of cells not capable of regenerating a plant include, but are not limited to, endosperm, seed coat (testa and pericarp), and root cap.

In another embodiment, the disclosure refers to a plant cell transformed by a nucleic acid encoding a PLA1 polypeptide as described herein, wherein expression of the nucleic acid in the plant cell results in increased oil content in vegetative tissues as compared to a wild type variety of the plant cell.

Several embodiments provide a commodity plant product prepared from the plants of the disclosure. In some embodiments, examples of plant products include, without limitation, grain, oil, and meal. In one embodiment, a commodity plant product is plant grain (e.g., grain suitable for use as feed or for processing), plant oil (e.g., oil suitable for use as food or biodiesel), or plant meal (e.g., meal suitable for use as feed). A preferred commodity plant product is fodder, seed meal, oil, or seed-treatment-coated seeds. In certain embodiments, the meal and/or oil comprise the PLA1 polynucleotide or PLA1 polypeptide.

In certain embodiments, a commodity plant product prepared from a plant or plant part is provided. In certain embodiment, the plant or plant part comprises in at least some of its cells a polynucleotide operably linked to an inducible promoter functional in plant cells, the promoter capable of expressing a PLA1 polypeptide encoded by the polynucleotide in the presence of the inducer.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the method is performed, while allowing repeated times the steps of product production e.g. by repeated removal of harvestable parts of the plants of the disclosure and if necessary further processing of these parts to arrive at the product. It is also possible that the step of growing the plants is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally, the plants are grown for some time before the product is produced.

With the use of an inducible promoter, the gene is not expressed until the plant is fully grown and ready for oil extraction. Upon induction, the vegetative tissues (e.g., leaves) can be harvested within a day or two. In certain embodiments, plants can be harvested prior to the gene activation and can be treated with the inducer afterwards in, for example, enclosed bioreactors. Harvested tissue materials are still capable of inducing genes and oil accumulation, and the induced oil accumulation can happen in a matter of few hours.

Controlled induction of oil from leaves and other parts of plants which represent the bulk of biomass that are normally discarded after harvest holds great potential for renewable biodiesel production. In addition to the prospect of minimizing the waste and maximizing the use of plant biomass, this has potential to avoid competition with foods which is often a criticism of growing plants for bioenergy.

An additional use of such plants is as oil rich feedstock for animals. In addition to the benefit of increased oil content, because of the preference of these enzymes towards certain types of lipids as substrates, the resulting oil has unique fatty acid profile which is enriched in polyunsaturated fatty acids which are better for animal health than saturated fatty acids. This can be beneficial for raising healthier animals.

The plants of the disclosure may be used in a plant breeding program. The goal of plant breeding is to combine, in a single variety or hybrid, various desirable traits. For field crops, these traits may include, for example, resistance to diseases and insects, tolerance to heat and drought, tolerance to chilling or freezing, reduced time to crop maturity, greater yield and better agronomic quality. With mechanical harvesting of many crops, uniformity of plant characteristics such as germination and stand establishment, growth rate, maturity, and plant height is desirable. Traditional plant breeding is an important tool in developing new and improved commercial crops. This disclosure encompasses methods for producing a plant by crossing a first parent plant with a second parent plant wherein one or both of the parent plants is a plant displaying a phenotype as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

The development of hybrids in a plant breeding program requires, in general, the development of homozygous inbred lines, the crossing of these lines and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed plant to an elite inbred line and the resulting progeny would then comprise the transgene(s). Also, if an inbred line was used for the transformation, then the transgenic plants could be crossed to a different inbred in order to produce a transgenic hybrid plant. As used herein, "crossing" can refer to a simple X by Y cross or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly homozygous and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Plants of the present disclosure may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B) times (C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

Harvesting/Isolating Oils from Plants

In certain embodiments, the methods for accumulating oils in vegetative tissues, i.e. including TAGs, further comprise isolating the oils and TAGs produced. Several methods have been reported, and include harvesting the plants and extracting TAGs (see, for example, Christie, (1982) *Lipid Analysis*. 2nd Edition (Pergamon Press, *Oxford*); *and Kates*, (1986) Techniques of Lipidology (Elsevier, Amsterdam)). Extraction procedures include solvent extraction, and typically include disrupting cells, as by chopping, mincing, grinding, and/or sonicating, prior to solvent extraction. In one embodiment, lipids are extracted from the tissue according to the method of Bligh and Dyer (1959) (*Can J Biochem Physiol* 37: 911-917). In yet other embodiments, the TAGs are further purified, as for example by thin layer liquid chromatography (TLC), gas-liquid chromatography, counter current chromatography, high performance liquid chromatography, and the like.

EMBODIMENTS

The following numbered embodiments also form part of the present disclosure:

1. A plant, or a part thereof, that produces increased oil content in a vegetative tissue, comprising a polynucleotide encoding a phospholipase A1 (PLA1) polypeptide operatively linked to a heterologous inducible promoter functional in a plant cell.

2. The plant of embodiment 1, wherein the PLA1 polypeptide has at least 80%, at least 90%, at least 95%, at least 98%, or at least 99% sequence identity to SEQ ID NO: 1, 3, 5, 7, 9, 11, 13, 15, 17, 19, 21, 23, 25, 27, 29, 31, 33, 35,or 37.

3. The plant of embodiment 1 or embodiment 2, wherein the polynucleotide encoding the PLA1 polypeptide has at least 80%, at least 90%, at least 95%, at least 98%, or at least 99% sequence identity to SEQ ID NO: 2, 4, 6, 8, 10, 12, 14, 16, 18, 20, 22, 24, 26, 28, 30, 32, 34, 36, or 38.

4. The plant of any one of embodiments 1-3, wherein the polynucleotide encoding the PLA1 polypeptide is SEQ ID NO: 2.

5. The plant of any one of embodiments 1-4, wherein the plant produces oil in the vegetative tissue of the plant when contacted with an inducer of the promoter.

6. The plant of any one of embodiments 1-5, wherein the inducible promoter is a chemical inducible promoter, optionally wherein the chemical inducible promoter is a dexamethasone-inducible promoter or an ethanol-inducible promoter.

7. The plant of any one of embodiments 1-6, wherein the plant is of the family Brassicaceae, Fabaceae, or Solanaceae.

8. The plant of any one of embodiments 1-7, wherein the plant is not *Arabidopsis* thaliana.

9. A seed or an asexual propagate of the plant of any one of embodiments 1-8.

10. A method for increasing oil content of a vegetative tissue of a plant, the method comprising: inducibly increasing expression or activity of a phospholipase A1 (PLA1) polypeptide in the plant.

11. The method of embodiment 10, wherein the PLA1 polypeptide has at least 80%, at least 90%, at least 95%, at least 98%, or at least 99% sequence identity to SEQ ID NO: 1, 3, 5,7, 9, 11, 13, 15, 17, 19, 21, 23, 25, 27, 29, 31, 33, 35, or 37.

12. The method of embodiment 10 or embodiment 11, wherein the method comprises introducing in the plant a polynucleotide encoding the PLA1 polypeptide operatively linked to a heterologous inducible promoter functional in a plant cell, and optionally contacting the plant, or a part thereof, with an inducer of the promoter.

13. The method of embodiment 12, wherein the polynucleotide encoding the PLA1 polypeptide has at least 80%, at least 90%, at least 95%, at least 98%, or at least 99% sequence identity to SEQ ID NO: 2, 4, 6, 8, 10, 12, 14, 16, 18, 20, 22, 24, 26, 28, 30, 32, 34, 36, or 38.

14. The method of embodiment 12 or embodiment 13, wherein the polynucleotide encoding the PLA1 polypeptide is SEQ ID NO: 2.

15. The method of any one of embodiments 12-14, wherein the inducible promoter is a chemical inducible promoter, optionally wherein the chemical inducible promoter is a dexamethasone-inducible promoter or an ethanol-inducible promoter.

16. The method of any one of embodiments 10-15, wherein the plant is of the family Brassicaceae, Fabaceae, or Solanaceae.

17. The method of any one of embodiments 10-16, wherein the plant is not *Arabidopsis* thaliana.

18. A method of producing oil from a vegetative tissue of a plant, the method comprising: contacting the plant of any one of embodiments 1-8, or a part thereof, with an inducer of the promoter.

19. The method of embodiment 18, further comprising extracting oil from the plant, or the part thereof.

20. The method of embodiment 18 or embodiment 19, wherein the oil is enriched in polyunsaturated fatty acids.

21. The method of any one of embodiments 18-19, wherein the plant part is a harvested plant part.

22. A method of making a plant that produces increased oil content in a vegetative tissue, the method comprising: (a) crossing the plant of any one of embodiments 1-8 with itself or another plant to produce seed; and (b) growing a progeny plant from the seed to produce a plant that produces increased oil in a vegetative tissue.

23. The method of embodiment 22, further comprising: (c) crossing the progeny plant with itself or another plant; and (d) repeating steps (b) and (c) for an additional 0-7 generations to produce a plant that produces increased oil in a vegetative tissue.

24. A crop comprising a plurality of the plants of any one of embodiments 1-8 planted together in an agricultural field.

25. A commodity plant product prepared from the plant, plant part, or plant cell of any one of embodiments 1-8, wherein the product comprises the PLA1 polypeptide or the polynucleotide encoding the PLA1 polypeptide.

26. The commodity plant product of embodiment 25, wherein the product is fodder, seed meal, oil, or seed-treatment-coated seed.

27. A method for producing a commodity plant product, the method comprising processing the plant or plant part of any one of embodiments 1-8 to obtain the product.

28. The method of embodiment 27, wherein the product comprises the PLA1 polypeptide or the polynucleotide encoding the PLA1 polypeptide.

29. The method of embodiment 27 or embodiment 28, wherein the commodity plant product is fodder, seed meal, oil, or seed-treatment-coated seeds.

30. An expression construct comprising a polynucleotide encoding a phospholipase A1 (PLA1) polypeptide operatively linked to a heterologous inducible promoter functional in a plant cell.

31. The expression construct of embodiment 30, wherein the PLA1 polypeptide has at least 80%, at least 90%, at least 95%, or at least 99% sequence identity to SEQ ID NO: 1, 3, 5, 7, 9, 11, 13, 15, 17, 19, 21, 23, 25, 27, 29, 31, 33, 35, or 37.

32. The expression construct of embodiment 30 or embodiment 31, wherein the polynucleotide encoding the PLA1 polypeptide has at least 80%, at least 90%, at least 95%, at least 98%, or at least 99% sequence identity to SEQ ID NO: 2, 4, 6, 8, 10, 12, 14, 16, 18, 20, 22, 24, 26, 28, 30, 32, 34, 36, or 38.

33. The expression construct of any one of embodiments 30-32, wherein the PLA1 polypeptide is not SEQ ID NO: 1.

34. The expression construct of any one of embodiments 30-33, wherein the polynucleotide encoding the PLA1 polypeptide is not SEQ ID NO: 2.

35. The expression construct of any one of embodiments 30-34, wherein the inducible promoter is a chemical inducible promoter, optionally wherein the chemical inducible promoter is a dexamethasone-inducible promoter or an ethanol-inducible promoter.

36. A vector comprising the expression construct of any one of embodiments 30-35.

37. A plant or plant cell comprising the expression construct of any one of embodiments 30-35 or the vector of embodiment 36.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

Although the foregoing disclosure has been described in some detail by way of illustration and example for purposes of clarity of understanding, it will be obvious that certain changes and modifications may be practiced within the scope of the appended claims.

The following examples are offered by way of illustration and not by way of limitation.

EXAMPLES

Example 1: Initiation of Jasmonate Biosynthesis in Wounded Leaves

Terrestrial plants are subject to attacks by plant-feeding insects. The lipid-derived hormone jasmonate (JA), a collective term used to describe jasmonic acid in its precursors and derivatives, is a key phytohormone that orchestrates many of the defense responses against insects. Rapid induction of the JA-dependent signaling pathway is critical for a timely response to fast moving aggressors like insects. Indeed, judging from the speed of JA-responsive marker gene expression, the JA signaling pathway is induced within several minutes of insect herbivory or mechanical tissue injury.

The molecular details of transcriptional regulation in the JA signaling pathway have been revealed, and the centerpiece for this mechanism is a nuclear residing co-receptor complex consisting of CORONATINE INSENSITIVE 1 (COI1) and a JASMONATE ZIM-domain (JAZ) protein. COI1 is the F-box protein part of the E3 ubiquitin ligase complex, Skp1-Cull-F-box protein ($SCF^{COI1}$) and JAZs are transcriptional repressors of transcription factors (TFs) that control JA-responsive gene expression. The complex formation between COI1 and JAZ facilitated by JA results in the polyubiquitination and subsequent proteolytic degradation of JAZs which then leads to a transcriptional activation of JA-regulated genes. Since the physical interaction between COI1 and JAZ requires the bioactive form of JA, most prominently, (+)-7-iso-jasmonoyl-L-isoleucine (JA-Ile), it implies that JA must first be present for this transcriptional system to work.

The core JA biosynthetic pathway begins in the chloroplast and proceeds through the peroxisome before finally being converted to JA-Ile in the cytosol. The generally accepted first step of JA biosynthesis is the liberation of 18-carbon fatty acids (FAs) containing three double bonds (C18:3 $\Delta^{9,12,15}$) called α-linolenic acid (α-LA) from phospholipids or galactolipids in the chloroplast membrane by phospholipase A-type 1 (PLA1) lipases. DEFECTIVE IN ANTHER DEHISCENCE 1 (DAD1) (At2g44810; PLA-Iβ1) is the first established lipase to be involved in JA biosynthesis. In addition, there are seven PLA1s that group closely with DAD1 in phylogenic trees that also have predicted plastid transit peptides named DAD1-like PLA1s. Of these, DONGLE (DGL) was proposed to be the primary lipase involved in wound-induced JA biosynthesis in leaves but a subsequent study disputed the claim and instead identified PLA-Iγ1 as another contributor to JA biosynthesis in wounded leaves. Other recent studies have identified PLASTID LIPASE2 (PLIP2) and PLIP3 to be involved with ABA-induced JA biosynthesis.

Upon release from the membrane lipids by phospholipases, α-LA is converted into cis-(+)-12-oxophytodienoic acid (OPDA) by three sets of enzymes 13-LYPOXYGENASE (LOX), ALLENE OXIDE SYNTHASE (AOS) and ALLENE OXIDE CYCLASE (AOC). OPDA is further metabolized in the peroxisome by a series of enzymes, including OPDA REDUCTASE 3 (OPR3), OPC-8:0 CoA LIGASE1 (OPCL1), ACYL COA OXIDASE1/5 (ACX1/5) and other β-oxidation cycle enzymes to produce jasmonic acid. Jasmonic acid is finally conjugated to an amino acid, most prominently, isoleucine by JASMONATE RESISTANT 1 (JAR1) in the cytosol.

Although the biosynthetic pathway is relatively well characterized, the regulatory aspects of the pathway and how JA biosynthesis is initiated upon wounding remain unclear. The amount of JA in unwounded leaves can vary widely depending on developmental stage and environmental conditions but it is generally very low and only detectable by sensitive modern mass spectrometers. Wounding activates rapid de novo synthesis of JA within 2-5 min both locally and systemically. The fast timing suggests that the biosynthetic capacity (e.g., enzymes) may have already been present before wounding. However, constitutive presence of JA biosynthetic enzymes might present another problem as to why then the resting plants accumulate only a small amount of JA.

In this example, a series of physiological, pharmacological, genetic, and kinetic analyses of gene expression and hormone profiling were used to demonstrate that the early spiking of JA upon wounding does not depend on induction of JA biosynthetic gene expression. By using a transgenic system, how a decoupling between wound and JA signaling prevents perpetual synthesis of JA in wounded leaves is shown. DAD1 is used as a model lipase to demonstrate that transient activation of DAD1 transcription can trigger JA biosynthesis but that additional wound-activated post-transcriptional steps may boost DAD1-mediated JA synthesis. This boosting effect is transmissible to undamaged systemic leaves. Finally, findings about DAD1 protein stability under normal and stress conditions are reported.

Figure 1B:
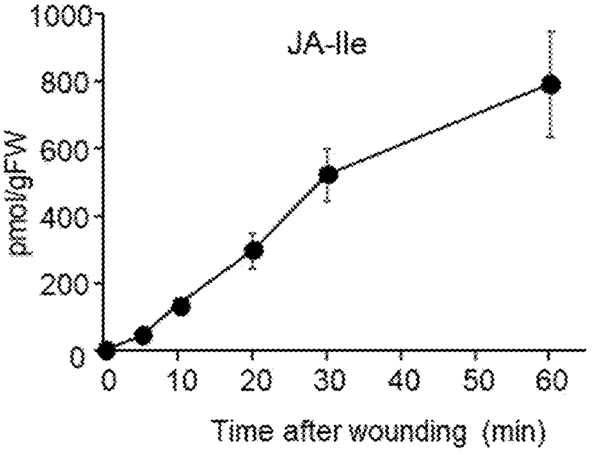
Figure 1C:
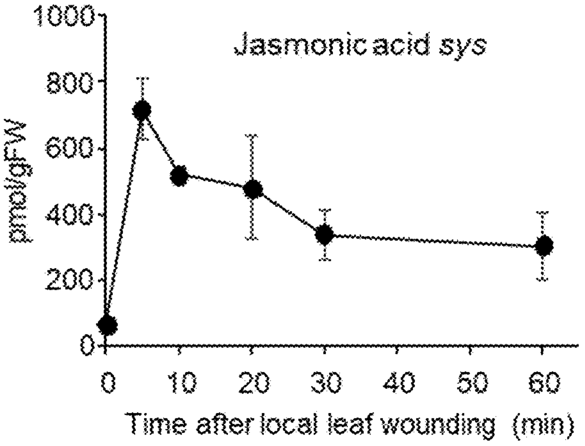
Figure 1D:
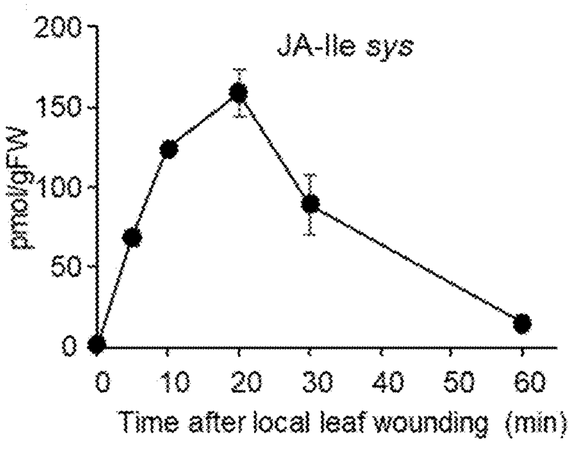

Wounding Triggers Rapid JA Biosynthesis that Precedes Transcription of JA Biosynthetic and Responsive Genes in Both Local and Systemic Leaves Mechanical wounding caused jasmonic acid and JA-Ile levels to rise linearly for about 30 min (FIG. 1A-B). Clear increases can be detected within 5 min. The level of JA before 5 min can be inferred through extrapolating a straight line through zero min, indicating that JA is made well before 5 min (FIG. 1A). There was also a rapid synthesis of jasmonic acid and JA-Ile in the systemic undamaged leaves of wounded plants within 5 min of local leaf wounding (FIG. 1C-D). The overall levels at their peaks were 5-10-fold less than that in the local damaged leaves but their increases in the systemic leaves were unmistakable. Systemic increase of both compounds could be detected within 5 min of local leaf injury consistently across all experiments.

Figure 1E:
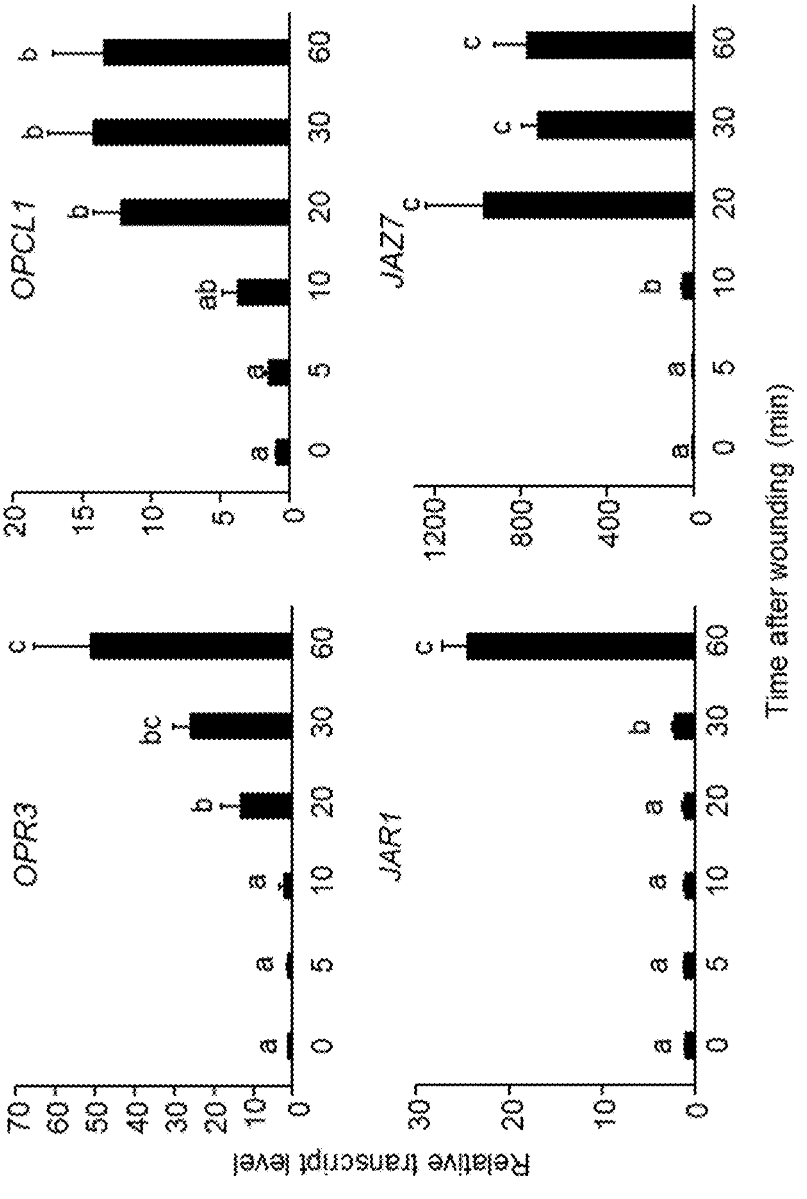
Figure 1F:
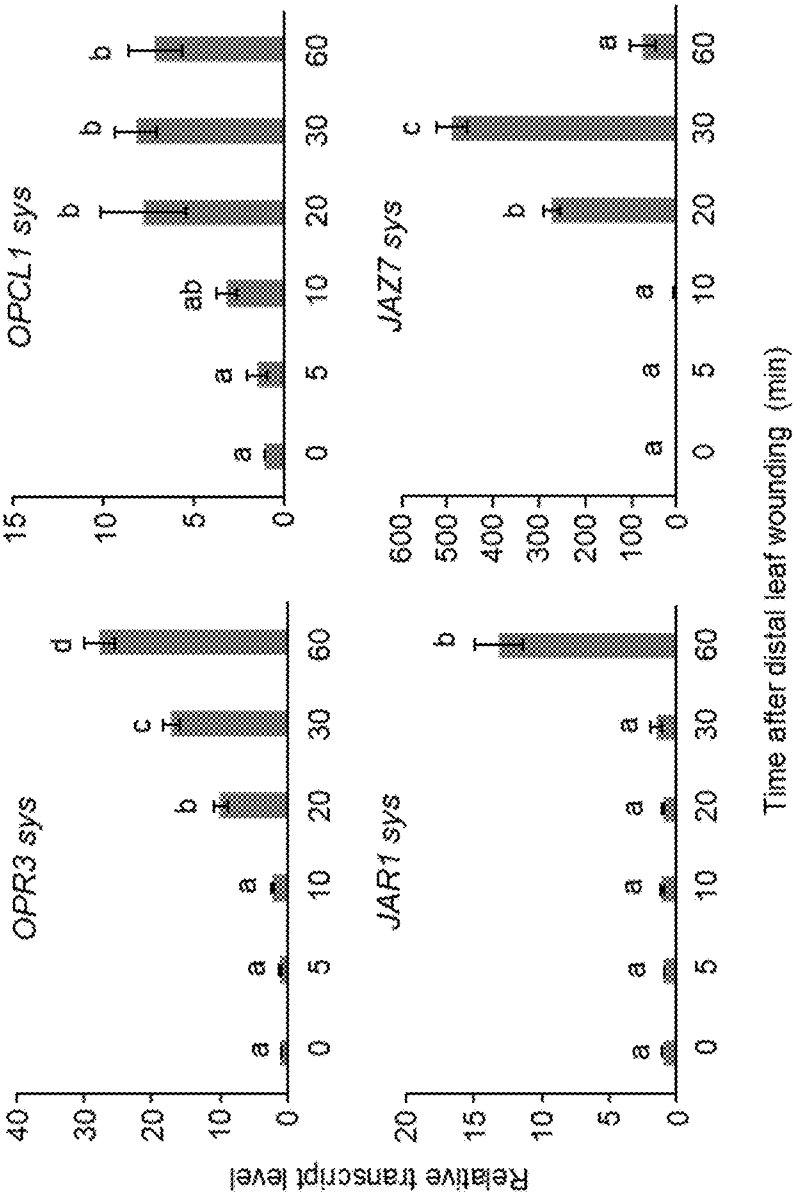

Time course gene expression analysis was carried out to see how transcription of JA biosynthetic genes and other early JA responsive genes compare with the speed of hormone accumulation. Tissue samples collected together with the above JA profiling samples were subject to semi-quantitative reverse transcriptase (qRT)-PCR analyses probing for OPR3, OPCL1 and JAZ7. JAR1 served as a late gene control. All marker genes were induced by wounding but the earliest significant increases were detected at around 10 min for OPCL1 and JAZ7, and 20 min for OPR3 (FIG. 1E). JAR1 was slowest in response and induction could not be detected until 30 min after wounding. Similar kinetic behavior of transcription was observed in the systemic leaves with increases of OPCL1sys detected the earliest among the four markers at 10 min. A clear increase of OPR3sys and JAZ7sys was detected after 20 min and JAR1sys was detected much later at 60 min (FIG. 1F). Thus, all tested marker genes lagged behind the JA increases in both the local and systemic tissues.

Figure 2A:
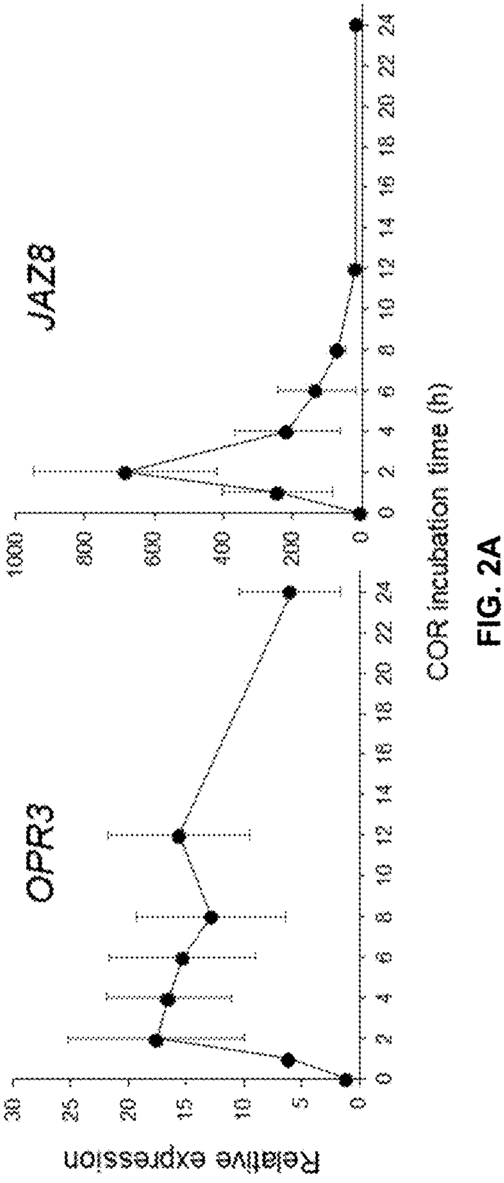
FIG. 2A-B shows coronatine (COR) is not able to elicit nor enhance wound-induced JA biosynthesis. Rosette leaves of 24-day old *Arabidopsis* leaves were evenly sprayed with mock (0.01% w/v ethanol in water) or 5 μM COR solution.
Figure 2B:
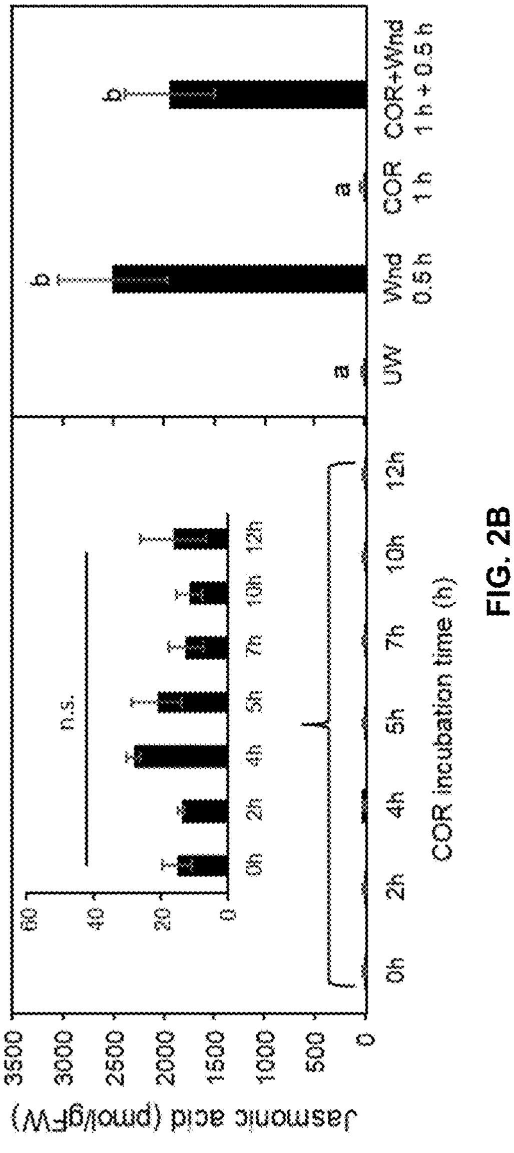

Activation or Inhibition of Gene Expression Cannot by Itself Trigger Nor Stop JA Biosynthesis Although wound-induced JA production in leaves was shown to precede the JA biosynthetic gene expression, that does not rule out the possibility that JA biosynthesis can be triggered by gene expression. To test whether JA biosynthesis can be initiated by expression of several JA biosynthetic genes, *Arabidopsis* leaves were sprayed with 5 μM coronatine (COR), a bacterial toxin and a structural mimic of JA-Ile which is known to induce JA-inducible gene expression. COR induced most, if not all, JA biosynthetic genes, including LOX2, AOS, AOC1, OPR3, OPCL1, and ACX1 as shown by an RNA-Seq experiment, as well as by time course qRT-PCR analysis of OPR3 and JAZ8 genes (FIG. 2A). Importantly, however, the same treatment did not cause jasmonic acid nor JA-Ile to increase during 12 h of COR treatment (FIG. 2B). To see if pretreatment with COR has any impact on subsequent wound-induced JA biosynthesis, plants were first sprayed with COR for 1 h and then wounded for 30 min (FIG. 2B). Wounding increased jasmonic acid in both mock and COR-treated plants but there was no additional increase of jasmonic acid levels by COR pretreatment (FIG. 2B). For JA-Ile, there was a strong reduction by COR pretreatment, which may be attributed to increased turnover because many genes involved in JA-Ile catabolism (e.g., CYP94C1, ILL6) were induced by COR.

Figure 3A:
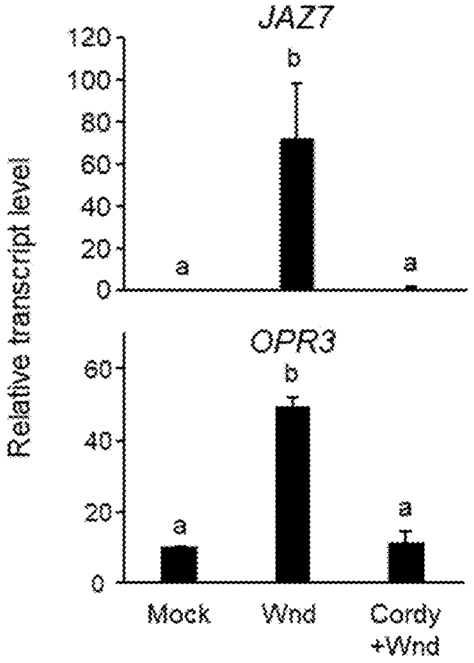
FIG. 3A-D shows inhibition of gene transcription or translation has no impact on wound-elicited JA biosynthesis.
Figure 3B:
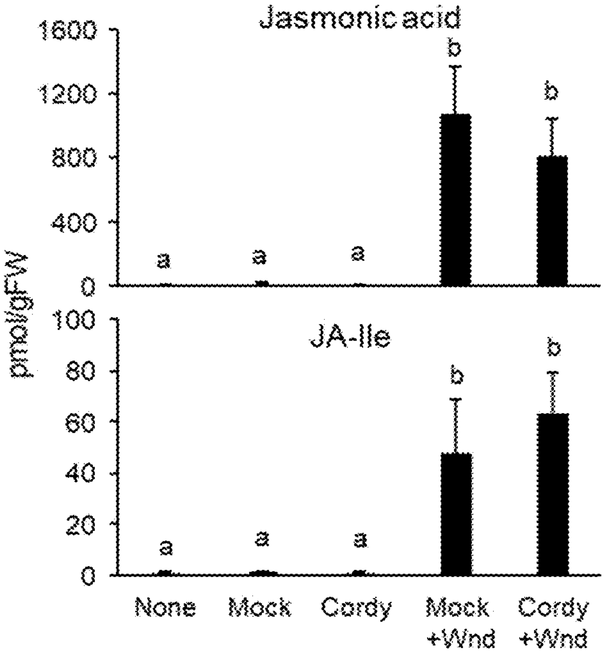

Next, whether inhibition of gene expression could affect wound-induced JA biosynthesis was tested. Plants were pretreated with 1 mM cordycepin, a potent transcriptional inhibitor for 1 h. Such treatment resulted in complete inhibition of JAZ7 and OPR3 transcription by wounding, demonstrating the efficacy of the treatment (FIG. 3A). Hormone measurement in those plants showed that cordycepin treatment alone did not cause JA levels to change compared to the mock treatment (FIG. 3B). When both the mock and cordycepin pretreated plants were wounded (1 h), there were no measurable differences in jasmonic acid or JA-Ile levels between the two groups (FIG. 3B), showing that transcriptional inhibition of JA biosynthetic genes had neither negative nor positive impacts on wound-induced JA accumulation.

Figure 3C:
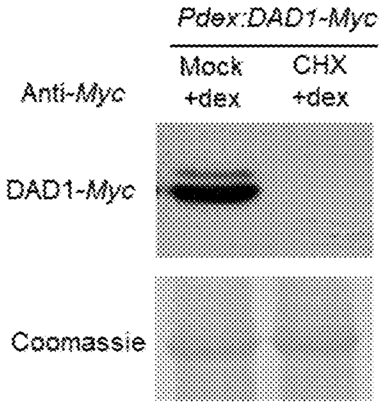
Figure 3D:
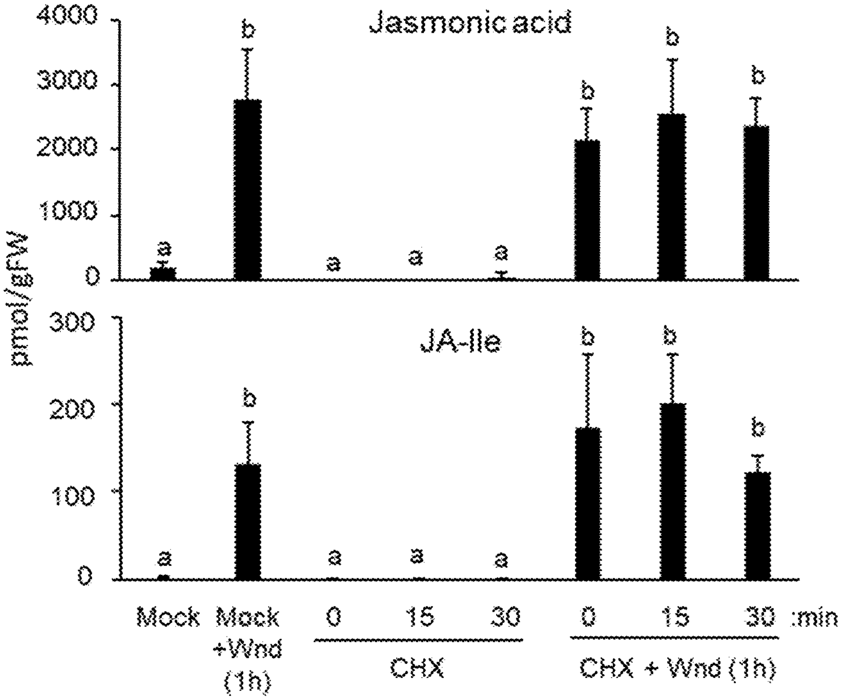

Similarly, building onto that concept, whether inhibition of protein translation could have any impact on wound-induced JA levels was tested. Plants were pre-incubated in solutions containing 0.2 mM cycloheximide (CHX) which is a potent translation inhibitor. Presence of CHX eliminated synthesis of DAD1-Myc protein in a transgenic plant (described below), demonstrating the efficacy of the treatment (FIG. 3C). CHX by itself did not change JA levels compared to mock (FIG. 3D). Importantly, wounding in the presence or absence of CHX had no impact on overall JA levels (FIG. 3D). These results show that blocking transcription or translation has no major effect on wound induced JA accumulation and that enzymes needed for initial JA production are likely to be already present.

Figure 4A:
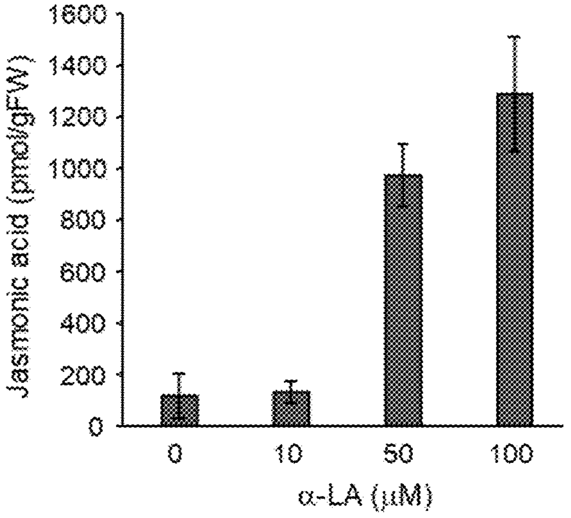
FIG. 4A-C shows JA synthesis by exogenous α-LA feeding.
Figure 4B:
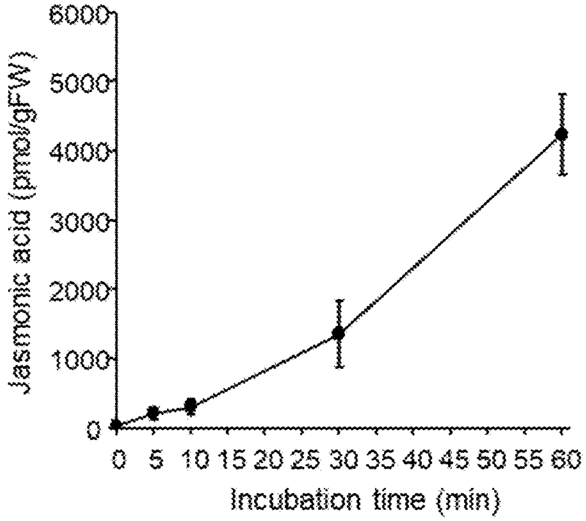

Exogenous α-LA is Converted to JAs by *Arabidopsis* Seedlings and Isolated Pea Chloroplasts The first metabolic step of JA biosynthesis is the lipolysis step that generates the FA precursor, α-LA, and earlier studies have shown α-LA conversion to JA. Intact *Arabidopsis* seedlings and a semi-in vitro system using isolated pea chloroplasts were used to study the kinetics of the α-LA conversion to JA metabolites. When *Arabidopsis* seedlings (12-d-old) were incubated in a liquid media containing 50 or 100 μM α-LA, there was a dose and time dependent increase of jasmonic acid (FIG. 4A-B). A lower concentration of 10 μM α-LA did not cause a detectable increase of jasmonic acid in the system. The time course increase was not perfectly linear but the increase was clear within 5 min of incubation which lasted until the end of our assay period of 1 h. Importantly, no other elicitation such as wounding was necessary, indicating that the biosynthetic enzymes were present and active in the seedling.

Figure 4C:
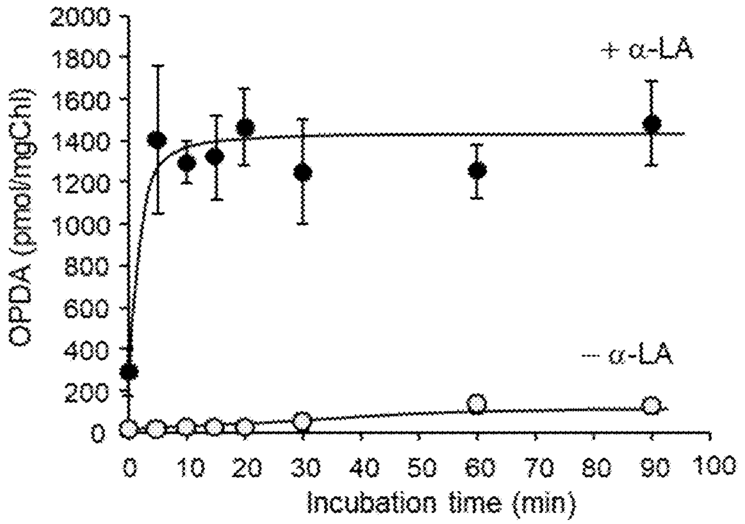

Intact chloroplasts were isolated from pea (*Pisum sativum*). Pea has been extensively used for isolating large quantities of intact chloroplasts. In the absence of exogenous α-LA, there was only a minor increase of OPDA, the final JA biosynthetic intermediate in the plastid, over the course of the 90 min incubation period (FIG. 4C). In contrast, there was a dramatic increase of OPDA to >1,200 pmol/mg chlorophyll (mgChl) that saturated within 5 min when 100 μM α-LA was added (FIG. 4C). This is a relatively large amount of OPDA compared to OPDA produced by wounded pea leaves (<50 pmol/mgChl). A trace amount of jasmonic acid (<5 pmol/mgChl) and no JA-Ile was detected in the incubation mixture. These results demonstrate that isolated chloroplasts possess all the necessary biosynthetic components to convert α-LA to OPDA and no additional elicitations are required to activate them.

Figure 5A:
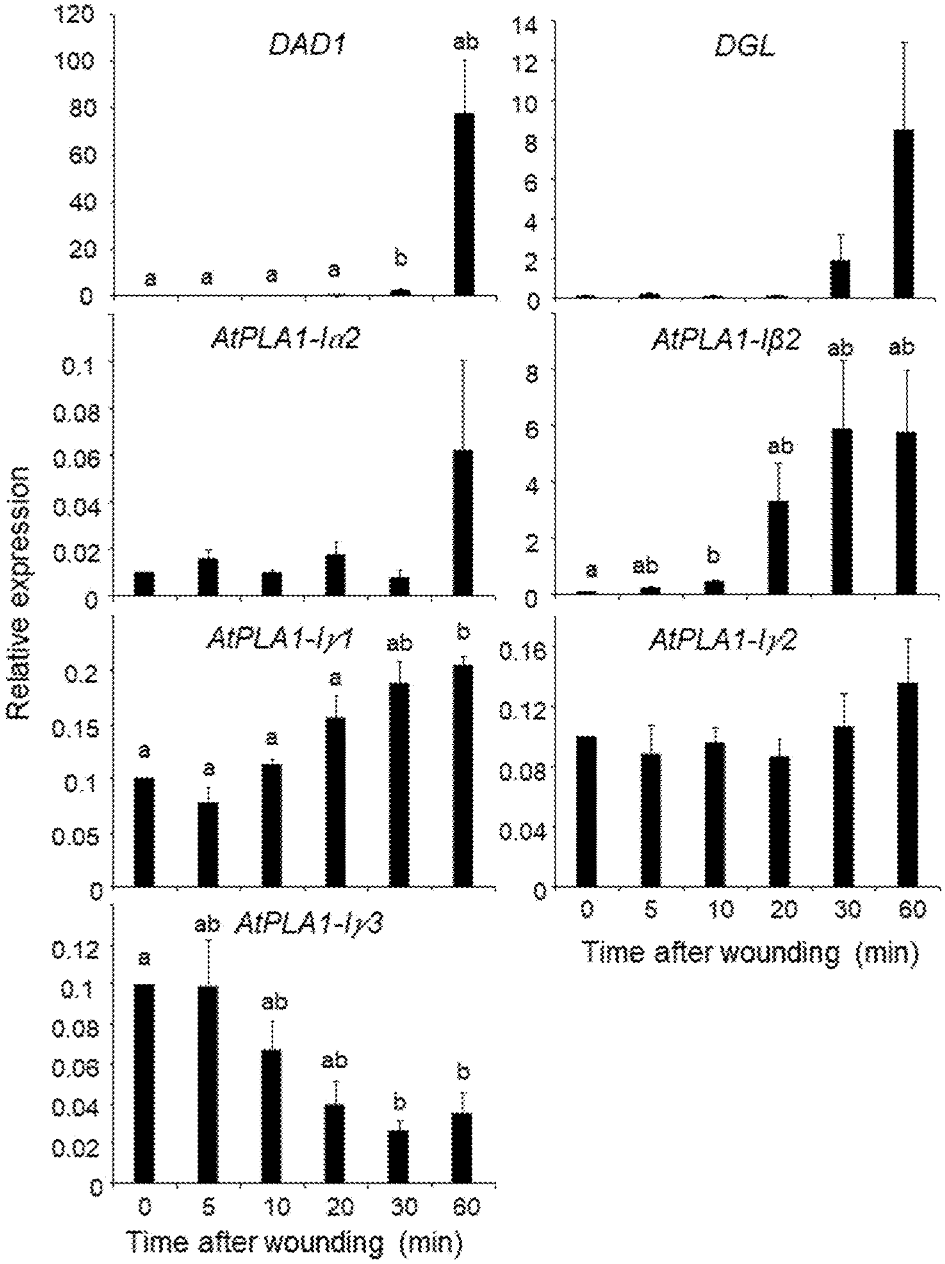
FIG. 5A-B shows expression of DAD1-like PLA1 lipases is induced by wounding but not by COR or JA.
Figure 5B:
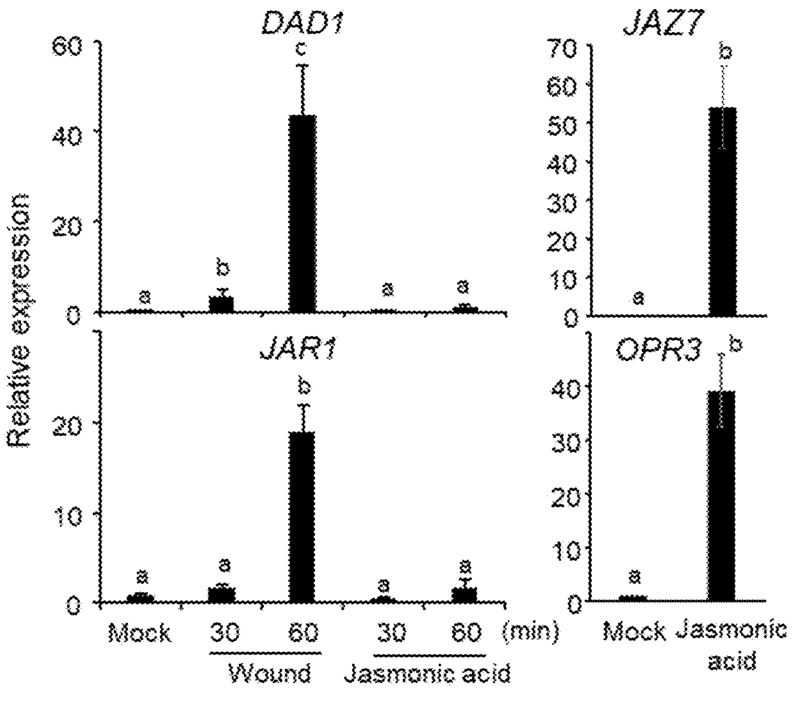

Expression of Plastidial PLA1s in Leaves is Primarily Controlled by Wounding and not by JA Feeding experiments demonstrated that providing α-LA could be a key step toward the initiation of JA biosynthesis. The most likely source of α-LA for JA biosynthesis is glycerolipids in the chloroplast membranes generated by phospholipases. Expression of seven DAD1-like PLA1s, including DAD1, DGL and PLA-1γ1 previously published for their role in JA biosynthesis were examined. Of these, five showed varying degrees of increase in transcripts upon wounding (FIG. 5A). Induction was most prominent with DAD1 followed by DGL, AtPLA1-Iα2, AtPLA1-Iβ2, and AtPLA1-Iγ1, although statistical significance was weak (p>0.05) for the latter four. Even though absolute gene-to-gene comparisons of expression levels are not accurate for this type of qRT-PCR analysis, DAD1 consistently gave the highest relative abundance followed by DGL and AtPLA1-Iβ2. Apart from their expression levels, none of the inducible transcripts were increased until 20 min post wounding which is much slower than the increase of JA. In addition, none of them were induced by COR. This is a clear difference from other JA biosynthetic genes that are strongly induced by COR. DAD1 transcripts were further tested by qRT-PCR for side-by-side comparison between wounding and jasmonic acid treatment (FIG. 5B). Wounding but not jasmonic acid caused an increase of DAD1 transcript. In addition, JAR1 was also not induced by COR nor jasmonic acid but was induced by wounding (FIG. 5B).

TABLE 2 shows RNA-seq analysis of DAD1-like PLA1s, JAR1, and OPCL1 in *Arabidopsis* seedlings sprayed with 5 μM COR. Data are from publicly available RNAseq data. Number in each cell indicates $\log_2$ of fold change over untreated 0 h. Accession numbers for genes are as follows from *Arabidopsis*.org and National Center for Biotechnology Information library, respectively. DAD1 (At2g44810, AEC10469.1); OPCL1 (At1g20510, AEE29980.1); JAR1 (At2g46370, AEC10684.1); DGL (At1g05800, AEE27895.1); AtPLA1-Iα2 (At2g31690, AEC08573.1); AtPLA1-Iβ2 (At4g16820, AEE83808.1); AtPLA1-Iγ1 (At1g06800, AEE28039.1); AtPLA1-γ2 (At2g30550, AEC08407.1); AtPLA1-Iγ3 (At1g51440, AEE32668.1).

TABLE 2

| | Time after COR treatment | | | | |
|---|---|---|---|---|---|
| Gene | 0.5 h | 1 h | 2 h | 3 h | 4 h |
| DAD1 | 0.0 | 0.3 | 0.0 | 0.0 | 0.0 |
| DGL | 0.0 | 0.0 | 0.0 | 0.0 | 0.0 |
| AtPLA1-Iα2 | 0.0 | 0.0 | 0.0 | 0.0 | 0.0 |
| AtPLA1-Iβ2 | 0.1 | 0.0 | −0.1 | 0.0 | −0.1 |
| AtPLA1-Iγ1 | 0.7 | 0.7 | 0.9 | 0.8 | 1.1 |
| AtPLA1-Iγ2 | 0.6 | 0.6 | 0.2 | −0.4 | 0.3 |
| AtPLA1-Iγ3 | −0.5 | −0.2 | 0.8 | 0.7 | 0.3 |
| OPCL1 | 5.0 | 4.4 | 4.9 | 4.8 | 4.5 |
| JAR1 | 0.3 | 0.8 | 0.0 | −0.2 | 0.0 |

Expression of DAD1-like PLA1s in the systemic leaves of wounded plants closely followed their local expression pattern, showing that the systemic wound signal can induce their expression in spite of their lack of responsiveness to JA (FIG. 1F). Similar to the local tissues, their induction took at least 20 min, again lagged far behind the systemic JA burst that happened within 5 min (FIG. 1C-D).

Figure 6A:
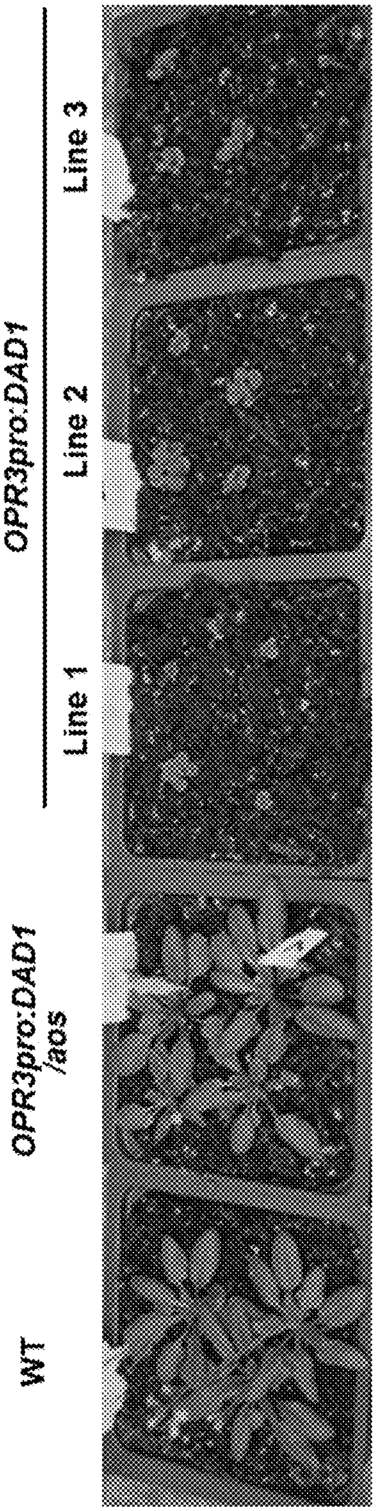
FIG. 6A-E shows DAD1 expression when controlled by JA-responsive promoter leads to constitutive production of JA in plants.
Figure 6B:
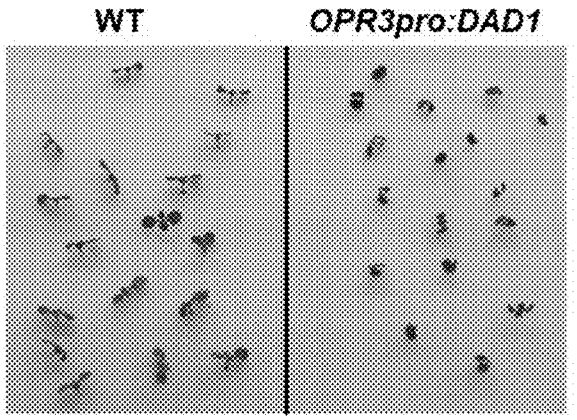
Figure 6C:
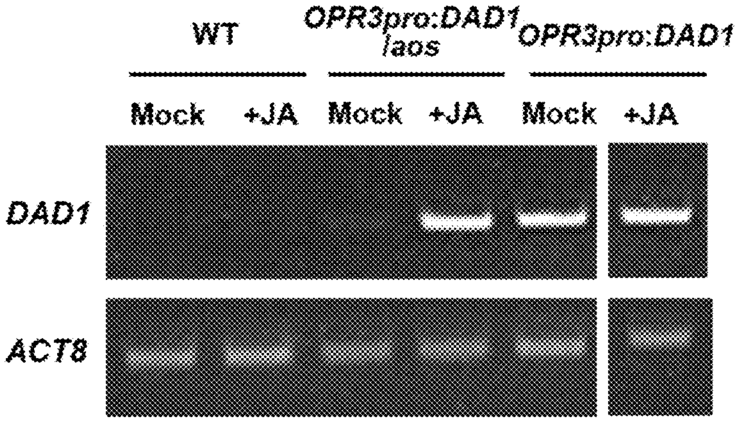
Figure 6D:
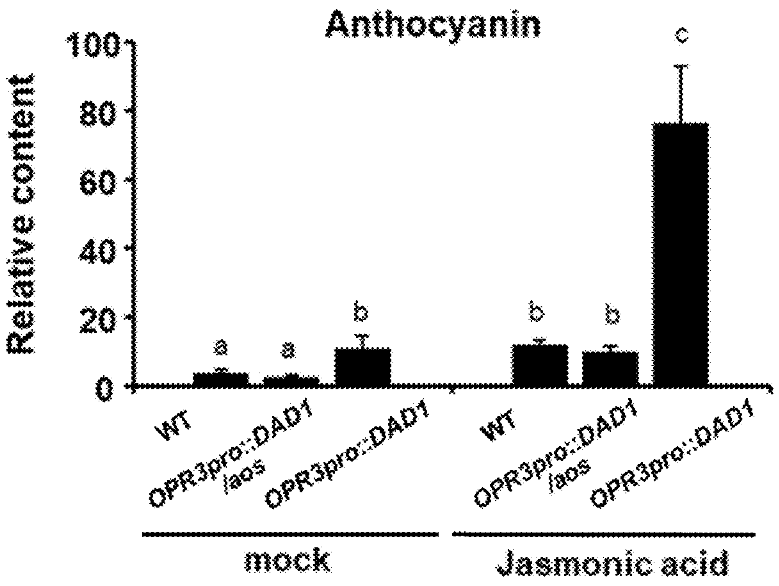
Figure 6E:
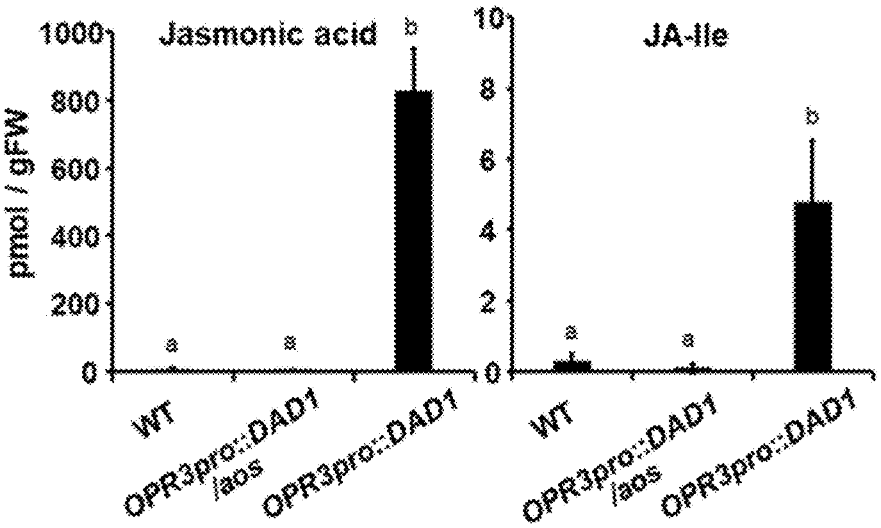

Transgenic Plants Expressing DAD1 Under JA-Inducible Promoter Display Symptoms of Chronic Exposure to JA The observation that DAD1 (and other DAD1-like PLA1s (DALLs)) gene expression can be turned on by wounding but not by JA/COR may be important for the regulation of JA biosynthesis. This is because if DAD1 expression can be activated by JA it could, in theory, create a never-ending feedback loop for perpetual JA biosynthesis following a single trigger. To test this hypothesis, an experimental "free-running" JA-lipase-JA circuit system was engineered. The idea was to generate a transgenic plant with a gene construct carrying the DAD1 gene controlled by a JA-inducible promoter. For the JA-inducible promoter, a 1.5-kb upstream region of OPR3 gene was used that had been shown to be effective in driving the expression of a reporter gene in response to exogenous JA, wounding, and insect herbivory. The resulting *Arabidopsis* lines carrying OPR3promoter: DAD1 construct (OPR3pro:DAD1) were severely stunted and accumulated anthocyanin even when grown under standard growth conditions (FIG. 6A, 6B, 6D). The phenotype is reminiscent of plants grown on JA containing media. Introduction of the same OPR3pro:DAD1 construct in the aos mutant background that is defective in JA biosynthesis suppressed the phenotype and reverted to the WT phenotype (FIG. 6A), proving that the constitutively stressed phenotypes of OPR3pro:DAD1 were due to the JA pathway. RT-PCR analysis of DAD1 transcripts showed that DAD1 was expressed at higher levels even in mock treated OPR3pro:DAD1 plants (FIG. 6C). Additive effects of the exogenous jasmonic acid on DAD1 expression in OPR3pro:DAD1 was not obvious due to the already high levels of DAD1 transcripts (FIG. 6C) but that was clear in OPR3pro:DAD1/aos plants due to the low basal level of DAD1 (FIG. 6C). The exogenous jasmonic acid treatment resulted in a substantial increase of anthocyanin in OPR3pro:DAD1 compared to equally treated WT or OPR3pro:DAD1/aos (FIG. 6D). Hormone measurements showed that OPR3pro:DAD1 plants constitutively accumulated high levels of jasmonic acid (~800 pmol/gFW) compared to WT or OPR3pro:DAD1/aos (<10 pmol/gFW) (FIG. 6E). JA-Ile levels were also higher in the OPR3pro:DAD1 plants except that its relative content compared to jasmonic acid (~0.5%) was lower than those normally observed in wounded tissues (~10%). This is likely contributed by low expression of JAR1 in unwounded JA-treated plants as shown earlier (FIG. 5C). These results demonstrate the serious negative impact that would occur if DAD1 expression was autoregulated by JA production and further shows why it is almost necessary that their promoters are responsive to wounding (or other cues) but not to JA.

Figure 7A:
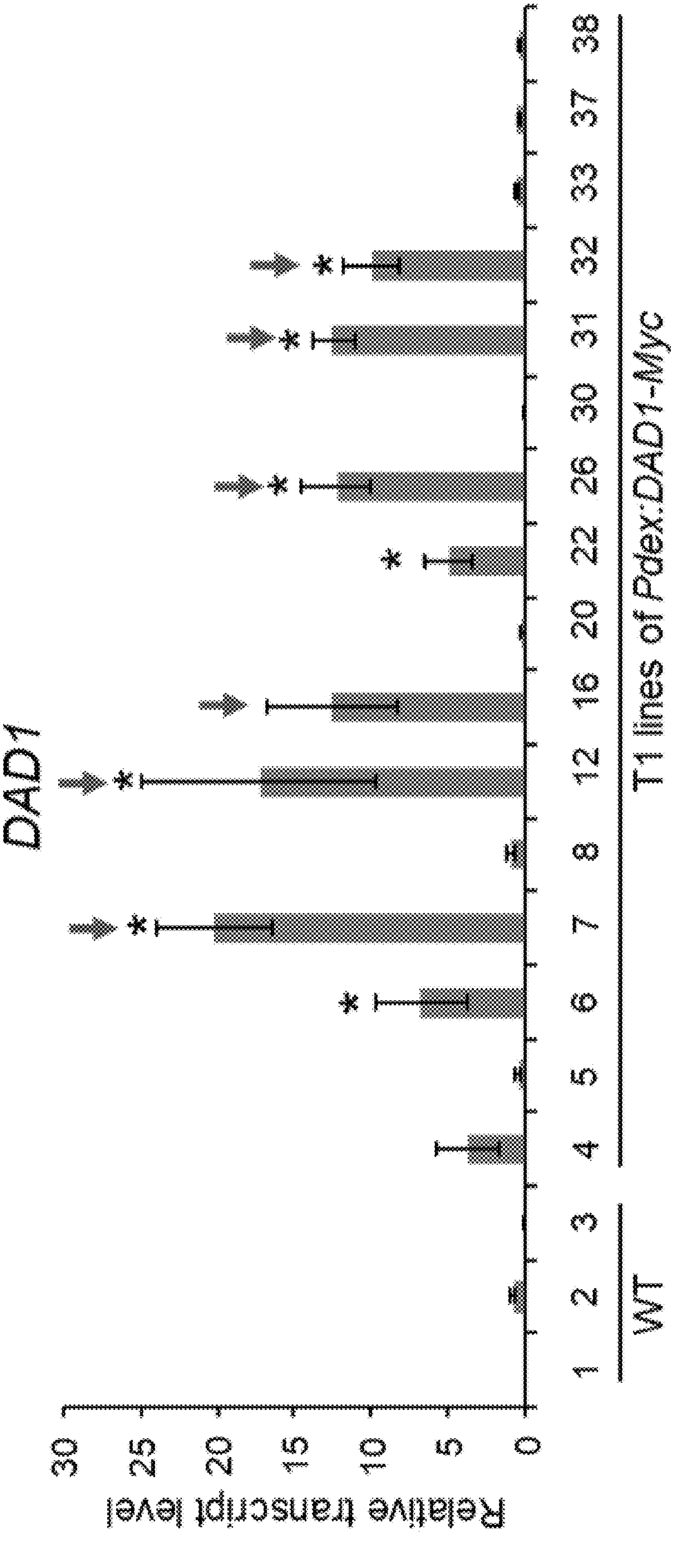
FIG. 7A-B shows establishing the Pdex:DAD1-Myc lines.
Figure 7B:
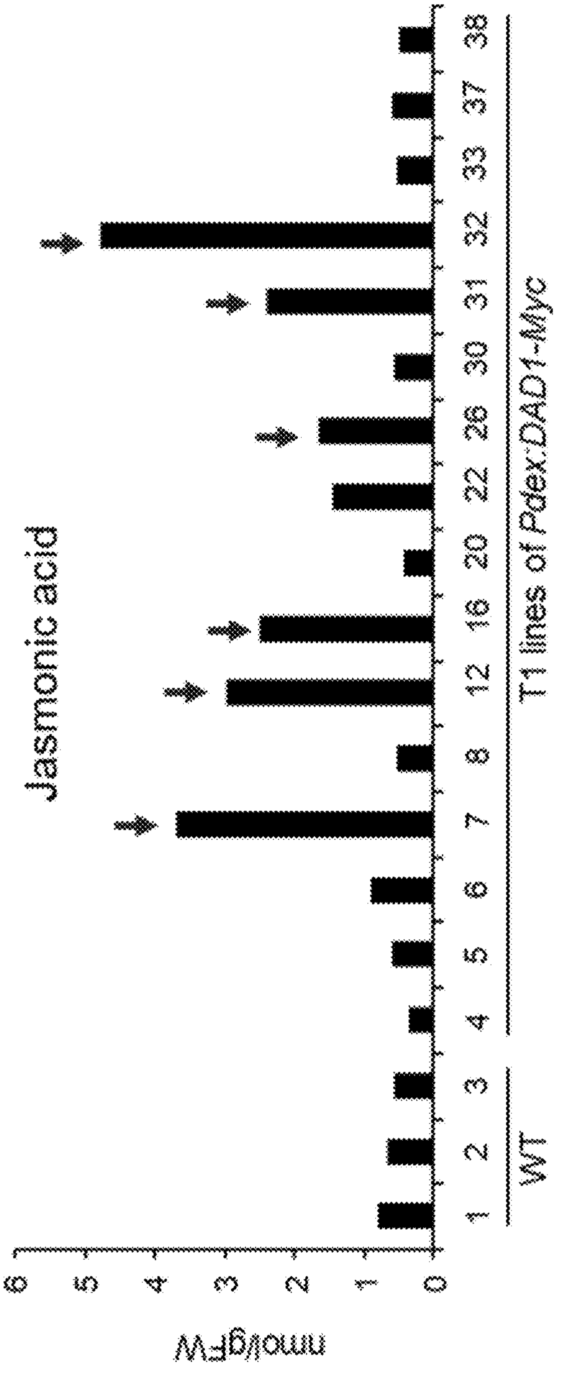

Transient Activation of DAD1 Transcription can Trigger JA Accumulation in Leaves in a Developmental Stage Dependent Manner Even though transcription of DAD1 and several other PLA1s can be activated by wounding (FIG. 5) that doesn't mean that that is how JA biosynthesis is initiated in wounded leaves. Particularly, the relatively slow induction of those transcripts both in the local and systemic leaves compared to JA production raises questions whether transcriptional activation of these lipases is sufficient to trigger JA biosynthesis. In order to test this more directly, an inducible transgenic system was created where DAD1 transcription can be ectopically induced by application of glucocorticoids that do not occur in plants (FIG. 7). Full-length DAD1 fused with aMyc epitope tag in the C-terminus was cloned into a previously described dexamethasone (dex)-inducible vector, and the resulting construct was transformed into *Arabidopsis* (Pdex:DAD1-Myc). Out of the 16 T1 plants that survived antibiotic marker selection, six lines displayed significant induction of DAD1 transcript when their leaves were treated with 30 μM of dex (FIG. 7A). Those six lines also concomitantly accumulated a substantial amount of JA (FIG. 7B). A homozygous line was selected and used for further experiments.

Figure 8A:
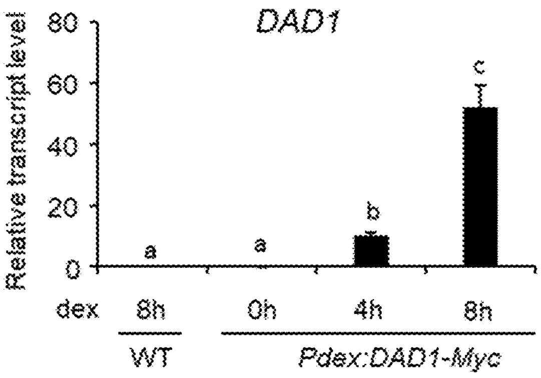
FIG. 8A-F shows ectopic expression of DAD1 can trigger JA production in a plant age-dependent manner.
Figure 8B:
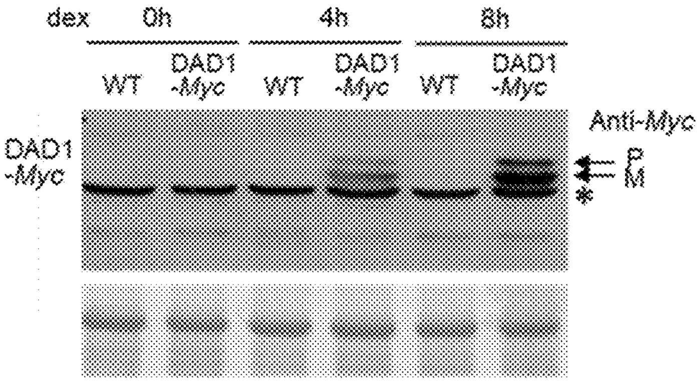
Figure 8C:
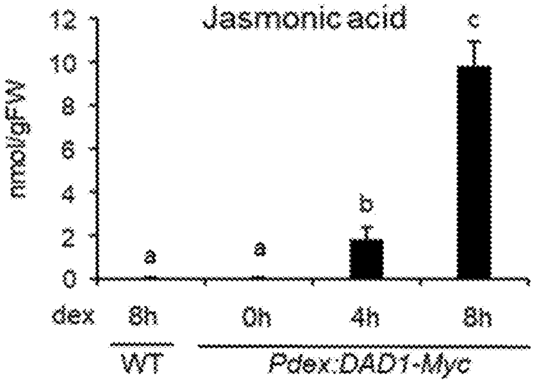

A time series experiment showed that an appreciable level of transcripts can be detected by 4 h after dex application and continued to rise 8 h post treatment (FIG. 8A). Immunodetection of DAD1-Myc using an antibody against the Myc epitope showed DAD1-Myc protein was also induced by 4 and 8 h after dex application (FIG. 8B). No DAD1-Myc protein was detected prior to the treatment with dex (0 h), showing absolute dependence of its expression on dex. Two bands that appeared to be specific to the DAD1-Myc proteins increased upon dex treatment. The upper weaker band (P) is likely to be the precursor form of DAD1-Myc before the cleavage of the chloroplast transit peptide while the stronger lower band (M) is the mature form, judging from their sizes and preferential appearance in the supernatant and the pellet, respectively, upon centrifugation. Apart from the two, a nonspecific band was detected across all samples with certain batches of commercial Myc antibodies (FIG. 8B) but not in others (FIG. 8E). Importantly, correlated with the increases of DAD1-Myc transcripts and proteins, was the increase of jasmonic acid and JA-Ile (FIG. 8C). This showed that expression of DAD1 is sufficient to trigger JA production without wounding. Similar to what had been observed with OPR3pro:DAD1, even though the increase of JA-Ile was apparent, it remained relatively low (<1% of jasmonic acid). Consistently, JAR1 proteins were not induced in these dex-treated plants in contrast to their induction by wounding.

Figure 8D:
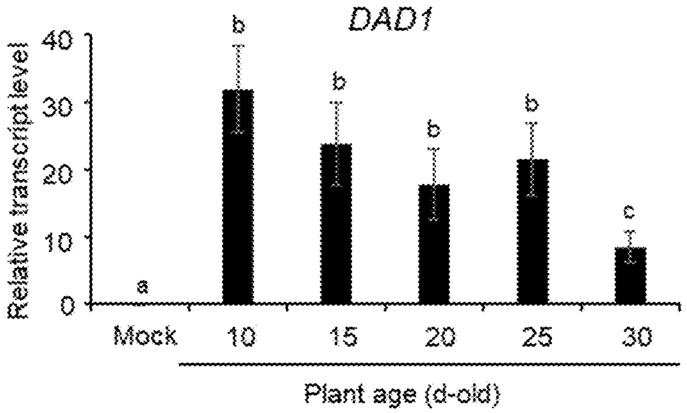
Figure 8E:
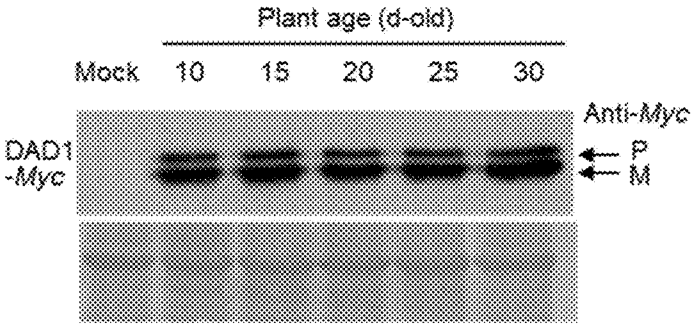
Figure 8F:
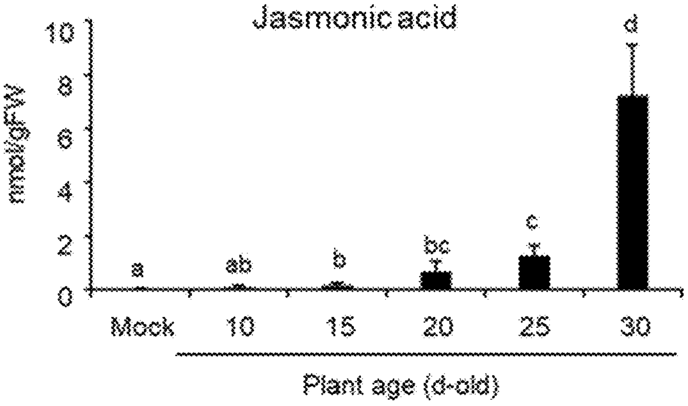

Interestingly, the ability to induce JA by dex in Pdex:DAD1-Myc was strongly dependent on the age of the plants (FIG. 8D-F). Even though transcripts and proteins of DAD1-Myc could be induced equally well by dex throughout the developmental stages from 10-d to 30-d-old plants (with the exception of DAD1 transcripts that were comparatively lower in the 30-d plants), jasmonic acid content was much lower in younger plants producing less than 0.2 nmol/gFW until reaching 15 d old (FIG. 8D-F). The levels increased to around 0.5-1 nmol/gFW after 20-d, and by 30-d there was a sudden spike of jasmonic acid levels to around 7 nmol/gFW. Earlier stage (10-15-d) plants were especially interesting because those plants contained as much DAD1 proteins as in 30-d plants (FIG. 8E) but little JA. OPDA levels in these plants were low across all stages similar to untreated WT or mock-treated Pdex:DAD1-Myc, indicating minimal, if any, metabolic bottleneck beyond OPDA in the JA biosynthetic pathway that would have contributed to the variations in the JA levels. Furthermore, those younger seedlings (12-d-old) can effectively convert exogenous α-LA to jasmonic acid (FIG. 4A-B).

Wounding can Significantly Enhance the DAD1-Induced JA Biosynthesis

Figure 9A:
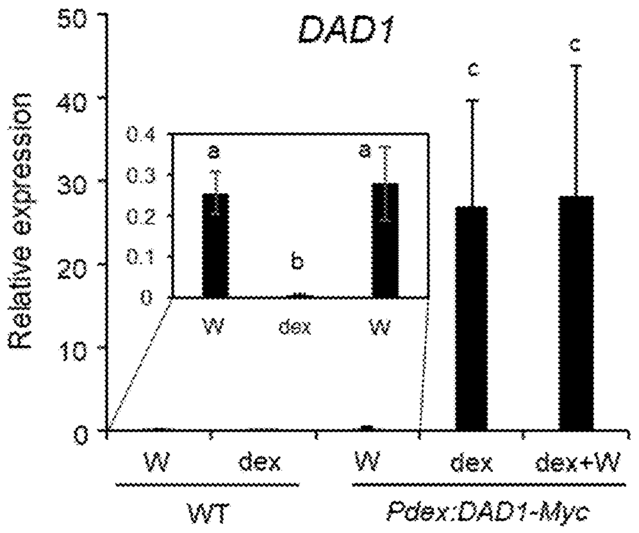
FIG. 9A-C shows wound-activated enhancement of JA synthesis by ectopic expression of DAD1-Myc.
Figure 9B:
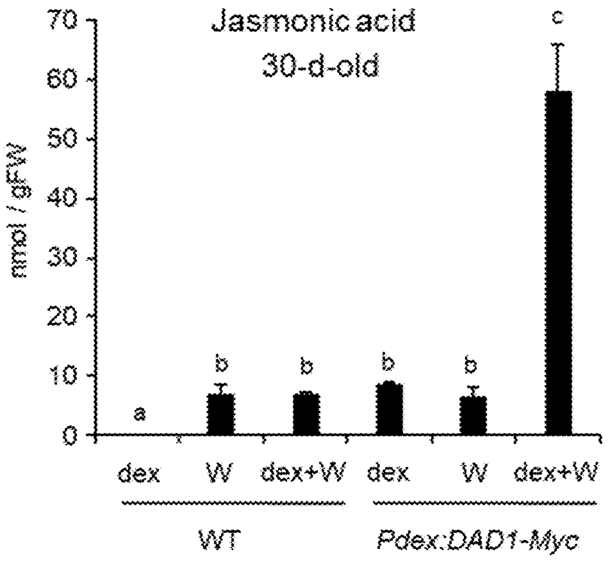
Figure 9C:
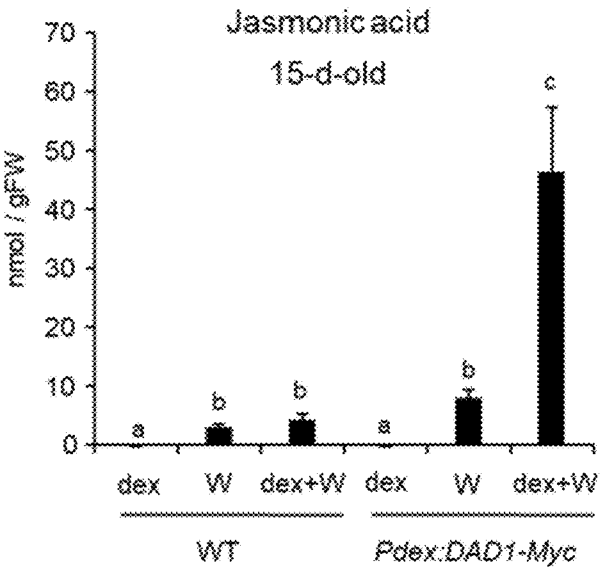

To test whether wounding has any additional effect on DAD1-induced JA biosynthesis, the Pdex:DAD1-Myc plants were subjected to either dex alone or dex plus wounding treatment (FIG. 9). As observed earlier (FIG. 5), wounding (2 h) induced endogenous DAD1 transcripts in both WT and Pdex:DAD1-Myc (no dex, 30-d-old) (FIG. 9A). Dex treatment had no effect on endogenous DAD1 level in WT but strongly induced DAD1-Myc transcripts in Pdex:DAD1-Myc. When jasmonic acid levels were measured in these plants, the singular treatments with either wounding or dex resulted in similar levels (~7 nmol/gFW) of jasmonic acid in Pdex:DAD1-Myc (FIG. 9B). These levels were equivalent to the levels reached by mechanical wounding of WT leaves (with or without dex). However, when dex and wounding were applied together to the Pdex:DAD1-Myc plants, there was >10-fold increase in jasmonic acid level (~60 nmol/gFW). Notably, the increased jasmonic level by the co-treatment was substantially higher than the simple sum of the two individual treatments (~14 nmol/gFW) (FIG. 9B), suggesting a synergistic effect between increased DAD1-Myc expression and wounding. Similar results were obtained from younger plants (15-d-old) except that the relative increase by dex+wound was even greater due to a very low jasmonic acid (~50 pmol/gFW) induction by dex-alone (FIG. 9C). The increase from near-basal-level of jasmonic acid (dex alone) to as much as 50 nmol/gFW (dex+wounding), a 1,000-fold increase, points towards an additional regulatory element that is activated by wounding besides the mere presence of more DAD1-Myc proteins.

Figure 10A:
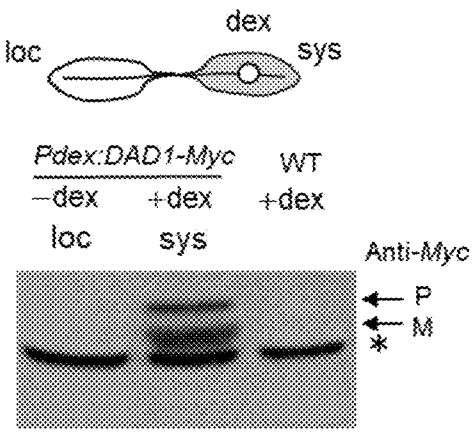
FIG. 10A-B shows boosting effects of wounding on DAD1-Myc-induced JA synthesis can be transmitted over a long distance.
Figure 10B:
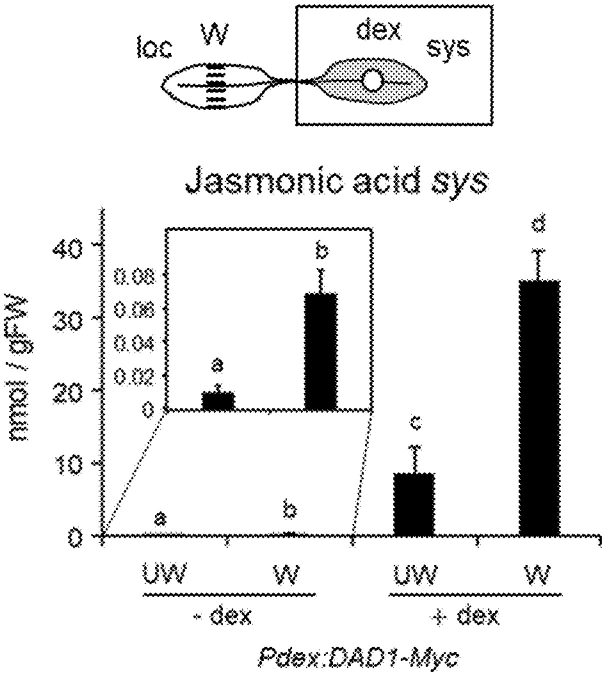

The Wound Signal that Amplifies JA Production by DAD1-Myc can be Transmitted Systemically Over a Long Distance The putative factor that boosted JA synthesis upon wounding of the DAD1-Myc-induced leaves may depend on unregulated events taking place in wounded tissues as a result of cell breakage rather than on controlled signaling events. Examples of such non-specific events include DAD1-Myc "escaping" from its natural subcellular sites and mixing with various types of membranes in a non-physiological context. This was tested by looking at the systemic undamaged leaves. DAD1-Myc expression was first induced in the systemic leaves (leaf 6 and 7) by dex for 6 h and then the untreated local leaves (leaf 3 and 4) were wounded afterwards to see if the wound signal from the local leaves would boost JA accumulation in the dex-treated systemic leaves. Systemic JA was measured after 15 min of local leaf wounding. As a control, the same experiment was carried out on Pdex:DAD1-Myc that had not been treated with dex, neither local nor systemic. As expected, DAD1-Myc protein was induced by the dex treatment of the systemic leaves but not in the local untreated leaves (FIG. 10A). Wounding of the control plants (no dex) increased systemic jasmonic acid to ~70 pmol/gFW (FIG. 10B, inset). The dex-alone induced jasmonic acid to ~7 nmol/gFW in the dex-treated systemic leaves. However, wounding of the local leaves of the plants that had their systemic leaves pretreated with dex accumulated ~35 nmol/gFW of systemic jasmonic acid (FIG. 10B), a 5-fold increase from dex alone and a 500-fold increase from wounding alone. This shows that the synergistic boosting effect triggered by wounding can happen without the need of direct cell breakage and the hypothesized random-mixing of DAD1-Myc with membranes out of physiological context.

Figure 11A:
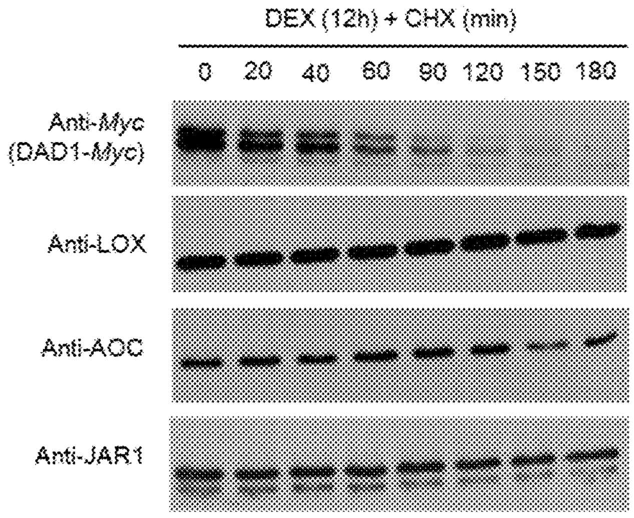
FIG. 11A-C shows DAD1 is an unstable protein whose stability is influenced by wounding or α-LA.
Figure 11B:
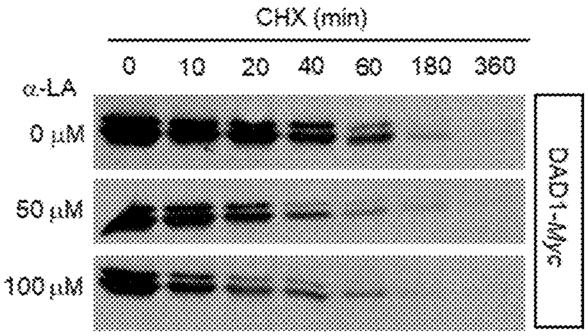
Figure 11C:
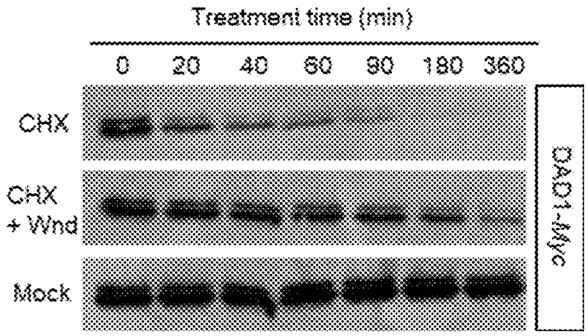

DAD1 Protein is Unstable, Stabilized by Wounding but Degrades More Quickly in the Presence of α-LA One of the potential modes of regulation for JA biosynthesis could involve the lipase itself. The dynamics of DAD1-Myc protein levels were monitored over time (FIG. 11). DAD1-Myc was induced by treating Pdex:DAD1-Myc plants with dex for 12 h, and then 0.2 mM CHX was added to inhibit protein translation. Proteins from various time points were then probed with antibodies against Myc (for DAD1-Myc), LOX, AOC and JAR1 (FIG. 11A). Interestingly, DAD1-Myc levels were markedly reduced by 1 h whereas LOX, AOC, and JAR1 remained largely unchanged; AOC levels were reduced after 3 h. Inclusion of α-LA in the incubation media further promoted the degradation of DAD1-Myc protein (FIG. 11B), resulting in a clear drop of signal by 40 min with 50 μM α-LA and 20 min with 100 μM α-LA. In contrast, wounding stabilized DAD1-Myc (FIG. 11C). DAD1-Myc levels remained strong until 90-180 min when wounded. This shows that DAD1 protein stability can be modulated by its catalytic product and wounding.

Discussion

Although transcriptional activation of JA-related genes has been extensively studied, how JA can be produced so quickly by wounding is unclear. Quick induction of the JA-pathway is important for effective defense against mobile enemies such as insects. The fast synthesis of JA by wounding cannot be easily explained by a model that depends on transcriptional activation of JA biosynthetic enzymes. The earliest detectable increase of JA biosynthetic gene transcripts by qPCR under our condition was 10 min. Induction of DAD1 and other DAD1-like PLA1s, as well as JAR1, was even slower at 20 min. Compared to this, clear increase of JA can be detected within 5 min of wounding. The faster induction of JA compared to marker transcripts was even more striking in the systemic tissues where marker genes were only beginning to increase when JA levels were already declining from their peaks.

More direct evidence against the idea that wound-triggered JA biosynthesis depends on gene expression came from the inhibitor studies in which blocking transcription or translation by cordycepin or CHX, respectively, had no major impact on JA accumulation. Conversely, induction of JA biosynthetic gene expression by COR/JA did not elicit de novo synthesis of JA, nor resulted in more synthesis of JA when wounded subsequently. The pulsed nature of wound-induced JA accumulation as opposed to a continual increase pattern (despite increasing JA in the system) is also in line with the above results that reject the presumed feedforward mechanism for JA synthesis.

At least two key JA biosynthetic steps that might prevent a run-on feedforward mechanism to be the lipid hydrolysis at the beginning of JA biosynthesis and the final conjugation step that joins nascent jasmonic acid with Ile. All seven DAD1-like PLA1s and JAR1 were exclusively expressed by wounding and not by JA/COR. The biological importance of this regulation was demonstrated by simulating the opposite situation where DAD1 expression was controlled by a JA-inducible promoter. The OPR3pro:DAD1 plants constitutively accumulated higher basal levels of JA under normal growth conditions and displayed symptoms of chronic exposure to JA such as stunted growth and pigment accumulation. The biochemical and physiological phenotypes were suppressed by aos mutation, showing that those phenotypes were due to an overactive JA pathway. This experiment clearly illustrated the problems of the perpetual synthesis of JA by autoregulation by JA. In addition, in multiple occasions, JAR1 acted as a limiting factor for larger JA-Ile increases even when jasmonic acid production was high. JA-Ile levels were 0.5% of jasmonic acid levels both in OPR3pro:DAD1 and dex-induced Pdex:DAD1-Myc. These levels are much lower compared to the typical wound response where JA-Ile levels reach 5-20% of the jasmonic acid levels or even higher (>20%) in the systemic leaves. In this way, plants seem to have spared PLA1s and JAR1 from the transcriptional JA feedforward regulatory loop and are using them as gatekeepers for JA biosynthesis in leaves.

The results showing that exogenously supplied α-LA can be converted to JA by seedlings without wounding indicate that the main limiting factor for JA biosynthesis is substrate availability. Even when the chloroplasts were isolated from the rest of the cell, they were able to convert α-LA to OPDA. This shows that the isolated chloroplasts already possess enzymes and/or other biosynthetic capacities without having to import them from the nucleus to sustain initial synthesis. In addition, similar to the intact seedlings, they do not need additional steps to activate those enzymes to carry out the reactions. This is not to say that regulatory step(s) do not exist to increase the enzymatic potential of those enzymes, but the data show that the biosynthesis will at least proceed to completion without a major hindrance. Most of the conversion by chloroplasts took place within 5 min of adding α-LA when the OPDA level plateaued. It is not clear whether this indicates complete turnover of the substrate (to OPDA and other metabolic sinks such as glycerol lipids) or active inhibition of the synthesis by the final intermediate, OPDA. Alternatively, this could indicate expiration of enzymes in need of fresh supply from the cytosol.

Transient expression of DAD1 by a dex-inducible promoter resulted in an unequivocal increase of jasmonic acid, providing evidence when DAD1 is expressed it can initiate JA biosynthesis even without wounding. The phenotypes of OPR3pro:DAD1 also supports this notion. However, other evidence paints a more complex picture to this conclusion. First, although expression of several of the DAD1-like PLA1s could be induced by wounding, their transcriptional induction lags far behind that of JA accumulation. This would indicate that there are other ways to initiate the lipolysis besides transcription.

Secondly, there was a development age-dependent aspect to the wound-free JA initiation by DAD1-Myc. Even though both the transcripts and proteins of dex-induced DAD1-Myc were at equivalent levels, the younger plants were progressively less able to accumulate jasmonic acid. This was not because younger seedlings are not capable of making JA as shown by the substrate feeding or wounding experiments. These data suggest the presence of an additional level of regulation that prevents DAD1-Myc from hydrolyzing lipids in these younger plants.

Thirdly, wounding boosted the production of JA to several fold higher than by DAD1-Myc expression alone, showing that even the mature 30-d-old Pdex:DAD1-Myc plants were not nearly at their capacity to generate JA when induced by dex alone. This synergistic boosting effect is unlikely to be contributed by other lipases that could be potentially activated by wounding together with DAD1-Myc because wounding of either WT or uninduced (no dex) Pdex:DAD1-Myc resulted in relatively low levels of JA and adding them all together with dex-only treatment would not come close to the level reached by dex+wound treatment. Thus, wounding somehow has enhanced the DAD1-Myc-mediated JA synthesis in a major way.

Fourth, the boosting of JA synthesis by wounding in dex-primed Pdex:DAD1-Myc can happen over long distances, indicating that the above-mentioned enhancement of DAD1-Myc action by wounding does not require direct breakage of cells where the recombinant DAD1 could putatively interact with other membranes in an uncontrolled manner. Rather, the systemic data show that the "boosting" effect of wounding on DAD1-Myc can be purely based on signaling processes.

Lastly, DAD1-Myc protein is more labile than other biosynthetic enzymes such as LOX, AOC or JAR1. Interestingly, its degradation could be promoted by α-LA and delayed by wounding. While this does not explain, and may not even be directly linked to, the initiation of JA biosynthesis, it shows that the DAD1 stability can be regulated and is sensitive to factors occurring during wound-induced JA biosynthesis.

Figure 12A:
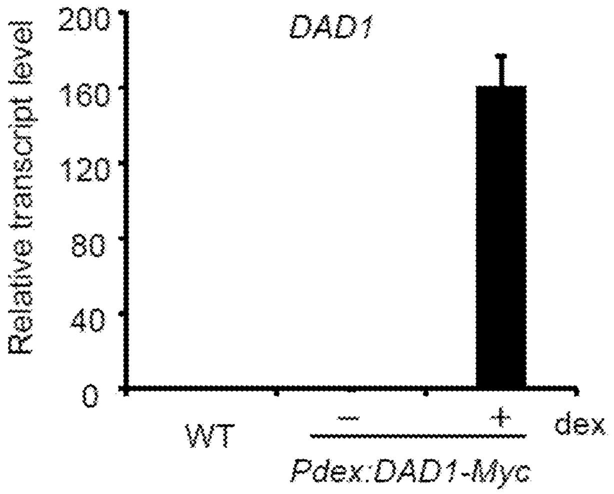
FIG. 12A-E shows ectopic expression of DAD1 in *Arabidopsis thaliana* results in triacyl glycerol (TAG) accumulation in leaves at a high level.
Figure 12B:
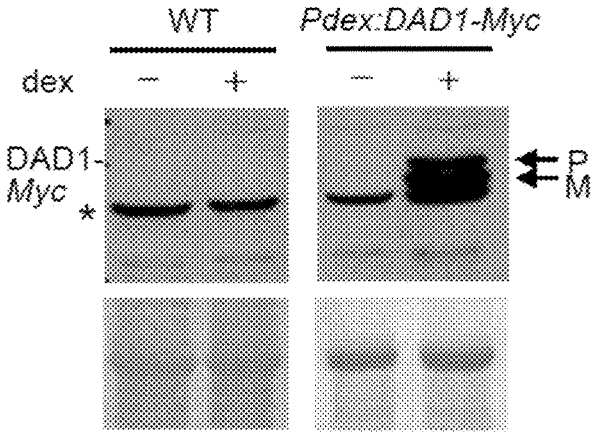
Figure 12C:
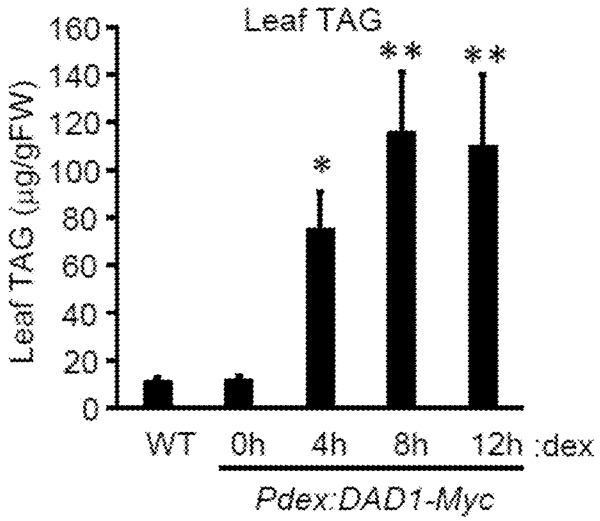
Figure 12D:
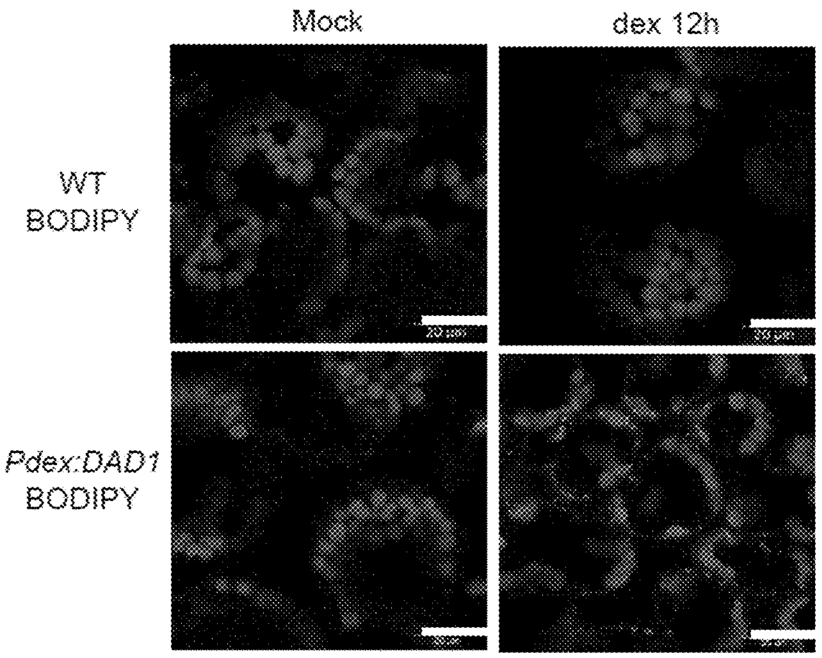
Figure 12E:
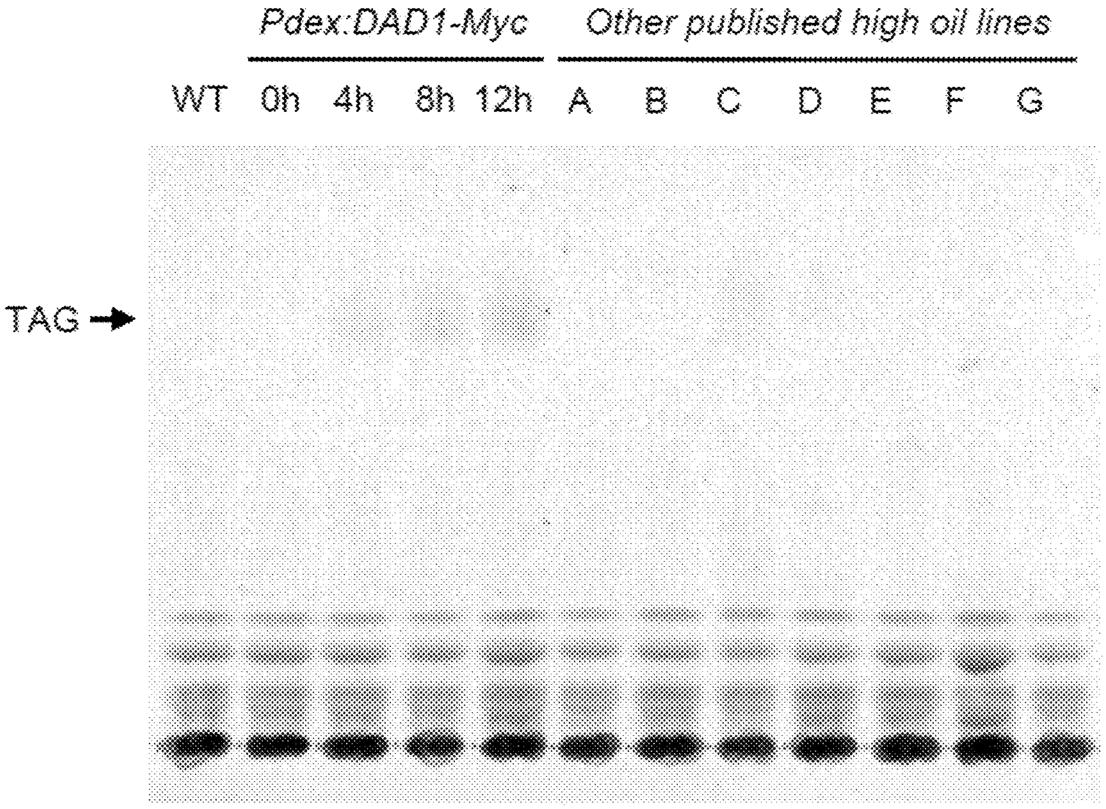

Example 2: Ectopic Expression of DAD1 in *Arabidopsis thaliana* Results in Triacyl Glycerol (TAG) Accumulation in Leaves at a High Level Ectopic expression of DAD1 (Pdex:DAD1-Myc plants) resulted in a large accumulation of triacyl glycerides or neutral lipids (oil) in vegetative tissues that normally contain very little amount of such oil. DAD1-Myc mRNA transcripts, proteins, and TAG increased over time after dex (30 μM) treatment in the Pdex:DAD1-Myc plants (FIG. 12A-C). Laser scanning confocal microscopy showed accumulation of oil bodies in leaves of dex-treated Pdex:DAD1-Myc but not wildtype (FIG. 12D). Finally, thin layer chromatography was used to compare TAG levels among dex-induced Pdex:DAD1-Myc and wildtype as well as other lines previously reported to have increased leaf TAGs including LDAP1 OE, FIT2 OE, tungDGAT2 FADX OE, tungDGAT2 OE, WRI1 OEIAGPase RNAi, WRI1 OE, and SEIPIN1 OE (FIG. 12E). Inducible expression of DAD1 increased the oil content in the leaves several fold higher than any of the other plant lines.

Figure 13A:
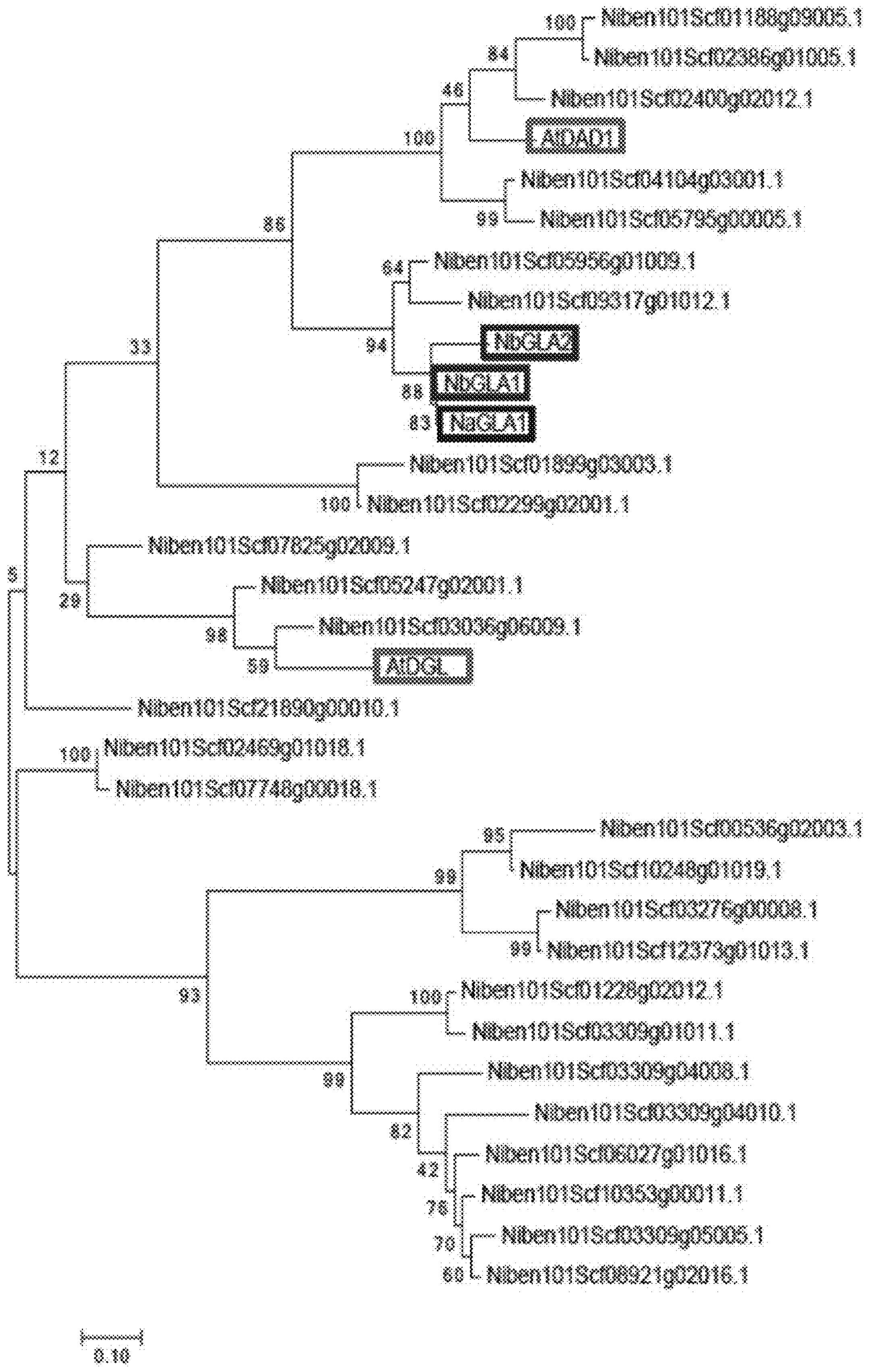
FIG. 13A-E shows NbGLA1 is the primary *N. benthamiana* lipase involved in wound-induced JA biosynthesis.
Figure 13B:
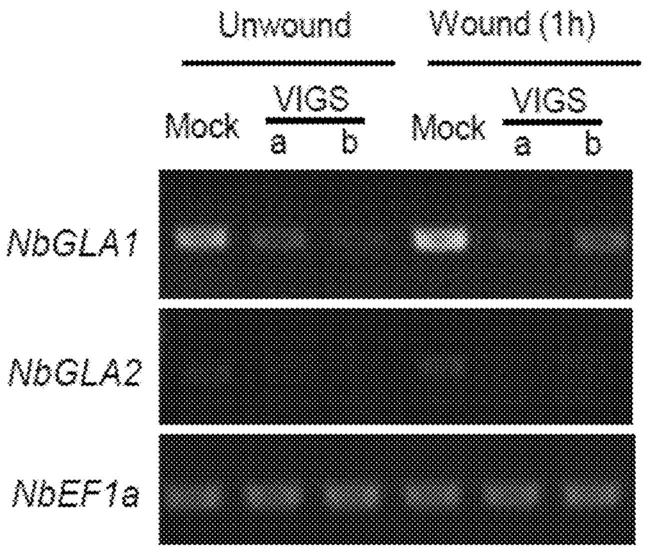
Figure 13C:
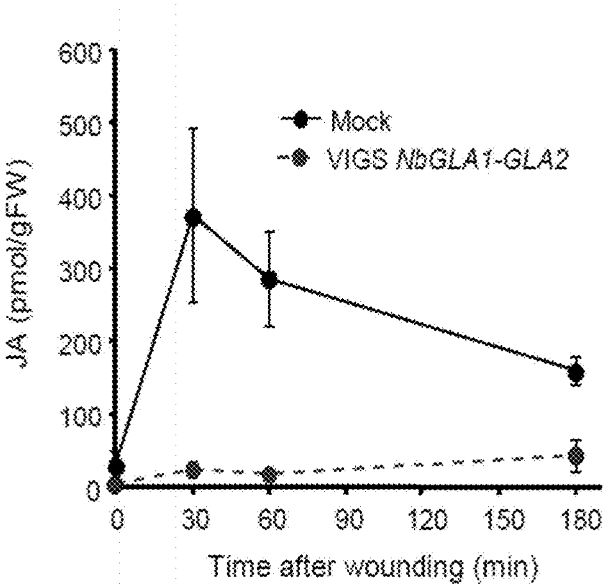
Figure 13D:
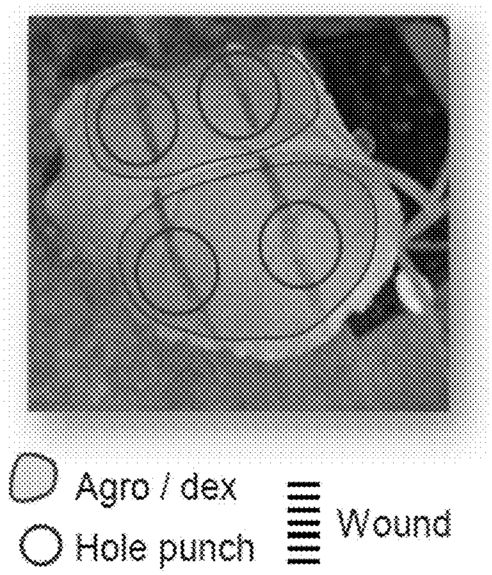
Figure 13E:
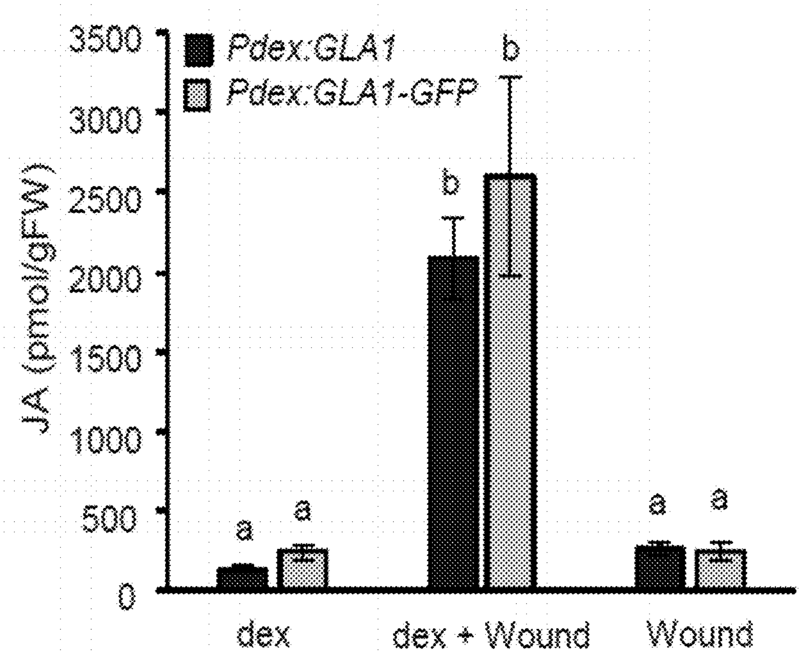

Example 3: NbGLA1 is the Primary *N. benthamiana* Lipase Involved in Wound-Induced JA Biosynthesis In this Example, the primary *N. benthamiana* lipase involved in wound-induced JA biosynthesis was identified. FIG. 13A shows phylogeny of *N. benthamiana* PLAs closely related to *N. attenuata* (Na) GLA1 and *Arabidopsis* AtDAD1 and AtDGL. NbGLA1 and NbGLA2 cluster with NaGLA1. FIG. 13B-C shows RT-PCR of NbGLA1 and NbGLA2 (FIG. 13B) and a time course of JA (FIG. 13C) in unwounded and wounded *N. benthamina* leaves infiltrated with *Agrobacterium* carrying either empty (Mock) or VIGS constructs targeting both NbGLA1 and NbGLA2. Transient expression of NbGLA1 and NbGLA1-GFP in tobacco leaves increases JA but co-treatment with wounding dramatically enhances the JA level ca.10 fold (FIG. 13D-E).

Figure 14:
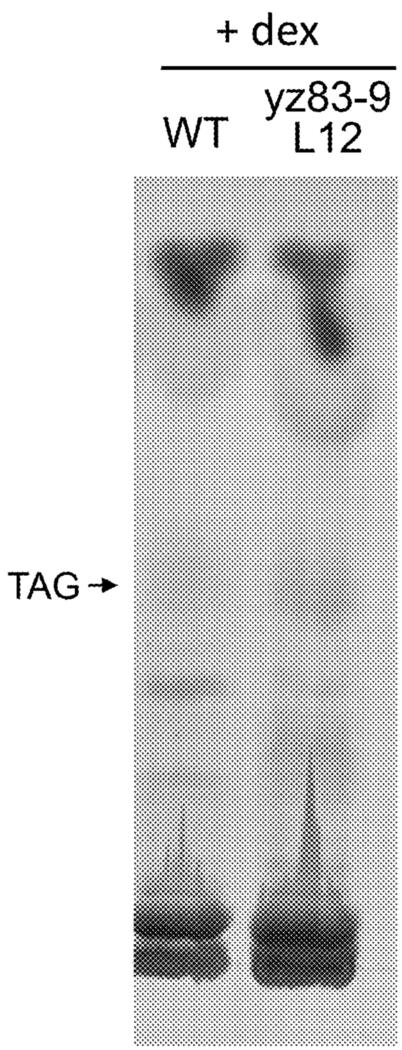
FIG. 14 is a thin layer chromatography image showing a darker triacyl glycerol band in soybean transgenic line (yz83-9 L12) compared to wildtype (WT).

Example 4: Ectopic Expression of AtDAD1 in Soybean Results in TAG Accumulation The Pdex:DAD1-Myc construct described in Example 1 was transformed into soybean. Thin layer chromatography showed a darker triacyl glycerol band in a soybean transgenic line (yz83-9 L12) compared to wildtype, which is an indicative of oil accumulation (FIG. 14). These results demonstrate the cross-species application of the DAD1 construct, which expands the potential to use the same construct in additional crops.

What is claimed is:

1. A plant, or a part thereof, that inducibly produces triacylglycerols in a vegetative tissue, comprising:

a polynucleotide encoding a phospholipase A1 (PLA1) polypeptide operatively linked to a heterologous chemical-inducible promoter functional in a plant cell, wherein the PLA1 polypeptide has at least 95% sequence identity to SEQ ID NO: 1, and wherein the plant produces triacylglycerols in the vegetative tissue of the plant when contacted with an exogenous chemical inducer of the promoter.

2. The plant of claim 1, wherein the polynucleotide encoding the PLA1 polypeptide has at least 95% sequence identity to SEQ ID NO: 2.

3. The plant of claim 1, wherein the polynucleotide encoding the PLA1 polypeptide is SEQ ID NO: 2.

4. The plant of claim 1, wherein the chemical-inducible promoter is a dexamethasone-inducible promoter.

5. The plant of claim 1, wherein the plant is of the family Brassicaceae, Fabaceae, or Solanaceae.

6. The plant of claim 1, wherein the plant is not *Arabidopsis thaliana.*

7. A seed or an asexual propagate of the plant of claim 1, wherein the seed comprises the polynucleotide encoding the PLA1 polypeptide operatively linked to the heterologous chemical-inducible promoter.

8. A method for producing the plant of claim 1, the method comprising:

introducing a polynucleotide encoding a phospholipase A1 (PLA1) polypeptide operatively linked to a heterologous chemical-inducible promoter functional in a plant cell into a plant, wherein the PLA1 polypeptide has at least 95% sequence identity to SEQ ID NO: 1.

9. The method of claim 8, wherein the polynucleotide encoding the PLA1 polypeptide has at least 95% sequence identity to SEQ ID NO: 2.

10. The method of claim 8, wherein the polynucleotide encoding the PLA1 polypeptide is SEQ ID NO: 2.

11. The method of claim 8, wherein the chemical-inducible promoter is a dexamethasone-inducible promoter.

12. The method of claim 8, further comprising contacting the plant, or a part thereof, with an exogenous chemical inducer of the promoter.

13. The method of claim 8, wherein the plant is of the family Brassicaceae, Fabaceae, or Solanaceae.

14. The method of claim 8, wherein the plant is not *Arabidopsis thaliana*.

15. A method of producing triacylglycerols from a vegetative tissue of a plant, the method comprising:

contacting the plant of claim 1, or a part thereof, with an exogenous chemical inducer of the promoter.

16. The method of claim 15, further comprising extracting triacylglycerols from the plant, or the part thereof.

17. The method of claim 15, wherein the triacylglycerols are enriched in polyunsaturated fatty acids.

18. The method of claim 15, wherein the plant part is a harvested plant part.

19. A crop comprising a plurality of the plants of claim 1 planted together in an agricultural field.

* * * * *

SEQUENCE LISTING

```
Sequence total quantity: 38
SEQ ID NO: 1           moltype = AA  length = 447
FEATURE                Location/Qualifiers
source                 1..447
                       mol_type = protein
                       organism = Arabidopsis thaliana
SEQUENCE: 1
MRFSLSPVRP HSVVVPSLPK QDVVSYISGT TSNRQCRCVL TLPSPSVSTS RPPVLPKPET   60
WESLLLNHDQ IPGEFSPTGS SIPVKLGRRW MEYQGLQNWD GLLDPLDDNL RREILRYGQF  120
VESAYQAFDF DPSSPTYGTC RFPRSTLLER SGLPNSGYRL TKNLRATSGI NLPRWIEKAP  180
SWMATQSSWI GYVAVCQDKE EISRLGRRDV VISFRGTATC LEWLENLRAT LTHLPNGPTG  240
ANLNGSNSGP MVESGFLSLY TSGVHSLRDM VREEIARLLQ SYGDEPLSVT ITGHSLGAAI  300
ATLAAYDIKT TFKRAPMVTV ISFGGPRVGN RCFRKLLEKQ GTKVLRIVNS DDVITKVPGV  360
VLENREQDNV KMTASIMPSW IQRRVEETPW VYAEIGKELR LSSRDSPHLS SINVATCHEL  420
```

```
KTYLHLVDGF VSSTCPFRET ARRVLHR                              447

SEQ ID NO: 2           moltype = DNA  length = 1344
FEATURE                Location/Qualifiers
source                 1..1344
                       mol_type = other DNA
                       organism = Arabidopsis thaliana
SEQUENCE: 2
atgagattct ctctttctcc cgtacgtccg catagtgtag tagtaccttc actaccaaaa  60
caggacgtcg tttcttatat aagtggtacg acgtcgaatc gtcaatgtcg atgtgtactt  120
acacttcctt ctccttcagt ttccacttcc cgaccaccgg ttttacccaa accggaaacc  180
tgggagagtt tgctgctaaa ccatgatcaa attccaggcg aattctcacc cactggttcg  240
agtatcccgg ttaagcttgg ccggagatgg atggagtatc aggggcttca aaattgggac  300
ggtcttttag acccattgga cgacaatctc cggcgagaga ttctccggta cggtcaattt  360
gtcgaatcgg cttatcaagc atttgatttc gatccttcct ctccaaccta cgggacatgc  420
cggtttccga ggagcacgtt gttagagcga tccggtttac ccaactccgg ttatcgacta  480
acgaagaacc ttcgtgccac gtcaggtatt aacttgccac gttggattga gaaagcgcca  540
agctggatgg ctacacaatc tagctggatt ggttacgtgg cagtttgcca ggacaaagaa  600
gagatctcgc ggcttgggcg tagagacgtc gtcatctcct tccgtggaac cgccacgtgt  660
ctcgagtggt tagagaacct tcgcgccacg ctgactcatc tccctaatgg gcctactgga  720
gcaaatctaa acgggtctaa ctctgggccc atggttgaga gcgggttttt aagcttgtat  780
acttcaggtg ttcacagttt gagagacatg gtaagagaag agatcgcaag gctactccaa  840
tcttacggcg acgagccgtt aagtgtaacg ataaccggtc acagcctcgg cgctgcgatc  900
gcgacactag cagcttacga tatcaaaacg acgtttaaac gtgcgcctat ggttaccgta  960
atatctttcg gaggtccacg tgtcggaaac agatgctttc ggaaactcct tgagaagcaa  1020
ggcacgaagg ttctaagaat cgtgaactcc gacgacgtca tcaccaaagt tcctggagtt  1080
gttttagaaa acagagagca agataacgtt aagatgacag cgtcgataat gccgagctgg  1140
atacagagac gcgtggagga gacgccgtgg gtttacgctg aaatcggtaa ggagcttcgg  1200
ctgagtagcc gtgactcgcc gcacttgagc agcatcaatg tggccacgtg tcatgagctg  1260
aaaacgtatt tacatttggt agacgggttt gtgagctcca cgtgtccatt cagagaaaca  1320
gctcggagag ttctccatag atga                                 1344

SEQ ID NO: 3           moltype = AA  length = 446
FEATURE                Location/Qualifiers
source                 1..446
                       mol_type = protein
                       organism = Brassica oleracea
SEQUENCE: 3
MRLSLSPARP YSVVPSLPNH DVVSHVNVTM SWNRKCRCVL TLSSPTISTS RSPVIPKPEM  60
WEGLLLNQDH SSGELSSYGS NNPVKLNRRW KEYQGLQNWE GLLDPLDDNL RGEILRYGQF  120
VESAYQSFDF DPSSPTYATC RFPRNTLLDQ SGLPNSGYRV TKNLRATSGI NLPRWIEKAP  180
SWMATQSSWI GYVAVCQDKD EISRLGRRDV VISFRGTATC LEWLENLRAT LTHLPDGPSG  240
PNLNGSNSGP MVESGFLSLY TSGAHSLRDM VRQEISRLLQ SYGDEPLSLT ITGHSLGAAI  300
ATLAAYDIKT TFKRAPMVTV MSFGGPRVGN RCFRRLLEKQ GTKVLRIVNS DDVITKVPGV  360
VLDNREKDNV KMTVSMPSWI QKRVEETPWV YAEVGKELRL SSRDSPYLNG INVATCHELK  420
TYLHLVDGFV SSTCPFRETA RRVLHR                               446

SEQ ID NO: 4           moltype = DNA  length = 1341
FEATURE                Location/Qualifiers
source                 1..1341
                       mol_type = other DNA
                       organism = Brassica oleracea
SEQUENCE: 4
atgagactct ctctttctcc cgcacgtccg tacagtgtag taccctcact accaaaccac  60
gacgttgttt ctcacgtaaa tgttaccatg tcgtggaacc gtaagtgcag atgcgtgctt  120
actctttctt ctcctacaat atctacttcc cggtcaccgg ttatacccaa accagaaatg  180
tgggagggtt tgcttctaaa ccaagatcat agttccggtg aattgtcgtc ctatggttcg  240
aacaacccgg ttaagctaaa ccggagatgg aaggagtacc aggggcttca gaattgggaa  300
ggtcttttag acccattgga tgataatctc cgaggggaga ttctccggta cggtcagttc  360
gtggaatcgg cttaccagtc cttcgatttc gatccttcgt caccaaccta cgcaacgtgc  420
cggttcccga ggaacacgtt gttagaccaa tccggtttac ctaactccgg ttatcgggtg  480
acgaagaacc tccgtgccac gtcaggtatt aacttaccac gttggattga gaaagcgcct  540
agctggatgg ctacacagtc cagctggatt ggttacgtgg cagtatgtca ggacaaagat  600
gagatctcac ggctcggtcg tcgagacgta gtcatctcct tccgtggcac cgccacgtgt  660
ctcgagtggt tagagaatct ccgcgccacg ctgactcatc tccctgatgg gccgagtgga  720
ccaaacctaa acgggtctaa ctctgggccc atggtcgaga gtggattctt aagcttgtac  780
acatcagggg cccacagttt gagagacatg gtaagacaag agatctcgag actgctccag  840
tcttacggcg acgagccgtt gagtttaacg ataacggggc acagtctcgg cgctgcgatc  900
gcgacgttag cggcgtacga tatcaagacg acgtttaaac gtgcgccgat ggtcaccgtt  960
atgtctttcg gaggtccacg tgtcggaaac agatgcttca ggagactcct tgagaagcaa  1020
ggcaccaagg tgttgaggat cgttaactcc gacgacgtca tcaccaaagt tccaggtgtc  1080
gttttagata accgagagaa agataacgtg aagatgacgg tgtcaatgcc gagctggata  1140
cagaaacgag tggaggagac gccgtgggtt tacgctgagg tcggcaaaga gcttcggctg  1200
agcagccgtg actctccgta cctgaacggc atcaatgttg ccacgtgtca cgagctgaag  1260
acgtatctac atttagtaga tgggtttgtt agctccacgt gtccattcag agaaacggct  1320
cgaagagtcc tccatagatg a                                    1341

SEQ ID NO: 5           moltype = AA  length = 446
FEATURE                Location/Qualifiers
```

-continued

```
source                 1..446
                       mol_type = protein
                       organism = Brassica rapa
SEQUENCE: 5
MRFSLSPARP YSVVPSLPNH DVVSHVNVTM SWNRKCRCVL TLPSPTISTS RSPVIPKPEM  60
WEGLLLNQDH SSDELSSSGS NNPVKLNRRW KEYQGLQNWE GLLDPLDDNL RGEILRYGQF  120
VESAYQSFDF DPSSPTYATC RFPRNTLLDQ SGLPNSGYRV TKNLRATSGI NLPRWIEKAP  180
SWMATQSSWI GYVAVCQDKE EISRLGRRDV VISFRGTATC LEWLENLRAT LAHLPDGPSG  240
PNLNGSNSGP MVESGFLSLY TSGAHSLRDM VREEISRLLQ SYGDEPLSLT ITGHSLGAAI  300
ATLAAYDIKT TFKRAPMVTV MSFGGPRVGN RCFRRLLEKQ GTKVLRIVNS DDVITKVPGV  360
VLDNREQDNV KMTASMPSWI QKRVEETPWV YAEVGKELRL SSRDSPYLNG INVATCHELK  420
TYLHLVDGFV SSTCPFRETA RRVLHR                                       446

SEQ ID NO: 6           moltype = DNA  length = 1341
FEATURE                Location/Qualifiers
source                 1..1341
                       mol_type = other DNA
                       organism = Brassica rapa
SEQUENCE: 6
atgagattct ctctttctcc cgcacgtccg tacagtgtag taccctcact accaaaccac  60
gacgttgttt ctcacgtaaa tgttaccatg tcgtggaacc gtaagtgtag atgcgtactt  120
actcttcctt ctcctacaat atctacttcc cggtcaccgg ttatacccaa accagaaatg  180
tgggagggtt tgctgctaaa ccaagatcac agttccgatg aattgtcgtc ctctggttcc  240
aacaacccgg ttaagctaaa ccgtagatgg aaggagtacc aggggcttca gaactgggaa  300
ggtcttttgg acccattgga cgataatctc cgaggggaga ttctccggta cggtcagttc  360
gtggaatcgg cttaccagtc cttcgatttc gatccttcgt caccaaccta cgcaacgtgc  420
cggttcccga ggaacacgtt gttagaccaa tccggtttac ctaactccgg ttatcgagtg  480
acgaagaacc tccgtgccac atcaggtatt aacttaccac gttggataga gaaagcgcct  540
agctggatgg ctacacagtc cagctggatt ggttacgtgg cagtatgtca agacaaagaa  600
gagatctcac ggctcggtcg tcgagacgta gtcatctcct tccgtggaac cgccacgtgt  660
ctcgagtggt tagagaatct ccgcgccacg ctggctcatc tccctgatgg gccgagtggg  720
ccaaacctaa acgggtctaa ctctgggccc atggtcgaga gtggattctt aagcttatac  780
acatcagggg cccacagttt gagagacatg gtgagagaag aaatctcgag actgctccag  840
tcttacggcg acgagccgtt gagtttaacg ataacggggc acagcctcgg agccgcgatc  900
gcgacgttag cggcgtacga tatcaagacg acgtttaaac gtgcgccgat ggtcaccgtt  960
atgtctttcg gaggtccacg tgtcggaaac agatgcttca ggagactcct tgagaagcaa  1020
ggcaccaagg tgttgaggat cgttaactcc gacgacgtca tcaccaaagt tccaggtgtc  1080
gttttagata acagagagca agataacgtg aagatgacgg cgtcaatgcc gagttggata  1140
cagaaacgag tggaggagac gccgtgggtt tacgccgagg tcgggaaaga gcttcggctg  1200
agcagccgtg actcgcccta cctgaacggc atcaatgtgg ccacgtgtca cgagctgaag  1260
acgtatctac atttagtaga tgggtttgtg agctccacgt gtccattcag agaaacggct  1320
cgaagagtcc tccatagatg a                                            1341

SEQ ID NO: 7           moltype = AA  length = 446
FEATURE                Location/Qualifiers
source                 1..446
                       mol_type = protein
                       organism = Brassica napus
SEQUENCE: 7
MRFSLSPARP YSVVPSLPNH DVVSHVNVTM SWNRKCRCVL TLPSPTISTS RTPVIPKPEM  60
WEGLLLNQDH SSDELSSSGS NNPVKLNRRW KEYQGLQNWE GLLDPLDDNL RGEILRYGQF  120
VESAYQSFDF DPSSPTYATC RFPRNTLLDQ SGLPNSGYRV TKNLRATSGI NLPRWIEKAP  180
SWMATQSSWI GYVAVCQDKE EISRLGRRDV VISFRGTATC LEWLENLRAT LTHLPDGPSG  240
PNLNGSNSGP MVESGFLSLY TSGAHSLRDM VRQEISRLLQ SYGDEPLSLT ITGHSLGAAI  300
ATLAAYDIKT TFKRAPMVTV MSFGGPRVGN RCFRRLLEKQ GTKVLRIVNS DDVITKVPGV  360
VLDNREQDNV KMTASMPSWI QKRVEETPWV YAEVGKELRL SSRDSPYLNG INVATCHELK  420
TYLHLVDGFV SSTCPFRETA RRVLHR                                       446

SEQ ID NO: 8           moltype = DNA  length = 1341
FEATURE                Location/Qualifiers
source                 1..1341
                       mol_type = other DNA
                       organism = Brassica napus
SEQUENCE: 8
atgagattct ctctttctcc cgcacgtccg tacagtgtag taccctcact accaaaccac  60
gacgttgttt ctcacgtaaa tgttaccatg tcgtggaacc gtaagtgtag atgcgtactt  120
actcttcctt ctcctacaat atctacttcc cggacaccgg ttatacccaa accagaaatg  180
tgggagggtt tgctgctaaa ccaagatcac agttccgatg aattgtcgtc ctctggttcc  240
aacaacccgg ttaagctaaa ccgtagatgg aaggagtacc aggggcttca gaattgggaa  300
ggtctcttag acccattgga cgataatctc cgtggagaaa ttctccggta cggtcagttc  360
gtggaatcgg cttaccagtc cttcgatttc gatccttcgt caccaaccta cgcaacgtgc  420
aggttcccga ggaacacgtt gttagaccaa tccggtttac ctaactccgg ttatcgagtg  480
acgaagaacc tccgtgccac gtcaggtatt aacttaccac gttggataga gaaagcgcct  540
agctggatgg ctacacagtc cagctggatt ggttacgtgg cagtatgtca agacaaagaa  600
gagatctcaa ggctcggtcg tagagacgta gtcatctcct tccgtggaac cgccacgtgt  660
ctcgagtggt tagagaatct ccgcgccacg ctgactcatc tccctgatgg gccgagtggg  720
ccaaacctaa acgggtctaa ctctgggccc atggtcgaga gtggattctt aagcttatac  780
acatcagggg cccacagttt gagagacatg gtaagacaag agatatcgag actgctccag  840
tcttacggcg acgagccgtt gagtttaacg ataacggggc acagcctcgg cgccgcgatc  900
```

-continued

```
gcgacgttag cggcgtacga tatcaagacg acgtttaaac gtgcgccgat ggtcaccgtt  960
atgtctttcg gaggtccacg tgtcggaaac agatgcttca ggagactcct tgagaagcaa  1020
ggcaccaagg tgttgaggat cgttaactcc gacgacgtca tcaccaaagt tccaggtgtc  1080
gttttagata acagagagca agataacgtg aagatgacgg cgtcaatgcc gagttggata  1140
cagaaacgag ttgaggagac gccgtgggtt tacgctgagg tcgggaaaga gcttcggctg  1200
agcagccgtg actcgcccta cctgaacggc atcaatgtgg ccacgtgtca cgagctgaag  1260
acgtatctac atttagtaga tgggtttgtg agctccacgt gtccattcag agaaacggct  1320
cgaagagtcc tccatagatg a                                            1341

SEQ ID NO: 9           moltype = AA  length = 450
FEATURE                Location/Qualifiers
source                 1..450
                       mol_type = protein
                       organism = Camelina sativa
SEQUENCE: 9
MRLSFSPIRP HSVVTPSLPK HDAVSYINGT TSNRQCRCVL TLPSPTISTS RPPVIPKPET  60
WESLLLNQDQ ISSESSPSGS NFPVKLGRRW MEYQGLQNWD GLLDPLDDNL RREILRYGQF  120
VESAYQAFDF DPSSPTYATC RFPRSTLLDR SGLPNSGYRL TKNLRATSGI NLPRWIEKAP  180
SWMATQSSWI GYVAVCQDKE EISRLGRRDV VISFRGTATC LEWLENLRAT LTHLPNGPTG  240
PNLNGSNSGP MVESGFLSLY SSGAHSLRDM VREEISRLLQ SYGDEPLSIT ITGHSLGAAI  300
ATLAAYDIKT TFKRAPMVTV ISFGGPRVGN RCFRKLLEKQ GTKVLRIVNS DDVITKVPGV  360
VLDNREQDNV KMSSSAASAM PSWIQRRVEE TPWVYAEVGK ELRLSSRDSP YLSRINVATC  420
HELKTYLHLV DGFVSSTCPF RETARRVLHR                                   450

SEQ ID NO: 10          moltype = DNA  length = 1353
FEATURE                Location/Qualifiers
source                 1..1353
                       mol_type = other DNA
                       organism = Camelina sativa
SEQUENCE: 10
atgagattat ctttttctcc catacgtccg catagtgtag tgacgccttc actaccaaaa  60
cacgacgctg tgtcttatat aaatggtacg acgtcgaatc gtcagtgtcg atgtgtactt  120
actcttcctt ctcctacaat ctctacttcc cgaccaccgg ttatacccaa accagaaacc  180
tgggagagtt tgctactaaa ccaagatcaa atctccagcg aatcctcccc ctctggttct  240
aattttccgg ttaagcttgg ccggagatgg atggagtacc aggggcttca aaattgggat  300
ggtcttttag acccattgga cgataatctc cggcgagaga ttctccggta cggtcaattc  360
gtcgaatcgg cttaccaagc attcgatttc gatccttcgt ctcccacgta cgcgacatgc  420
cggtttccca ggagtactct gttagaccga tccggtttgc ctaattccgg ttatcgacta  480
acgaagaacc tccgtgccac gtcaggtatt aacttgccac gttggattga gaaagcgcca  540
agttggatgg ctacacaatc cagctggatt ggttacgtgg cagtttgcca agacaaagaa  600
gagatctcgc ggcttggtcg tagagacgtc gtcatctcct tccgtggaac cgccacgtgt  660
ctcgagtggt tagagaacct tcgcgcaacg ctgactcatc tccctaatgg gcccactgga  720
ccgaatctaa acgggtctaa ctctgggccc atggtcgaaa gcgggtttct aagcttgtac  780
tcttcaggtg ctcacagttt gagagacatg gtgagagaag agatctcgag gctactccaa  840
tcttacggcg acgagccgtt gagtataacc ataaccggcc acagccttgg agccgcgatc  900
gcgacactag ctgcctacga tatcaagacg acgttcaaac gtgcgcccat ggtaaccgta  960
atatccttcg gaggcccacg tgtcggaaac agatgcttca ggaaactcct tgagaagcaa  1020
ggcaccaagg ttctaagaat cgtgaactcc gatgacgtga tcaccaaagt tcctggagtc  1080
gttttagaca acagagagca agacaacgtg aagatgtcgt cgtcggcagc gtcagcaatg  1140
ccgagctgga tacagagacg cgtggaggag acgccgtggg tttacgcgga ggtcgggaag  1200
gagcttcggc tgagcagccg tgactcgccg tacttgagta gaatcaatgt ggccacgtgt  1260
cacgagctga aaacgtattt acatttggta gacgggtttg tgagctccac gtgtccattc  1320
agagagacgg ctcggagagt tctccataga tga                               1353

SEQ ID NO: 11          moltype = AA  length = 447
FEATURE                Location/Qualifiers
source                 1..447
                       mol_type = protein
                       organism = Glycine max
SEQUENCE: 11
MKFTIKTPHP LPSPQSNTLL KPRCIITTTQ TSKPTNNKNL HFSNDTRQAA LHLEKMINLE  60
EHNNYSNYFP SMQSSKLGKR WKEYHGMSNW DGLLDPLDDN LRAEILRYGH FVETVYKSFE  120
FDPSSPNYAN SRFPRKDLLE RCGLHNTGYK VTKYLRATSG IQLPSWVDKA PTWVAKQTSY  180
VGYVAVCHDK EEIKRLGRRD VVVAYRGTTT CLEWLENFRA SLTNLPIPCN TKRAFEKNGV  240
MDRSGAMVES GFLSLYTSSL PRKTFRSLQE MVRREISRIL ETYRGEQLSL TVTGHSLGAA  300
LATLTAYDVK TAFPGLPVTV ISFGGPRVGD PRFRRMLERQ GTKVLRIVNS DDVITKVPGF  360
VFDDGLASDG GVHVPGFPRW IQKRVEEAQL VYAEVGRELR LCSKDSPYLG NTNVATCHEL  420
NTYLHLVDGF VSSTCPFRAS AKRFLQR                                      447

SEQ ID NO: 12          moltype = DNA  length = 1344
FEATURE                Location/Qualifiers
source                 1..1344
                       mol_type = other DNA
                       organism = Glycine max
SEQUENCE: 12
atgaagttca caataaaaac accacaccct ctcccttcac cccaatctaa caccctcctc  60
aaacctcgct gcataataac cacaacccag acatccaaac caaccaacaa taaaaaccta  120
cacttttcta atgacacacg acaagccgca ttacatttag agaaaatgat aaacttagaa  180
gaacataata attatagcaa ttattttccg tccatgcaat catcaaaact tggcaagagg  240
```

```
tggaaggagt accatggcat gagcaattgg gacggtttgc tagacccatt agacgacaac  300
ttacgtgctg aaatcctaag atacggtcat ttcgtggaaa ccgtttacaa atccttcgag  360
tttgaccctt cttcacccaa ctatgcaaac tcgaggttcc ccagaaaaga tcttttagaa  420
cggtgtggtt tacataacac tggctacaag gtaaccaaat acctacgtgc aacctcgggt  480
attcagctac ctagttgggt ggacaaagca ccaacatggg tggcaaaaca aacgagctat  540
gttggatacg tagcggtgtg tcatgacaag gaagagatca aaaggcttgg tcggcgcgat  600
gttgtggtgg catatagagg aaccaccaca tgcttggaat ggttagagaa ttttcgtgca  660
tctctcacca acctccctat tccatgcaac accaaaaggg cctttgaaaa aaatggggtc  720
atggacagaa gtggggccat ggtggaaagc gggttcttga gtctctacac ctcatcactt  780
cccagaaaga cgtttaggtc tttacaagaa atggtgaggc gagagatttc aaggatcctc  840
gagacctacc ggggggaaca attgagtctg accgtcaccg gtcatagtct tggggcagca  900
ttagccacgc tcacggccta tgatgtcaag accgctttcc ctggactgcc ggtgacggtc  960
atctcctttg gtgggccccg cgttggggac ccgaggttcc ggaggatgct tgagaggcaa  1020
gggaccaagg tcttgcggat agtgaactcc gacgatgtca tcaccaaggt tccggggttt  1080
gtgtttgatg atggcttggc cagcgatgga ggggtccacg tgccgggatt tccgagatgg  1140
atacagaaga gggtggagga ggcacagtta gtgtatgcgg aggttgggag ggaactacgc  1200
ttatgtagca aggattctcc gtacctagga aacacgaatg ttgccacgtg tcacgagctg  1260
aacacgtatc tgcacctcgt tgatggcttt gtcagctcca cgtgtccctt cagagcctcc  1320
gcaaagaggt tcctccagcg ttga                                          1344

SEQ ID NO: 13          moltype = AA  length = 438
FEATURE                Location/Qualifiers
source                 1..438
                       mol_type = protein
                       organism = Helianthus annuus
SEQUENCE: 13
MRLIFKSPFP FKATVVPPQE PPCRWCCVVS TKTSSLTRTA RAPVKWERLL DELGETRDQT  60
APPSRLSQRW MEYHGINNWE GLLDPLDDVL RGEIIRYGSF VEAAYQSFNF DPSSPTYAAC  120
RYAKSTMLER SGVHGCGYEV TKQLHATSSI PLPRWIERMP RWMQVQSSWI GYVAVCNDKE  180
EISRLGRRDI VIALRGTITC LEWLENLRAT LTRLSGDNLS PTEQDSEPMV EAGVLSLYTS  240
GTNTCPSLQQ LLREEVLKLL KLYSDEPLSL TITGHSLGAS LAILAAYDIK TTIKHSPHLS  300
VISFGGPRVG NRSFRHHLEQ QGTKVLRIVN SDDLITKVPG FFVEDHDGVV QEENARVAHL  360
TNWIQKRVKD SRWVYANIGH ELRLSSRDSL KLNSIDVATC HDLQTYLDLV HGFVSSTCPF  420
RAGARRMLKN ATTAPSVK                                                 438

SEQ ID NO: 14          moltype = DNA  length = 1317
FEATURE                Location/Qualifiers
source                 1..1317
                       mol_type = other DNA
                       organism = Helianthus annuus
SEQUENCE: 14
atgaggctta ttttcaaatc accatttccg ttcaaagcaa cggttgtacc accacaagaa  60
ccaccgtgcc ggtggtgctg tgttgtttcc actaaaacta gtagcttaac tagaactgct  120
agagctccgg ttaaatggga aagattgcta gacgagttgg gggagactcg tgatcaaacc  180
gcgcctccga gtcgactcag ccaacggtgg atggagtacc atggtatcaa caactgggag  240
ggtttgttgg accctctaga cgacgtccta cgtggcgaga tcattcgcta cggtagcttt  300
gttgaggctg cgtaccagtc attcaacttt gatccttctt ctcctacgta cgctgcatgc  360
cggtacgcga aagtaccat gttggagcgt tccggggtgc acggatgtgg gtacgaggtg  420
acgaagcagt tacacgccac gtcatcgatt ccattgccac ggtggataga gaggatgccg  480
cgttggatgc aagtgcaatc cagctggatt ggttacgtgg cggtttgtaa tgacaaggag  540
gagatttcta ggctggggag gcgagacatt gtcattgctc tccgtggcac tatcacttgt  600
ctagagtggc tcgagaatct acgagccact ctcactcgtt tgagtggaga caatctgtct  660
ccaactgagc aagacagtga acctatggtg gaagctggag ttctgagcct gtatacctcg  720
ggcacaaata cgtgcccgag tttacaacaa ttattacggg aagaagtatt aaaattatta  780
aaattatata gtgatgagcc actgagcttg accatcactg gtcattctct aggggcttct  840
ttagccattc tagccgcgta cgacataaaa acaactatca aacactctcc ccatctctct  900
gtcatatcat ttggcggacc aagggtgggg aaccgaagct ttcgacacca cctagaacaa  960
caaggaacga aagttctacg tattgtcaac tccgatgacc taatcacaaa agttcctggt  1020
ttttttgttg aagaccatga tggtgtggta caagaggaga atgctcgcgt agcacatttg  1080
acaaactgga tacaaaagcg cgttaaagat agccgatggg tttacgctaa catagggcac  1140
gagttacgac taagtagtcg agactcgtta aagttaaaca gtattgatgt cgcaacatgt  1200
catgatctcc agacttatct tgacctggta catggttttg tgagctcgac ttgtccattt  1260
agagctggtg caagaagaat gctcaagaac gctactactg ccccttctgt aaaataa      1317

SEQ ID NO: 15          moltype = AA  length = 428
FEATURE                Location/Qualifiers
source                 1..428
                       mol_type = protein
                       organism = Phaseolus vulgaris
SEQUENCE: 15
MRTLHHAPTF IRPRCTTLLQ STKPVQKMEK MINTNMPQLR SSSSLTNKVG KKWKEYQGVN  60
NWNGLLDPLD ENLRAEILRY GQFVEAAYKS FEFDPSSPNY ATCKFPKSTH LERCGLHNTG  120
YKVTKHLRAT SGIKLPSWVD KAPSWVATQS SYIGYVAVCQ NKEEIKRLGR RDIVIAFRGT  180
TTCLEWLENL RATLTNVIPS NSTGIREAEP CSIEENGAMV ESGFLSLYTS KVSNNPSFMS  240
LQDMVRTEIA RLLKTYEGEN LSLTITGHSL GAALATLTAY DIKNSFPRPP HVTAISFGGP  300
RVGNRSFRRR LEEQGSKVLR IVNSDDVITK IPGFVFDDVE KKDGDVGGMG GAHVASFQKW  360
MRKRVEEVQW LLYSEIGEEL RLCSRDSPYL RGINIATCHD LNIYLHLVDG FVSSTCPFRA  420
TAKRFLHH                                                            428
```

```
SEQ ID NO: 16          moltype = DNA  length = 1287
FEATURE                Location/Qualifiers
source                 1..1287
                       mol_type = other DNA
                       organism = Phaseolus vulgaris
SEQUENCE: 16
atgagaactc ttcaccacgc tccaaccttc attcgaccac gctgcacaac cctccttcaa  60
tcaaccaaac ccgtacaaaa aatggagaaa atgattaaca caaacatgcc ccagttacga  120
tcatcgtcgt cattgaccaa caaagttgga aagaaatgga aggaatacca aggagtgaac  180
aattggaatg gtttgttaga ccccttggac gagaaccttc gcgccgagat tctccgctat  240
ggccaattcg ttgaggccgc gtataagtcc ttcgagttcg acccttcctc ccctaactac  300
gccacatgca agtttccaaa gagcacgcac ttggaacggt gcgggttaca caacaccggt  360
tacaaggtaa ccaaacacct acgtgcaacc tcggggatca aactacctag ttgggtggac  420
aaagcaccga gttgggtggc aacacaatca agctacattg ggtacgtagc agtgtgtcaa  480
aacaaagaag agatcaaacg actgggtcga agagacattg ttatcgcatt cagaggtacc  540
accacgtgtc ttgagtggct cgagaatctt cgagccactc tgacaaacgt gattccatct  600
aactcaactg ggatcaggga agcagagcca tgcagtattg aagaaaatgg agccatggtg  660
gaaagtgggt tcctcagttt gtacacgtca aaggtgagta acaacccttc gtttatgagc  720
ctgcaagata tggtgagaac agagattgct cgcctcctta aacttacgga aggagaaaac  780
ttgagtttga ccatcactgg gcatagtttg ggggcggcat tggcgactct aaccgcgtat  840
gacataaaaa acagttttcc ccggccaccg catgtgacgg cgatctcctt cggcggcccc  900
cgcgtgggaa accggagctt tcggcggcgg ctggaggagc aggggtctaa ggtgttgcgg  960
atagtgaact cggacgatgt tataaccaag ataccgggat ttgtgtttga tgacgtggag  1020
aaaaaagacg gtgacgtggg aggcatggga ggtgcccacg tggctagttt tcagaaatgg  1080
atgcggaagc gcgtggaaga ggtacagtgg ttgttgtact ccgagattgg ggaggagctt  1140
cgcctttgta gcagggattc tccgtacctc aggggaatca acattgccac gtgtcacgat  1200
ttgaacatct atctgcatct tgttgacggc tttgtcagtt ccacatgtcc ctttagagcc  1260
actgccaaga ggtttcttca ccattga                                     1287

SEQ ID NO: 17          moltype = AA  length = 376
FEATURE                Location/Qualifiers
source                 1..376
                       mol_type = protein
                       organism = Solanum lycopersicum
SEQUENCE: 17
MPSFSGQSPE KIGKNWMEYQ GIKNWEGLLD PLDDNLRGEI IRYGHFVEAA YRACNFDPSS  60
PSYAMCKYSR KKLFHLSGFS GTGYRISKYL KATSGINLPN WVDKAPKWMS KQSSWIGYVA  120
ICHDQREIAR LGRRDVVIAL RGTATCLEWL ENLRATLTPL PNIKHTICCP MVESGFLSLY  180
TSKIDAQQSL QDMVREEIDR IKKLYDGETL SFTIAGHSLG AALATLTAYD IKQFFRDIPL  240
VTVMSFGGPR VGNHSFRYHL DKQDTKILRI VNSDDLITKI PGFVIDNNDD DDKYVEKSDH  300
WMKRLVEDSQ WVYADVGCEL RLSSSGSPHF NGINIATCHE LNTYLHLVNS FVSSSCPVRA  360
TAKKIMHKSN NNVKCT                                                 376

SEQ ID NO: 18          moltype = DNA  length = 1131
FEATURE                Location/Qualifiers
source                 1..1131
                       mol_type = other DNA
                       organism = Solanum lycopersicum
SEQUENCE: 18
atgcctagtt tctctggaca gagcccagag aaaataggca agaattggat ggagtatcaa  60
ggaataaaga attgggaagg tctgcttgat ccactagatg ataatttacg tggagaaata  120
attcgatatg gacattttgt tgaagctgcg tacagagcat gcaattttga tccttcttct  180
ccttcatacg caatgtgcaa atactcgaga aagaaattgt ttcatctttc tggcttttcg  240
ggtactggtt atcgtatttc caagtacttg aaagctacta gtgggattaa tcttccaaat  300
tgggttgata aagctcctaa atggatgtca aagcaatcaa gttggattgg ttatgttgcg  360
atttgtcatg accaaagaga aatagcaaga ctagggagaa gagacgttgt tattgcctta  420
cgaggcacag caacttgttt agagtggctc gagaatctac gagccactct aactcctctc  480
cctaacatta aacataccat atgttgcccg atggttgaaa gtggtttcct aagtttatat  540
acatccaaaa tagacgcgca acagagtcta caagacatgg ttagagaaga aatagaccga  600
attaaaaaat tatacgatgg tgaaacttta agcttcacta tcgcaggtca ctcccttggg  660
gccgcgttag cgactctaac agcctatgat attaaacaat ttttcagaga tataccacta  720
gtaacagtca tgtcctttgg tggtccaaga gttggaaacc atagttttcg ataccatctt  780
gacaaacaag ataccaaaat tttgcgtatc gtcaactcag acgatcttat aacaaaaatt  840
cctggattcg tcattgacaa caatgacgat gatgataaat atgtggaaaa aagtgatcac  900
tggatgaaaa ggcttgtgga agatagtcaa tgggtatatg cagatgttgg atgtgagtta  960
cgtttaagta gtagtggttc accacacttt aatgggatta atattgcaac ttgtcatgaa  1020
ttaaatactt atcttcattt agttaatagt tttgttagct caagttgtcc tgttagagct  1080
actgcaaaaa aaattatgca caaaagtaac aataatgtaa aatgtacgta a          1131

SEQ ID NO: 19          moltype = AA  length = 422
FEATURE                Location/Qualifiers
source                 1..422
                       mol_type = protein
                       organism = Solanum tuberosum
SEQUENCE: 19
MIQCVTITEP ADKFTRNLSL TKNIKNIILG WINNTEPTSP NLAWMVPSFS GQSPEKLGKN  60
WMEYQGIKNW EGLLDPLDDN LRGEIIRYGH FVEAAYRACN FDPSSPSYAM CKYSRKKLFH  120
LSGFSGTGYR VSKYLKATSG IKLPNWVDKA PKWMSKQSSW IGYVAICHDQ REIARLGRRD  180
VVIALRGTAT CLEWLENLGA TLTPLPNIKH TCSTICCPMV ESGFLSLYTS KIDAQQSLQD  240
```

```
MVREEIARIK KIYDGETLSF TIAGHSLGAA LATLTAYDIK QFFRDIPLVT VMSFGGPRVG  300
NHSFRYHLDK QGTKILRIVN SDDLITKIPG FVIDNNDNKF AEKSGHWIQK LVEDSQWVYA  360
DVGCELRLSS SDSPYFNGIN IATCHELNTY LHLVNSFVSS NCPVRATAKK IMHKSNNNVK  420
CT                                                                422

SEQ ID NO: 20           moltype = DNA  length = 1269
FEATURE                 Location/Qualifiers
source                  1..1269
                        mol_type = other DNA
                        organism = Solanum tuberosum
SEQUENCE: 20
atgatccagt gtgtcaccat tactgaacca gcagataagt ttacaagaaa tttaagcctc  60
accaaaaaca tcaaaaacat cattcttggc tggattaata atactgagcc aactagtcca  120
aatttagctt ggatggtgcc tagtttctct ggacagagcc cagaaaaact aggtaagaat  180
tggatggagt atcaaggaat aaagaattgg gaaggtttgc ttgatccact agatgataat  240
ttacgtggag aaataattcg atatggacat tttgttgaag ctgcgtatag agcatgcaat  300
tttgatcctt cttctccttc atacgcaatg tgcaaatact caagaaaaaa attgtttcat  360
ctttctggct tttcaggtac tggttatcgt gtttccaagt acttgaaagc tactagtggg  420
attaagcttc caaattgggt tgataaagcg cctaaatgga tgtcaaagca atccagttgg  480
attggttatg tcgcgatttg tcatgaccaa agagaaatag caagactagg gagaagagac  540
gttgtcattg ccttacgagg cacagcaact tgtttagagt ggctcgagaa tctcggagcc  600
actctcactc ctctccctaa cattaaacat acttgttcta ccatatgttg cccaatggtc  660
gaaagtggtt tcctaagctt atatacatcc aaaatagacg cacaacagag tctacaagac  720
atggttagag aagaaatagc ccgaattaaa aaaatatacg atggtgaaac tttaagcttc  780
accatcgcag gccactccct tggggccgcg ttagccactc taacagccta cgatattaaa  840
caatttttca gagatatacc acttgtaaca gtcatgtcgt ttggtggtcc aagagtcgga  900
aaccatagtt tccgatacca tcttgataaa caaggtacca aaattttgcg tatcgtcaac  960
tcagacgatc ttataacaaa aattcctgga ttcgtcattg ataacaacga taataaattt  1020
gcggaaaaaa gcggtcattg gatccaaaag cttgtggaag atagtcaatg ggtatatgca  1080
gatgttggat gtgaactacg attaagtagt agtgattcac catactttaa tgggattaat  1140
attgcaactt gtcatgaatt aaatacttat cttcatttgg ttaatagttt tgttagctca  1200
aactgtcctg ttagagctac tgcaaaaaaa attatgcaca aaagtaacaa taatgtaaaa  1260
tgtacgtaa                                                         1269

SEQ ID NO: 21           moltype = AA  length = 405
FEATURE                 Location/Qualifiers
source                  1..405
                        mol_type = protein
                        organism = Oryza sativa
SEQUENCE: 21
MAASISGART CYPSAAVARR GGGGGRCCSV VRSSLATSSP ATCKPSGMMR IGRQWTELQG  60
ARDWDGLLNP LDGALRGELV RYGEFVRAAY ASFDFDGGAP SSYGSCRFPT SSLLRRSGLP  120
ETGYRVTGIL HAASTSAPGW LSCRSSYIGY VAVCDDEDEI ERLGRRDVVI AFRGTATCGE  180
WVDNFKSTLT HLPPRSGDGE AAPPMVESGF WRLFTTPGEA HGSLQQQVRG EVQRIVSEYG  240
GEGMPPLSIT VTGHSLGAAL AVLTAYDITT NSPMQRHGGG DDDDGEAPMV TAVSFGGPRV  300
GNAAFRRRLE ESGGKVLRVV NSNDVVTKVP GFPVDGDDCG GGAREGDAPA RRKPRLPRWL  360
VSKMGWEYSD VGRELRLCSQ GDTARNVVAS HDLDLYLKLV AACTY                 405

SEQ ID NO: 22           moltype = DNA  length = 1218
FEATURE                 Location/Qualifiers
source                  1..1218
                        mol_type = other DNA
                        organism = Oryza sativa
SEQUENCE: 22
atggcggctt ctatctccgg agctcgcact tgctacccta gcgcggcggt ggcgcgacgt  60
ggcggcggcg gcggccggtg ctgctccgtc gtcaggagct cgctggcgac ctcgtcgccg  120
gcgacgtgca agccgtcagg gatgatgcgg attggcaggc agtggacgga gctccagggt  180
gctcgtgatt gggacggcct gcttaacccg ctcgacggcg cgctccgggg cgagctcgtc  240
cgctacggcg agttcgtccg cgccgcgtac gccagcttcg acttcgacgg cggcgcgccg  300
tcgtcgtatg ggtcgtgccg gtttccgacc agctccctgc tgcgccgctc cgggctccct  360
gagactggct accgggtcac cgggatcctc cacgccgcgt cgacgtcggc gccgggctgg  420
ctgtcgtgca ggtccagcta cattgggtac gtcgcggtgt gcgacgacga ggacgagatc  480
gagcggctgg gtcgccgcga cgtcgtcatt gcgttccgcg gcacggcgac gtgcggcgag  540
tgggtggaca acttcaagtc cactctcacc cacctgccgc cgcgatccgg cgacggcgag  600
gcggcgccgc cgatggtgga gagtggattc tggaggctct tcaccacccc gggcgaagcg  660
cacggcagcc tgcagcaaca agtgcgcggc gaggtgcagc ggatcgtcag cgagtacggc  720
ggcgagggca tgccgccgtt gagcatcacg gtcaccggac acagcctcgg cgccgcgctc  780
gcggtgctca ccgcctacga catcacgaca aactccccca tgcaacgcca cggcggcggc  840
gacgacgacg acggcgaggc gccgatggtg accgccgtgt cgttcggcgg gccgcgcgtg  900
ggcaacgcgg cgttccggcg aaggctggag gagagcggcg gcaaggtgct ccgcgtggtg  960
aactcgaacg acgtcgtgac caaggtgccg gggttccccg tcgacggcga cgactgcggc  1020
ggcggcgctc gggagggcga cgcgccggcg aggaggaaac cgaggttgcc gaggtggctg  1080
gtgtccaaga tggggtggga gtacagcgac gtcggccgcg agctgcgcct ttgcagccag  1140
ggcgacacgg cgcgcaacgt ggttgcatcg catgaccttg atttgtatct caagctcgtg  1200
gcagcctgca catattag                                               1218

SEQ ID NO: 23           moltype = AA  length = 412
FEATURE                 Location/Qualifiers
source                  1..412
```

```
                         mol_type = protein
                         organism = Sorghum bicolor
SEQUENCE: 23
MAAAAASISG SRTCYPSGGV PMASGGRRRT VIRSSFAPGS PASTPSTVRI GSKWTELQGA  60
RDWDGLLSPL DGALRGELVR YGEFVRAAYA SFDFEGGAPS YGSCRFPSRS LLRRAGMPGT  120
GYRVTRLLHA ASSCTASLRW WLPSSSPPPC GSSYIGFVAV CDDEREIERL GRRDVVVAFR  180
GTATCGEWVD NFKSGLTRLP TIPTTMTGGG EDDGEEAMVE RGFWRLFTAP GEAHSSLQQQ  240
VRDEARRIAH EYGGSGMPPL SITVTGHSLG AALAVLTAHE IATTQQQQR QEDGEPAAMM  300
VTAVSFGGPR VGNAAFRRRM EESGGKVLRV VNSDDIVTKV PGFPVHEQGD GGDQPAKGMM  360
KARLPRWLVA KMGWAYADVG RELRLSQAGS PPNVVASHDL DLYLKLVASC TD          412

SEQ ID NO: 24            moltype = DNA  length = 1239
FEATURE                  Location/Qualifiers
source                   1..1239
                         mol_type = other DNA
                         organism = Sorghum bicolor
SEQUENCE: 24
atggcggcgg cggcggcgtc tatctccgga tcccgcacct gctaccctag cggcggcgtc  60
ccaatggcca gcggcggccg gcggcgcacc gtcatcagga gctccttcgc gcccggctcg  120
ccggcgtcga cgccatcgac ggtgcggatc ggcagcaagt ggacggagct ccagggcgcg  180
cgggactggg acggcctgct gagcccgctg gacggcgcgc tccggggcga gctggtccgg  240
tacggggagt tcgtgcgcgc ggcgtacgcc agcttcgact tcgagggcgg cgcgccgtcc  300
tacggctcct gccggttccc gagccgctcc ctgctgcgcc gcgcggggat gccggggacc  360
gggtaccggg tcacgcgcct cctccacgcc gcgtcgtcgt gcaccgcgtc gctccggtgg  420
tggctaccct cgtcgtcgcc gccgccgtgc gggtccagct acatcggctt cgtcgcggtg  480
tgcgacgacg agcgcgagat cgaacggctc ggccgccgcg acgtcgtcgt cgcgttccgc  540
ggcaccgcca cgtgcggcga gtgggtggac aacttcaagt ccggcctcac acggctcccg  600
acgatcccga cgacgatgac cggcgggggg gaggacgacg gcgaggaggc gatggtggag  660
cgcgggttct ggaggctctt cacggcgcca ggcgaggcgc acagcagcct gcagcagcag  720
gtgcgcgacg aggcgcggcg gatcgcccac gagtacggcg gcagcggcat gccgccgctg  780
agcatcacgg tgacggggca cagcctcggc gcggcgctcg cggtcctcac cgcccacgag  840
atcgcgacga cgcagcagca gcagcagcga caggaagacg gcgagccggc ggcgatgatg  900
gtgacggccg tgtcgttcgg cgggccgcgc gtgggcaacg cggcgttccg gcggaggatg  960
gaggagagcg gcggcaaggt gctccgcgtg gtgaactcgg acgacatcgt gaccaaggtg  1020
ccggggttcc cagtgcacga gcagggcgac ggcggcgacc agccggcgaa ggggatgatg  1080
aaggcgaggc tgccgaggtg gctcgtcgcc aagatggggt gggcgtacgc cgacgtaggg  1140
cgcgagctgc ggctgagcca ggccggctcg ccgcccaacg tggtggcctc gcatgacctc  1200
gacttgtacc tcaagctcgt cgcttcctgc acagactag                        1239

SEQ ID NO: 25            moltype = AA  length = 402
FEATURE                  Location/Qualifiers
source                   1..402
                         mol_type = protein
                         organism = Zea mays
SEQUENCE: 25
MAAAAAAISG SRTCYPSVPM ARGGRRRTSG CTVTRSSFAP CTPASTPSAQ RIGSKWAELQ  60
GARDWDGLLS PLDGALRGEL VRYGEFVRAA YASFDFDGGA PSYGSCRFPS RSLLRRAGMP  120
GTGYRVTRLL HAASTSAPGW LPSSPPCGSS YIGFVAVCDD ESEIERLGRR DVVVAFRGTA  180
TCGEWVDNFK SGLTRLPTTG TDEEEEEPM VESGFWRLFT APGEAHSSLQ QQVRDEARRI  240
ANEYGGSGMP PLSITVTGHS LGAALAVLTA HEITTQQRQE HGSGEPMMVT AVSFGGPRVG  300
NVAFRRRLEE SGGKVLRVVN SDDIVTKVPG FPVVHEHDDD DSGAQPAKGM MKARLPRWLV  360
SKMGWGYTDV GRELRLSSHS QANVVASHDL DLYLKLVASC TD                     402

SEQ ID NO: 26            moltype = DNA  length = 1209
FEATURE                  Location/Qualifiers
source                   1..1209
                         mol_type = other DNA
                         organism = Zea mays
SEQUENCE: 26
atggcggcgg cggcggcggc tatctccgga tcccgcacct gctaccctag cgtcccaatg  60
gcgcgcggcg gccggcggcg caccagcggc tgcaccgtca ccaggagctc cttcgcgccc  120
tgcacgccgg cgtccacgcc ctcggcgcag cggatcggaa gcaagtgggc ggagctccag  180
ggcgcgcgcg actgggacgg cttgctgagc ccgctggacg gcgcgctacg aggcgagctg  240
gtccggtacg gggagttcgt gcgcgcggcc tacgcgagct tcgacttcga cggcggcgcg  300
ccgtcctacg gctcctgccg gttcccgagc cgctcccttc tgcgccgcgc cgggatgccg  360
ggcacggggt accgggtcac ccgcctcctc cacgccgcgt ccacctcggc gcccgggtgg  420
cttccgtcgt cgccgccctg cggctccagc tacatcggct tcgtggcggt gtgcgacgac  480
gagagcgaga tcgagcggct cggccgccgc gacgtcgtgg tcgcgttccg cggcaccgcc  540
acgtgcggcg agtgggtgga caacttcaag tccggcctca cacggctccc gaccactggc  600
actgacgagg aggaggagga ggagccgatg gtggagagtg ggttctggag gctcttcacc  660
gcgccaggcg aggcgcacag tagcctgcag cagcaggtgc gcgacgaggc gcggcggatc  720
gccaacgagt acggcgggag cggcatgcca ccgctgagca tcacggtgac ggggcacagc  780
ctcggcgcgg cgctcgcggt gctcaccgcc cacgagatca cgacgcagca gagacaggaa  840
cacggcagcg gcgagccgat gatggtgacg gccgtgtcgt tcggcgggcc gcgcgtgggc  900
aacgtggcgt tccggcgcag gctggaggag agcggcggca aggtgctccg cgtggtcaac  960
tcggacgaca tcgtgaccaa ggtaccgggg ttcccggtgg tgcacgagca cgacgacgac  1020
gacagcggcg cccagccggc gaaggggatg atgaaggcga ggctgccgag gtggctcgtc  1080
tccaagatgg ggtgggggta caccgacgtg gggcgcgaac tgcggctgag cagccatagc  1140
caggccaacg tggtggcctc gcatgacctc gacttgtacc tcaagctcgt tgcttcctgc  1200
```

```
acagactag                                                         1209

SEQ ID NO: 27          moltype = AA  length = 517
FEATURE                Location/Qualifiers
source                 1..517
                       mol_type = protein
                       organism = Arabidopsis thaliana
SEQUENCE: 27
MQTLTPNADI FHAKRRRFTC NTHTSTLIPT KPLSVSPARK TNKEHLRNLE NVLRTSSNSI  60
DHIENVTSRQ EKTTKNTSTS SLLGGLNLAR IWPQMKAAVD EMSPKNLKRL QRLLSKSSEE  120
RSPKSKLGSK WRELHGLNNW AGLLDPLDEN LRRELVRYGE FVQAAYHAFH SDPEGSPRHV  180
ALPDGSFKVT KSLYATSSVR LPKWIDDVAP DLRWMTKQTS WVGYVAVCDD PREIRRMGRR  240
EIVIALRGTA TLLEWSENFR PNLVSMPEPK PDQSDPTRPK VECGFNSLYT TGDQHAPSLA  300
ESLVGEISRL VELYAGEELS ISVTGHSLGA AIALLAADDI AERVPHAPPV AVFSFGGPRV  360
GNREFADRLD SKGVKVLRVV NSQDVVTKVP GIFADNDKQG QSRNNGRSPG GIMEMVERNN  420
PWAYSHVGAE LRVDMKMSPY LKPNADVACC HDLEAYLHLV DGFLASNCPF RANAKRSLRK  480
LLDEQRSNVK VLYTGKSLRL NRTFHDNGDV LPSPSSS                           517

SEQ ID NO: 28          moltype = DNA  length = 1554
FEATURE                Location/Qualifiers
source                 1..1554
                       mol_type = other DNA
                       organism = Arabidopsis thaliana
SEQUENCE: 28
atgcagacac ttacgcctaa cgccgacata ttccatgcaa aacgccgtcg tttcacttgc  60
aacactcaca catcgacttt gattccgacg aagccgctct cagtttctcc cgcgagaaaa  120
accaacaaag aacatctcag aaaccttgag aacgttctta gaacttcgtc aaactctata  180
gatcatatcg aaaatgtaac ttctcgtcaa gagaagacga cgaagaatac atcgacgtca  240
tcacttctcg gaggtttgaa tttggcgcga atatggcctc agatgaaagc agccgtcgac  300
gaaatgtcgc caaagaatct gaaacggctc caaaggcttc tctcaaagtc atccgaggaa  360
cgttcgccga agagtaaact cgggtctaaa tggcgggagc tacacgggtt aaacaactgg  420
gccgggttgt tggatccgtt agacgagaat ctccggcgag agcttgtccg ctacggagag  480
tttgtacaag cggcttatca cgcgtttcac tcagacccgg aaggttcgcc gagacacgtg  540
gcgttacctg atgggtcatt taaagtgacc aagagtcttt acgccacgtc atccgttcgt  600
ttacctaaat ggatcgatga cgttgcaccg gatctccggt ggatgactaa acagacgagc  660
tgggttggtt acgtggcggt gtgtgatgat ccgagagaga tccgacggat gggaaggagg  720
gagatcgtca tcgccctccg tggaaccgcc acgttgctcg aatggtcaga gaatttcagg  780
cccaatctcg tttcaatgcc tgagcccaaa cccgatcaat ccgacccgac tcgacccaaa  840
gtggaatgcg gatttaatag cctctacacg acgggtgacc aacacgcacc aagcctcgcc  900
gagtctttgg tcggcgaaat cagccggctc gtcgagctct atgcaggaga ggagctgagt  960
atcagcgtaa ccggccacag cctcggcgcc gcaatcgcgc ttctcgccgc cgacgacatc  1020
gccgagcgtg ttccacacgc gcctccggtt gcggtgtttt cctttggtgg gcctcgagtc  1080
gggaaccgtg agttcgcgga tcgtttggat tcgaaaggag tgaaagtcct ccgcgtggtt  1140
aacagccaag atgtggtcac gaaagtcccc ggaatattcg ccgataacga taaacagggg  1200
caaagtcgta ataacgggag aagtccaggg ggtattatgg aaatggtgga gaggaacaat  1260
ccatgggctt actcgcatgt gggagcagag ctccgtgtag acatgaagat gtctccgtac  1320
ttgaaaccaa acgctgacgt ggcgtgttgc catgaccttg aggcgtactt gcacttagtc  1380
gacgggtttt tggcatctaa ctgtccgttt cgggcaaacg cgaaacggag tttaaggaaa  1440
ctgttggatg agcaacggtc aaacgtcaag gttttgtaca caggaaagtc tttaagactt  1500
aaccgtactt ttcatgataa cggagatgtt ttgcctagtc cgtcgtcttc atga        1554

SEQ ID NO: 29          moltype = AA  length = 527
FEATURE                Location/Qualifiers
source                 1..527
                       mol_type = protein
                       organism = Arabidopsis thaliana
SEQUENCE: 29
MASLSLPITL KNPRFFSSSP QNIFKTQPQT LVLTTKFKTC SIICSSSCTS ISSSTTQQKQ  60
SNKQTHVSDN KREEKAEEEE EEKEVSLREI WREVQGCNNW EGQLDPMNNH LRREIIRYGE  120
FAQACYDSFD FDPHSKYCGS CKYHPSDFFL NLDLHLHKGY TITRYLYATS NINLPNFFQK  180
SKLSSIWSQH ANWMGFVAVA TDEEEVSRLG RRDIVIAWRG TVTYLEWIYD LKDILCSANF  240
GDDPSIKIEL GFHDLYTKKE DSCKFSSFSA REQVLAEVKR LIEYYGTEEE GHKTSITVTG  300
HSLGASLALV SAYDIAELNL NHVPENNYKI PITVFSFSGP RVGNLRFKER CDELGVKVLR  360
VVNVHDKVPS VPGIFTNEKF QFQKYVEEKT SFPWSYAHVG VELALDHKKS PFLKPTKDLG  420
CAHNLEALLH LVDGYHGKDE EAEKRFCLVT KRDIALVNKS CDFLRGEYHV PPCWRQDENK  480
GMVKNGDGQW VLPDRPLLEP HGPEDIAHHL QQVLGKVNDD NFKPTTT                527

SEQ ID NO: 30          moltype = DNA  length = 1584
FEATURE                Location/Qualifiers
source                 1..1584
                       mol_type = other DNA
                       organism = Arabidopsis thaliana
SEQUENCE: 30
atggcttctc tatctttacc aataactctc aagaacccaa gattcttctc ttcttctcct  60
caaaacatct ttaaaaccca accccaaacc ctagttttga caacaaagtt caagacttgt  120
tccatcattt gctcatcttc atgcacaagc ataagctctt caacgactca acagaagcag  180
tcaaataaac aaacccatgt gtcagacaac aaacgagaag aaaaagcgga agaagaagaa  240
gaagagaaag aagttagtct tcgagaaatt tggagagaag tacaaggttg caataattgg  300
gaaggacaac tagatccaat gaacaatcat cttcgaagag agatcatacg ttatggcgaa  360
```

```
tttgctcaag cttgctatga ctcattcgac ttcgatcctc actctaaata ctgtggctct  420
tgcaaatacc atccttctga tttcttctta aaccttgacc tacatctcca caaaggctac  480
accataacac gttacctcta cgctacatcc aacataaacc tcccaaactt cttccagaaa  540
tcaaaactca gctcgatttg gagccaacac gcgaactgga tgggttttgt tgctgtagct  600
acggacgaag aagaggtgag tcggctcggg agacgtgaca tagtcattgc ttggagaggc  660
acagtcactt atctcgaatg gatctatgac ttaaaagaca ttctttgttc agctaacttc  720
ggtgacgacc catctatcaa gattgaatta gggtttcatg acttatacac caagaaagaa  780
gattcttgca aattctcttc cttctcggct cgggaacagg ttttggctga agtcaaacgg  840
cttattgagt actacggtac cgaagaagaa ggtcacaaga caagcatcac cgtgacaggg  900
cacagcctcg gcgcctctct ggctttggtc agtgcttatg atatcgcaga gctaaacttg  960
aatcacgtac cggagaacaa ctataaaatt ccaattactg ttttctcctt ctcgggacct  1020
cgagtaggta acttgaggtt caaggaacga tgtgacgaac taggggttaa agttctgaga  1080
gtcgttaatg tacacgacaa ggtacccttct gttccaggga tattcacaaa cgagaagttt  1140
cagtttcaga agtatgtgga agaaaaaaca tcattcccgt ggagctacgc gcacgtcggc  1200
gtggagcttg ccttggacca caagaaaagc ccatttctga aaccgactaa ggatttgggt  1260
tgtgcacata acctagaagc tttgcttcat ttggtggatg gttatcatgg aaaagacgaa  1320
gaagcagaga agagatttg tttggtgaca aagcgagaca tagctttagt gaataagagt  1380
tgtgatttct tgagaggtga gtaccatgtg ccgccttgtt ggagacaaga tgagaacaaa  1440
ggtatggtca agaacggcga tggacagtgg gttcttccgg accgaccact gcttgaacct  1500
cacggaccgg aggatatcgc tcatcatctt caacaagttc ttgggaaggt taacgatgat  1560
aattttaaac ccacaacgac ttaa                                    1584

SEQ ID NO: 31          moltype = AA  length = 529
FEATURE                Location/Qualifiers
source                 1..529
                       mol_type = protein
                       organism = Arabidopsis thaliana
SEQUENCE: 31
MAAIPSHNNL LTINHKNSIT GSSSLNTNFS EINFPAKFRV ATRALSRTDE SSLSAVISRL  60
ERERRERQGL LIEEAEGAGE LWMTAEDIRR RDKKTEEERR LRDTWRKIQG EDDWAGLMDP  120
MDPILRSELI RYGEMAQACY DAFDFDPASK YCGTSRFTRL EFFDSLGMID SGYEVARYLY  180
ATSNINLPNF FSKSRWSKVW SKNANWMGYV AVSDDETSRN RLGRRDIAIA WRGTVTKLEW  240
IADLKDYLKP VTENKIRCPD PAVKVESGFL DLYTDKDTTC KFARFSAREQ ILTEVKRLVE  300
EHGDDDDSDL SITVTGHSLG GALAILSAYD IAEMRLNRSK KGKVIPVTVL TYGGPRVGNV  360
RFRERMEELG VKVMRVVNVH DVVPKSPGLF LNESRPHALM KIAEGLPWCY SHVGEELALD  420
HQNSPFLKPS VDVSTAHNLE AMLHLLDGYH GKGERFVLSS GRDHALVNKA SDFLKEHLQI  480
PPFWRQDANK GMVRNSEGRW IQAERLRFED HHSPDIHHHL SQLRLDHPC             529

SEQ ID NO: 32          moltype = DNA  length = 1590
FEATURE                Location/Qualifiers
source                 1..1590
                       mol_type = other DNA
                       organism = Arabidopsis thaliana
SEQUENCE: 32
atggcggcta ttccttccca caacaacctt cttaccatca accacaaaaa ctccataacc  60
ggttcttctt ccctaaatac caatttctca gaaatcaatt ttcccgccaa attccgagta  120
gctacgagag ctttgtccag aaccgacgag tcgtctttat ccgccgtgat ttctcgcctc  180
gagcgagaaa ggcgggaaag acaaggttta ttaatcgagg aagcggaagg agctggagaa  240
ctatggatga cggcggaaga tattcgccgg cgagataaaa aaaccgaaga agaaagaaga  300
ctaagagaca cgtggcgtaa gatccaagga gaagacgatt gggccgggtt aatggatcca  360
atggatccaa ttcttagatc ggagctaatc cgttacggcg aaatggctca agcttgttac  420
gacgctttcg atttcgatcc cgcttccaaa tactgcggca cctccaggtt cacgcgactc  480
gagttcttcg attctctcgg aatgatcgat tccggttacg aggtggcgcg ttacctctac  540
gcgacgtcga acatcaatct cccgaacttc ttctcgaaat cgcggtggtc taaagtctgg  600
agcaaaaacg ctaattggat gggatacgtc gccgtttcag acgacgaaac gtctcgtaac  660
cgactcggcc gccgtgatat cgcgattgcg tggagaggaa ccgttacgaa acttgaatgg  720
atcgcggatc taaaggatta tttaaaaccg gtaaccgaaa acaagatccg atgccccgac  780
ccggccgtta aagtcgaatc cggattctta gatctctaca ctgacaaaga cacaacctgc  840
aaattcgcga gattctcagc gcgtgaacag attttaacgg aggtgaaacg gttagtggaa  900
gaacacggcg acgacgatga ttccgattta agcatcaccg tgacgggaca cagtctcggc  960
ggcgcgttag cgatattaag cgcgtacgat atagcggaga tgagattgaa tcggagtaag  1020
aaagggaaag tgattccggt gacggtgttg acatacggag gaccgagagt tgggaacgtt  1080
aggtttaggg agaggatgga ggaattggga gtgaaagtga tgagagtagt gaatgttcac  1140
gacgtggttc ccaagtcgcc gggattgttt ttgaacgaga gtagacctca cgcgctgatg  1200
aagatagcgg aggggttgcc gtggtgttat agccacgtgg gggaggagct ggcgttggat  1260
catcagaact cgccgtttct taaaccttcc gttgatgttt ctactgctca taatcttgaa  1320
gctatgcttc atttacttga cgggtatcat ggaaaaggag agagatttgt gctgtcgagt  1380
gggagagacc atgcgctagt gaacaaagcg tcggactttt tgaaagagca tttacaaatt  1440
ccaccgtttt ggcgtcaaga cgcgaataaa ggaatggttc ggaacagtga aggtcgttgg  1500
attcaagccg agcgtctccg ttttgaggat catcattctc ctgatatcca ccaccatctc  1560
tctcagctcc gtcttgatca tccttgttaa                                    1590

SEQ ID NO: 33          moltype = AA  length = 515
FEATURE                Location/Qualifiers
source                 1..515
                       mol_type = protein
                       organism = Arabidopsis thaliana
SEQUENCE: 33
MATIPSHNLR PHTTNQRTQY SLSFRPHFSR STLITFPARS SPARAMSRTD EEASISTRLE  60
```

-continued

```
QESYGLTTAE DIRRRDGEAK ESKRLRDTWR KIQGEDDWAG LMDPMDPVLR SELIRYGEMA  120
QACYDAFDFD PFSRYCGSCR FTRRHLFDSL GIIDSGYEVA RYLYATSNIN LPNFFSKSRW  180
SKVWSKNANW MGYVAVSDDN EATRCRLGRR DIAIAWRGTV TRLEWIADLK DFLKPVSGNG  240
FRCPDPAVKA ESGFLDLYTD KDTSCNFSKF SAREQVLTEV KRLVERYGDE EGEELSITVT  300
GHSLGGALAV LSAYDVAEMG VNRTRKGKVI PVTAFTYGGP RVGNIRFKER IEKLGVKVLR  360
VVNEHDVVAK SPGLFLNERA PQALMKLAGG LPWCYSHVGE MLPLDHQKSP FLKPTVDLST  420
AHNLEALLHL LDGYHGKGQR FVLSSGRDPA LVNKASDFLK DHFMVPPYWR QDANKGMVRN  480
TDGRWIQPDR IRADDQHAPD IHQLLTQLHH PSQLL                            515

SEQ ID NO: 34          moltype = DNA  length = 1548
FEATURE                Location/Qualifiers
source                 1..1548
                       mol_type = other DNA
                       organism = Arabidopsis thaliana
SEQUENCE: 34
atggcgacca ttccctccca caaccttcgt cctcatacga ccaaccaaag gactcagtac  60
tctctttcct tcagaccaca cttttcacgc tctactctga tcactttccc ggcaagatca  120
tcgccggcga gggctatgtc cagaaccgac gaggaggctt caatatctac aaggctcgag  180
caagaaagct atgggctgac gacggcagag gacattcgcc gacgggatgg agaagcaaaa  240
gaatccaaga ggttgagaga cacgtggcgg aagatccaag ggaagatga ttgggccggg  300
ttaatggatc cgatggaccc ggttctgaga tctgagctga tccggtacgg agaaatggcc  360
caggcctgtt acgacgcctt cgatttcgat ccattttcaa ggtactgcgg gagctgcaga  420
ttcacgcgcc gtcacttgtt cgattcgctc gggataatcg attctggcta tgaggtggcg  480
cgttatctct acgcgacgtc gaacatcaac cttcctaatt tcttctccaa atcgagatgg  540
tccaaggtgt ggagcaagaa cgccaattgg atgggttacg tggctgtatc cgacgacaac  600
gaagccacgc gctgccgttt aggacgccgc gacattgcca tcgcctggag agggactgtc  660
acgcggctcg agtggatagc tgatctcaag gatttcctca aaccggtatc cggaaacgga  720
ttccgatgcc ccgacccggc cgtaaaagcc gaatccgggt ttctggatct atacacggac  780
aaagatacat cctgcaattt ctccaaattc tcggcgcgag agcaggttct tacggaagtg  840
aagcggctgg tggaaaggta cggcgacgag gaaggagaag aactgagcat caccgtgacg  900
ggacacagtc tcggcggtgc gctggcggtg ctaagcgcgt acgacgtggc ggagatgggt  960
gtgaacagaa cgaggaaagg aaaagtgatt ccggtgacgg cgttcacgta cggaggaccg  1020
cgagttggga acattcgatt caaggagagg attgagaaat tgggagtgaa ggtgttgaga  1080
gtggtgaacg agcacgacgt cgtggcgaaa tcgccgggac tgtttctgaa cgagcgtgcg  1140
ccacaggcgc taatgaaatt ggcgggagga ttgccgtggt gctatagcca cgtgggagaa  1200
atgctgccgt tggatcatca gaagtctccg ttccttaagc ccaccgttga tctttctacg  1260
gctcataact tggaagctct cctccatctc cttgacgggt atcatgggaa aggacagaga  1320
tttgtgttat caagtgggag agatccagcg ttagtgaaca aagcatctga tttttgaaa  1380
gaccatttca tggtccctcc ttattggcgc caagacgcaa acaaagggat ggtgaggaac  1440
actgacggcc gttggattca acctgatcgc atccgtgcag atgatcaaca tgctcctgac  1500
atacatcaac tcctcaccca actccatcat ccatcacaac tcttgtaa              1548

SEQ ID NO: 35          moltype = AA  length = 484
FEATURE                Location/Qualifiers
source                 1..484
                       mol_type = protein
                       organism = Arabidopsis thaliana
SEQUENCE: 35
MALIQNPNMK HAPFLRNRSP QQTLFIPYTL SLPISYQNPK RLKTANSSSS SSLLAPVILN  60
SPVASSSPPP IYCAPKFPCS SGAATVPLSR VWREIQGCNN WKDLIEPLNP LLQQEITRYG  120
NLVSTCYKAF DLDPNSKRYL NCKYGKQTLL KETEIDQPED YQVTKYIYAT PDININISPI  180
QNEMNRRARW VGYVAASSDD SVKRLGRRDI VVTFRGTVTN PEWLANFMSS LTPARFHPHN  240
PRLDVKVESG FLSLYTSDES ESKFGLESCR QQLLSEISRL MNKYKGEEMS ITLAGHSMGS  300
SLAQLLAYDI AELGLNRRIG KGDIPVTVFS FAGPRVGNLE FKKRCEELGV KVLRITNVND  360
PVTKLPGVLF NENFRVLGGF YELPWSCSCY VHVGVELTLD FFDVQNISCV HDLQTYIDLL  420
NQRRTNSRSV DSDEDEDSDN VALEFLKTNG EKMMFLKRQR MMYWSNAVDL LFSFSNHMSY  480
CNIF                                                              484

SEQ ID NO: 36          moltype = DNA  length = 1455
FEATURE                Location/Qualifiers
source                 1..1455
                       mol_type = other DNA
                       organism = Arabidopsis thaliana
SEQUENCE: 36
atggccttga tccaaaaccc taatatgaaa catgctccat ttctaagaaa cagatctcca  60
caacaaacac tctttattcc gtatactctt tctctcccta tttcttacca aaaccccaaa  120
agacttaaaa ctgctaattc ttcttcttct tcttctctat tagcaccagt gattctaaat  180
tctccggttg cttcttcttc tcctcctccg atatattgtg caccaaagtt tccttgctcc  240
agtggggcag cgactgtacc cttatctcgg gtatggagag agatacaagg atgtaacaac  300
tggaaagatc tcatcgaacc tttgaaccct cttctccaac aagagatcac tcgctacggc  360
aacttagttt ccacttgtta caaagccttc gatctagacc ctaattccaa acgttacttg  420
aactgcaagt acggcaaaca aaccctactt aaagaaaccg aaatcgacca acctgaggac  480
taccaagtca caaaatatat ctacgccaca ccggatatta acatcaacat cagtcctatc  540
cagaacgaga tgaatcgacg agcgcgttgg gtaggttacg ttgcagcttc atccgatgac  600
tcggtgaaac gtttagggag gagagacatt gtggtgacgt ttcgtggaac ggtaactaac  660
cctgaatggt tggcaaattt catgagctct ttaactcctg ctaggttcca tcctcataac  720
ccgcgtctcg acgtgaaggt tgaatccggg ttcttgagtt tatacacatc agatgagagt  780
gagagcaaat tcggactaga gagctgcaga caacagcttc tgtccgaaat ctcgagattg  840
atgaataagt ataaaggaga agagatgagt atcacactcg ctggacatag catgggaagc  900
```

-continued

```
tcattggctc aacttcttgc ttatgacatt gcggaactag gtttaaaccg gaggattggc  960
aagggagata ttccggtgac cgtgttctct ttcgcaggac ctagggttgg taacttggag  1020
tttaaaaaac gttgcgaaga gctaggtgtt aaggtcttga ggatcactaa cgtcaatgat  1080
ccggtcacaa aacttccagg tgttttattc aatgagaatt ttagggtttt aggtggtttt  1140
tatgagcttc catggagctg ttcatgttat gttcatgttg gggtggaact cacgctagat  1200
tttttcgatg ttcaaaacat ttcttgcgtt cacgatctcc aaacctatat cgatcttcta  1260
aaccaacgga gaactaactc gagatcagtc gattccgatg aagatgagga cagtgacaat  1320
gttgcattag agtttttaaa gacaaatggc gagaagatga tgttcttgaa gagacaacga  1380
atgatgtatt ggtccaatgc cgtggatcta ctttttctt tttctaacca tatgtcgtat  1440
tgtaatatat tttag                                                  1455

SEQ ID NO: 37          moltype = AA  length = 545
FEATURE                Location/Qualifiers
source                 1..545
                       mol_type = protein
                       organism = Nicotiana benthamiana
SEQUENCE: 37
MQVAAATNVH FFQARRSSFK YCNGSSPLNP IPRATAVNVL KTVATPPTST TEMTKKHLSN  60
LEKLLQKKSQ PHPMDSAEQI IQETKQRKTG ENRGRNMLEG LNLARIWPEM KAAEEYSPRH  120
LVKLHRMLSS KSMEYSPRNN LGSRWREYHG CKDWLGLIDP LDENLRRELV RYGEFIQAAY  180
HCFHSNPATS DRENSDVARN VSLPDRSYEV TKSLYATSSV GLPKWVDDVA PDLGWMTQRS  240
SWIGYIAVCD DKTEIQRMGR RDIVIALRGT ATCLEWGENF RDVLVQMPGE NDSVEGQPKV  300
ECGFLSLYQT GGNKIPSLAE SVVNEVKRLI EMYKGESLSI TVTGHSLGAA LALLVADDIS  360
TCTPDSPPVA VFTFGGPRVG NKGFANRLES KNVKVLRIVN KQDVITKVPG MFVSEALDKK  420
LREKGASGVL NLLDNSMPWA YSHVGTELRV DTTKSPFLKP DADVACCHDL EAYLHLVDGY  480
LGSNESFRPN AKRSLVKLLT EQRTNIKKLY SSKGKDLSSL NLNREFNFPR PSCLPSPSVL  540
PSPSA                                                             545

SEQ ID NO: 38          moltype = DNA  length = 1638
FEATURE                Location/Qualifiers
source                 1..1638
                       mol_type = other DNA
                       organism = Nicotiana benthamiana
SEQUENCE: 38
atgcaggtgg cagcggcaac taatgttcat ttttttcagg cacggcgatc cagtttcaag  60
tactgtaatg gatcatctcc attaaaccct atacctagag ctactgctgt aaatgtatta  120
aaaacagtag caacaccacc aacttctaca acagagatga caaaaaaaca tctttcaaat  180
cttgaaaagc ttttacaaaa gaaatctcag ccacatccaa tggattcagc agagcaaatt  240
attcaagaaa caaaacagag aaaaacaggg gaaaacagag gaaggaatat gttagaaggg  300
ctaaatttgg caagaatttg gccagaaatg aaagcagctg aagaatattc tcctaggcat  360
ttggttaaat tacacaggat gttatcatca aaatcaatgg aatattctcc tagaaataat  420
cttgggagta ggtggagaga gtaccacggt tgcaaagatt ggttaggact tattgatcca  480
ttggatgaga atctccggcg agagttagtc cgatatggtg agtttattca agcagcttac  540
cattgttttc attccaaccc cgccacgtca gatagagaaa attctgacgt ggcgaggaac  600
gtgtcgttac ctgataggtc atacgaagtg actaagagct tgtatgccac gtcatccgtt  660
ggcctgccta aatgggtgga tgacgtagca ccggatcttg ggtggatgac ccaaaggtcc  720
agttggatcg gatatattgc cgtgtgcgac gacaaaaccg agatccaacg gatgggaagg  780
agggatattg tcatcgcgtt acgtggtact gccacgtgtc ttgagtgggg cgaaaatttt  840
cgcgacgtgc ttgttcaaat gccaggagaa aatgattcag ttgaaggaca accaaaagta  900
gaatgtgggt tttgagctt ataccaaaca ggtggaaata aaattccaag cttagctgaa  960
tctgtggtga atgaagtgaa aagactcatt gaaatgtaca aaggtgagag tctaagtata  1020
acagtaacag gacatagtct tggtgctgca ttagctttat tagtagcaga tgatattagt  1080
acatgtacac cagattcacc accagttgca gtttttacat ttggaggtcc tagagtaggc  1140
aacaaaggct ttgccaatcg actcgaatcg aaaaatgtta aggttttacg tatcgtgaac  1200
aaacaagacg tgattactaa agttccagga atgtttgtga gtgaggcgct tgacaaaaaa  1260
ctaagggaaa aaggcgcttc aggggtgtta aatttgcttg acaatagtat gccatgggca  1320
tattcacatg ttggtactga attaagagtc gacacaacaa agtctccgtt tttaaaacca  1380
gatgcagatg tcgcatgttg tcatgatttg gaagcatatt tgcatttggt ggatggatat  1440
ttgggatcaa atgaatcatt tagaccaaat gcaaagagaa gccttgttaa gttgttgact  1500
gaacaaagga ctaatatcaa aaaattgtac agtagtaagg gaaaagattt gagtagtctt  1560
aatcttaata gagaatttaa ttttcctaga cctagttgct tgcctagtcc tagtgttttg  1620
cctagtcctt cagcttga                                               1638
```